US012566183B2

(12) United States Patent (10) Patent No.: US 12,566,183 B2
Mitsuhashi (45) Date of Patent: Mar. 3, 2026

(54) DETECTION OF BIOMARKERS ON VESICLES FOR THE DIAGNOSIS AND PROGNOSIS OF DISEASES AND DISORDERS

(71) Applicant: NANOSOMIX, INC., Aliso Viejo, CA (US)

(72) Inventor: Masato Mitsuhashi, Irvine, CA (US)

(73) Assignee: NanoSomiX, Inc., Aliso Viejo, CA (US)

( * ) Notice: Subject to any disclaimer, the term of this patent is extended or adjusted under 35 U.S.C. 154(b) by 258 days.

(21) Appl. No.: 17/945,058

(22) Filed: Sep. 14, 2022

(65) Prior Publication Data

US 2024/0192228 A1 Jun. 13, 2024

Related U.S. Application Data

(63) Continuation of application No. 15/989,120, filed on May 24, 2018, now abandoned.

(60) Provisional application No. 62/547,024, filed on Aug. 17, 2017, provisional application No. 62/510,726, filed on May 24, 2017.

(51) Int. Cl.
*G01N 33/68* (2006.01)
*G01N 33/543* (2006.01)

(52) U.S. Cl.
CPC ... *G01N 33/6896* (2013.01); *G01N 33/54313* (2013.01); *G01N 2800/28* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS 9,347,087 B2 5/2016 Vlassov et al.
9,952,215 B2 4/2018 Ichiki et al.

2015/0119278 A1* 4/2015 Goetzl ............... G01N 33/6896
435/7.1
2015/0141634 A1 5/2015 Mitsuhashi
2015/0168400 A1* 6/2015 Ichiki ............... G01N 33/54346
435/7.1
2016/0334402 A1* 11/2016 Bosio ............... G01N 33/56966
2016/0370265 A1 12/2016 Ott et al.

FOREIGN PATENT DOCUMENTS

EP 3093664 A1 5/2015

OTHER PUBLICATIONS

Li et al., Progress in Exosome Isolation Techniques, Theranostics, 2017, 789-804.
Wang et al., The Release and Trans-Synaptic Transmission of Tau via Exosomes, Molecular Neurodegeneration, 2017, 12:5.
International Search Report and the Written Opinion of the International Searching Authority re PCT/US2018/034495.
Joshi et al., Extracellular vesicles in Alzheimer's Disease: Friends or Foes?, Int J Mol Sci., 2015, 16, 4800-4813.
Hjalmarsson et al., Neuronal and Glia-Related Biomarkers in Cerebrospinal Fluid of Patients with Acute Ischemic Stroke, Journal of Central Nervous System Disease, 2014, 6, 51-58.
Egana et al., Physical and Functional Interaction between the Dopamine Transporter and the Synaptic Vesicle protein Synaptogyrin-3, J Neurosci., Apr. 8, 2009, 29(14), 4592-4604.

* cited by examiner

*Primary Examiner* — Ann Montgomery
(74) *Attorney, Agent, or Firm* — Sandra P. Thompson; Finlayson Toffer

(57) ABSTRACT

The present invention relates to methods, compositions, and kits for detecting and quantitating biomarkers on vesicles without lysis or permeabilization of the vesicles and the use of biomarkers identified on vesicles in diagnostic and prognostic methods for various diseases and disorders. Disease and disorders of the present invention include neurological disorders, immunological disorders, placental diseases, and cancer.

21 Claims, 73 Drawing Sheets

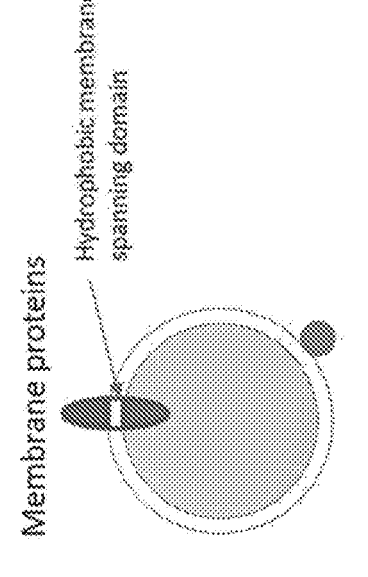
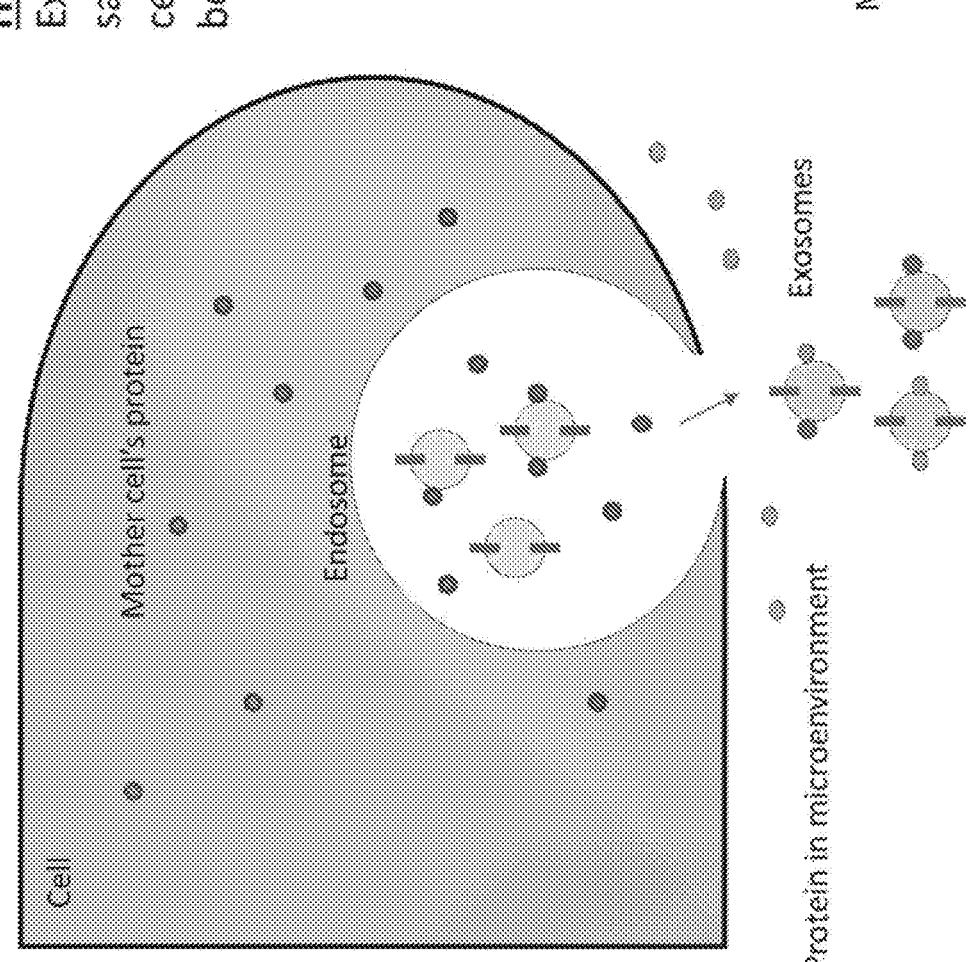
Hypothesis:
Exosome surface may be saturated with various mother cell's proteins in endosomes before releasing to outside.
Membrane proteins
Hydrophobic membrane-spanning domain
Membrane adsorbed proteins
Cell
Mother cell's protein
Endosome
Exosomes
Protein in microenvironment
FIG. 1A Exosome enumeration Cell-specific biomarkers of exosomes Cell-specific biomarkers Antibody against exosome membrane marker
(CD63, SNAP25, CD171, EAAT1, OMG, etc.)

Antibody against exosome adsorbed marker
(Tau, NRGN, GFAP, MBP, etc.)

Antibody against exosome membrane marker
(CD63, SNAP25, CD171, EAAT1, OMG, etc.)

Antibody against exosome adsorbed marker
(Tau, NRGN, GFAP, MBP, etc.)

ELISA plate

ELISA plate

ELISA plate

ELISA plate

Antibody against exosome membrane marker
(CD63, SNAP25, CD171, EAAT1, OMG, etc.)

Antibody against exosome adsorbed marker
(Tau, NRGN, GFAP, MBP, etc.)

After the presence of exosomes is confirmed, antibodies against 2 different adsorbed markers are used.

Exosomes
Cargo proteins are well discussed.
No adsorbed protein is addressed.

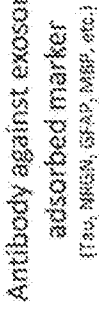
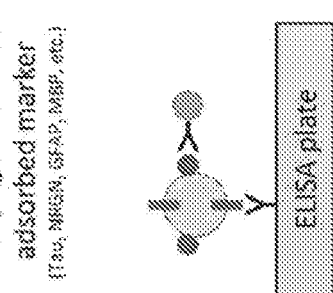

Conventional ELISA
Single antigen

ELISA plate

FIG. 1B

Anti-CD171

ELISA plate

Anti-NRGN

DETECTION OF BIOMARKERS ON VESICLES FOR THE DIAGNOSIS AND PROGNOSIS OF DISEASES AND DISORDERS

RELATED APPLICATIONS

This application is a continuation of U.S. patent application Ser. No. 15/989,120, filed on May 24, 2018, which claims priority to the U.S. Provisional Patent Application Ser. No. 62/510,726, filed on May 24, 2017, and U.S. Provisional Patent Application Ser. No. 62/547,024, filed on Aug. 17, 2017, which is hereby incorporated by reference herein in their entirety.

FIELD OF THE INVENTION

The present invention relates to methods, compositions, and kits for detecting and quantitating biomarkers on vesicles without lysis or permeabilization of the vesicles and the use of biomarkers identified on vesicles in diagnostic and prognostic methods for various diseases and disorders. Disease and disorders of the present invention include neurological disorders, immunological disorders, placental diseases, and cancer.

BACKGROUND OF THE INVENTION

Exosomes in biological fluids are potentially useful diagnostically for various diseases, because exosomes carry physiological and pathological materials (proteins, metabolites, RNAs, small molecules, etc.) of the mother cells from which they originate and the microenvironment near their mother cells. However, even though exosomes are recognized as valuable resources for diagnostics, current analytical methods of analyzing exosomes are too complicated and expensive for routine use in diagnostic testing.

More than 5.4 million Americans and 35 million people worldwide have Alzheimer's disease, the most common form of dementia. Currently, the only definitive way to diagnose Alzheimer's disease is by direct examination of brain tissue after a patient dies. Doctors use brain imaging, evaluation of behavior, psychiatric tests, and other means to diagnose the disease in the patients suspected of having Alzheimer's disease, but none are highly accurate, and many are costly or not practical.

In 2017, there will be an estimated 1,688,780 new cancer cases diagnosed and 600,920 cancer deaths in the US. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, leukemia, endometrial cancer, and pancreatic cancer. Similarly, millions of Americans suffer from immunological disorders and diseases caused by a dysfunction of the immune system.

Therefore, there is a need in the art for biomarkers and methods for diagnosing diseases and other disorders, such as, for example, neurological disorders, cancer, immunological disorders, and placental disease. Additionally, there is a need in the art for compositions for detecting the biomarkers as well as compositions and methods useful for treating diseases and other disorders. The present invention meets this need by providing accurate, noninvasive methods for diagnosing diseases and other disorders. The present invention further provides novel methods, assays, biomarkers, kits, and compositions for diagnosing, prognosing, predicting, and treating various diseases and disorders.

SUMMARY OF THE INVENTION

The present invention relates to methods, compositions, and kits for detecting and quantitating biomarkers on vesicles. In particular, the invention provides a method for selectively capturing vesicles carrying surface markers of interest on a solid support and detecting membrane-bound and adsorbed biomarkers on the captured vesicles without the need for lysis or permeabilization of the vesicles. Measurement of biomarkers on vesicles is useful in diagnostic and prognostic methods for various diseases. In particular, the present invention provides methods of diagnosing or prognosing a disease or disorder in a subject, identifying a subject at risk of a disease or a disorder, or prescribing a therapeutic regimen or predicting benefit from therapy in a subject having a disease or a disorder. In certain embodiments, the present invention provides methods of diagnosing or prognosing a neurological disorder in a subject, identifying a subject at risk of a neurological disorder, or prescribing a therapeutic regimen or predicting benefit from therapy in a subject having a neurological disorder. In other embodiments, the present invention provides methods of diagnosing or prognosing an immunological disorder in a subject, identifying a subject at risk of an immunological disorder, or prescribing a therapeutic regimen or predicting benefit from therapy in a subject having an immunological disorder. In other embodiments, the present invention provides methods of diagnosing or prognosing cancer in a subject, identifying a subject at risk of cancer, or prescribing a therapeutic regimen or predicting benefit from therapy in a subject having cancer. In other embodiments, the present invention provides methods of diagnosing or prognosing placental disease in a subject, identifying a subject at risk of a placental disease, or prescribing a therapeutic regimen or predicting benefit from therapy in a subject having a placental disease.

In one aspect, the invention provides a method comprising: a) providing a biological sample comprising vesicles; b) contacting a solid support comprising capture agents associated therewith with the biological sample under conditions wherein the capture agents selectively bind to a first biomarker, if present, on the vesicles, thereby capturing said vesicles having said first biomarker on the solid support; c) separating the solid support from the biological sample; and d) detecting a second biomarker on the vesicles captured on the solid support using a detection agent that selectively binds to the second biomarker, wherein the vesicles are not lysed or permeabilized.

In some embodiments, the methods of the invention further comprise detecting a secretory protein on the vesicles captured on the solid support. In certain aspects, the secretory protein is selected from the group consisting of cytokines, growth factors, chemokines, and interleukins. In other aspects, the cytokine is selected from the group consisting of IL1b, IL34, IL6, IL8, IL16, IL23A, IL32, IL33, CX3CL1, CCL2, CXCL12, TNFalpha, TNFSF10, IL12B, nociceptin, GnRH, FasL, and TNFSF13.

In certain embodiments, the vesicles are selected from the group consisting of exosomes, microparticles, microvesicles, nanosomes, extracellular vesicles, ectosomes, and apoptotic bodies.

In certain embodiments, the first and second biomarkers are membrane-bound proteins or adsorbed proteins on the vesicles. For example, the first or second biomarker may be an exosome surface marker (e.g., CD81, CD63, CD171), a neuron-specific protein (e.g., synaptosome associated protein 25 (SNAP25), neurogranin (NRGN), tau, phosphorylated tau, αβ-42, and synaptophysin), an astrocyte-specific protein (e.g., glial fibrillary acidic protein (GFAP) and excitatory amino acid transporter 1 (EAAT1)), a microglia-specific protein (CD11b), an oligodendrocyte-specific protein (e.g., myelin basic protein (MBP), an oligodendrocyte myelin glycoprotein (OMG), or a chemokine (CX3CL1) or cytokine (IL1b, IL34, FasL, or IL12B). In another embodiment, the first or second biomarker is a metabolite. In another embodiment, the method further comprises detecting a cytosolic protein (e.g., glyceraldehyde-3-phosphate dehydrogenase (GAPDH), alpha-synuclein (SNCA), tyrosine hydroxygenase (TH), cathepsin D (CTSD), AchE, LAMP1, REST, SYT, SYP, SYNPO, PSD95, SV2A, GYS, HSP70, BACE, SYMPO, NEFL, caspase, ubiquitin, PSEN1, GSK, PLAP, CSH1, PSG1, or FasL) on the vesicles captured on the solid support. In another embodiment, the method further comprises detecting one or more additional biomarkers on the vesicles captured on the solid support. In some embodiments, the biomarker is selected from the group consisting of CD81, acetylcholinesterase (AchE), Lysosomal Associated Membrane Protein 1 (LAMP1), CTSD, RE1 Silencing Transcription Factor (REST), synaptotagmin (SYT), synaptophysin (SYP), synaptopodin (SYNPO), post-synaptic density protein 95 (PSD95), synaptic vesicle glycoprotein 2A (SV2A), NGRN, monocyte chemotactic protein-1 (CCL2), IL34, glycogen synthase (GYS), (OR), death receptor 6 (DR6), heat shock protein (HSP), IL12beta, alpha-beta (AB),beta-secretase (BACE), dopamine receptors (D1 and D2), serotonin receptors (2A, 2C, and 3B), GABA receptors (1-6, 5. B1, B2), glutamate receptors (1 and 2), insulin receptors, tumor necrosis factor receptors super-family (TRAL, TNF receptor, death receptor 5 and 6), neuropeptide receptors (orexin receptor, opioid receptor KOR), EpCAM, PD-L1, ErbB2, CK19, TCR, CD16, CD28, CD32, CD79a, TREM2, and NCAM. In some embodiments, the first biomarker is SNAP25 and the second biomarker is selected from the group consisting of CD81, tau, NEFL, TNFa, and IL8. In some embodiments, the first biomarker is EAAT1 and the second biomarker is CD81 or GFAP. In some embodiments, the first biomarker is OMG and the second biomarker is CD81 or MBP. In some embodiments, the first biomarker is CD11b and the second biomarker is SYP. In some embodiments, the first biomarker is DAT and the second biomarker is CD81, SNCA, or TH. In some embodiments, the first biomarker is CD11b and the second biomarker is SYP.

In another embodiment, the vesicles captured on the solid support are selected from the group consisting of neuron-derived exosomes, astrocyte-derived exosomes, oligodendrocyte-derived exosomes, and microglia-derived exosomes.

In certain embodiments, the solid support is a plate, a non-magnetic bead, a magnetic bead, a filter, a slide, a wafer, a rod, a particle, a strand, a disc, a membrane, or a surface of a tube, channel, column, flow cell device, or microfluidic device. The solid support can comprise, for example, glass, quartz, silicon, metal, ceramic, plastic, nylon, polyacrylamide, a hydrogel, or a resin.

In certain embodiments, the solid support comprises more than one type of capture agent associated therewith, for example, at least 2, 3, 4, 5, 6, 7, 8, 9, 10, 15, 20, or more different capture agents that selectively bind to different biomarkers on the vesicles.

In certain embodiments, detection of biomarker on vesicles captured on the solid support comprises using more than one type of detection agent, for example, at least 2, 3, 4, 5, 6, 7, 8, 9, 10, 15, 20, or more different detection agents that selectively bind to different biomarkers on the vesicles.

In certain embodiments, the capture agents comprise antibodies, antibody fragments, antibody mimetics, or aptamers that specifically bind to the first biomarker on the vesicles. In other embodiments, the detection agents comprise antibodies, antibody fragments, antibody mimetics, or aptamers that specifically bind to the second biomarker on the vesicles. Capture agents and detection agents may comprise monoclonal antibodies, polyclonal antibodies, chimeric antibodies, nanobodies, recombinant fragments of antibodies, Fab fragments, Fab' fragments, F(ab')$_2$ fragments, Fv fragments, or scFv fragments.

In certain embodiments, the detection agent further comprises a detectable label, for example, a fluorescent, chemiluminescent, electrochemiluminescent, bioluminescent, isotopic, or radioactive label.

In certain embodiments, detecting a biomarker on a vesicle comprises performing an immunoassay, such as an enzyme-linked immunosorbent assay (ELISA), an immunofluorescent assay (IFA), an immune-polymerase chain reaction assay, an electro-chemiluminescence immunoassay (ECLIA), and a radioimmunoassay (RIA).

The biological sample comprising vesicles may be from a subject or a cell culture supernatant. In certain embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid.

In certain embodiments, a biological sample is obtained from a subject who has been diagnosed or is suspected of having a neurological disorder, such as Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), stroke, depression, bipolar disease, epilepsy, autism, schizophrenia, brain tumor, white matter disease, brain atrophy, mental retardation, cerebellar ataxia, multiple system atrophy, concussion, subconcussive impacts, or Parkinson's disease.

In some embodiments, a biological sample is obtained from a subject who has been diagnosed or is suspected of having cancer, such as breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, or spinal axis tumors.

In some embodiments, a biological sample is obtained from a subject who has been diagnosed or is suspected of having an immunological disorder. In other embodiments, a biological sample is obtained from a subject who has been diagnosed or is suspected of having a placental disease.

In one aspect, the invention provides a method of diagnosing and treating a disease or a disorder in a subject, the method comprising: a) obtaining a biological sample comprising exosomes from the subject; b) contacting a solid support comprising capture agents associated therewith with the biological sample under conditions wherein the capture agents selectively bind to a first biomarker on the exosomes, wherein exosomes are captured on the solid support; c) separating the solid support from the biological sample; d) measuring a level of a second biomarker on the exosomes captured on the solid support, wherein the exosomes are not lysed or permeabilized; e) diagnosing the subject with the disease or disorder by comparing the level of the second biomarker to a control level of the second biomarker; and f) treating the subject for the disease or disorder if the subject is diagnosed as having the disease or disorder. In some embodiments, the first biomarker is a neuron-specific protein, an astrocyte-specific protein, a microglia-specific protein, or an oligodendrocyte-specific protein. In other embodiments, the second biomarker is a cytosolic protein, a secretory protein, a receptor protein, a transporter protein, or a membrane protein. In some embodiments, the cytosolic protein is selected from the group consisting of GAPDH, CTSD, NRGN, MBP, GFAP, Tau, phosphorylated Tau (e.g., T181), synaptophysin, SNCA, αβ-42, AchE, LAMP1, REST, SYT, TH, SYP, SYNPO, PSD95, SV2A, GYS, HSP70, BACE, NEFL, caspase, ubiquitin, PSEN1, GSK, PLAP, CSH1, PSG1, or FasL. In other embodiments, the secretory protein is selected from the group consisting of cytokines, growth factors, chemokines, and interleukins. In certain aspects, the cytokine is selected from the group consisting of IL1b, IL34, IL6, IL8, IL16, IL23A, IL32, IL33, CX3CL1, CCL2, CXCL12, TNFalpha, TNFSF10, IL12B, nociceptin, GnRH, FasL and TNFSF13. In other embodiments, the neurotransmitter receptor is selected from the group consisting of dopamine receptors (D1 and D2), serotonin receptors (2A, 2C, and 3B), GABA receptors (1-6, 5. B1, B2), glutamate receptors (1 and 2), insulin receptors, tumor necrosis factor receptors superfamily (TRAL, TNF receptor, death receptor 5 and 6), and neuropeptide receptors (orexin receptor, opioid receptor KOR). In other embodiments, the membrane protein is selected from the group consisting of EpCAM, PD-L1, ErbB2, CK19, TCR, CD16, CD28, CD32, CD79a, TREM2, and NCAM. In some embodiments, the transporter protein is a neurotransmitter transporter, a dopamine transporter (e.g., DAT), a serotonin transporter, a GABA transporter, a glutamate transporter, an insulin transporter, a tumor necrosis factor transporter, or a neuropeptide transporter. In some embodiments, the disease or disorder is a neurological disorder, an immunological disorder, a placental disease, or cancer.

In another aspect, the invention provides a method of diagnosing and treating a neurological disorder in a subject, the method comprising: a) obtaining a biological sample comprising exosomes from the subject; b) contacting a solid support comprising capture agents associated therewith with the biological sample under conditions wherein the capture agents selectively bind to a first biomarker on the exosomes selected from the group consisting of a neuron-specific protein, an astrocyte-specific protein, a microglia-specific protein, and an oligodendrocyte-specific protein, wherein neuron-derived exosomes, astrocyte-derived exosomes, oligodendrocyte-derived exosomes, or microglia-derived exosomes are captured on the solid support; c) separating the solid support from the biological sample; d) measuring a level of a second biomarker selected from the group consisting of a neuron-specific protein, an astrocyte-specific protein, a microglia-specific protein on the exosomes captured on the solid support, wherein the exosomes are not lysed or permeabilized; e) diagnosing the subject with the neurological disorder by comparing the level of the second biomarker to a control level of the second biomarker; and f) treating the subject for the neurological disorder if the subject is diagnosed as having the neurological disorder.

In other embodiments, the present invention provides a method of prognosing or monitoring the progression of a disease or disorder in a subject, the method comprising: a) obtaining a biological sample comprising exosomes from the subject; b) contacting a solid support comprising capture agents associated therewith with the biological sample under conditions wherein the capture agents selectively bind to a first biomarker on the exosomes, wherein exosomes are captured on the solid support; c) separating the solid support from the biological sample; d) measuring a level of a second biomarker protein on the exosomes captured on the solid support, wherein the exosomes are not lysed or permeabilized, thereby prognosing or monitoring the progression of the disease or disorder in the subject. In some embodiments, the method further comprises obtaining a second biological sample comprising exosomes from the subject and measuring the level of a biomarker of the present invention and comparing the level of the biomarker in the second biological samples to the level of the biomarker in the first biological sample. In some embodiments, the first biomarker is a neuron-specific protein, an astrocyte-specific protein, a microglia-specific protein, or an oligodendrocyte-specific protein. In other embodiments, the second biomarker is a cytosolic protein, a secretory protein, a receptor protein, a transporter protein, or a membrane protein. In some embodiments, the cytosolic protein is selected from the group consisting of GAPDH, CTSD, NRGN, MBP, GFAP, Tau, phosphorylated Tau (e.g., T181), synaptophysin, SNCA, aB-42, AchE, LAMP1, REST, SYT, TH, SYP, SYNPO, PSD-95, SV2A, GYS, HSP70, BACE, SYMPO, NEFL, caspase, ubiquitin, PSEN1, GSK, PLAP, CSH1, PSG1, or FasL. In other embodiments, the secretory protein is selected from the group consisting of cytokines, growth factors, chemokines, and interleukins. In certain aspects, the cytokine is selected from the group consisting of IL1b, IL34, IL6, IL8, IL16, IL23A, IL32, IL33, CX3CL1, CCL2, CXCL12, TNFalpha, TNFSF10, IL12B, nociceptin, GnRH, FasL and TNFSF13. In other embodiments, the neurotransmitter receptor is selected from the group consisting of dopamine receptors (D1 and D2), serotonin receptors (2A, 2C, and 3B), GABA receptors (1-6, 5. B1, B2), glutamate receptors (1 and 2), insulin receptors, tumor necrosis factor receptors superfamily (TRAL, TNF receptor, death receptor 5 and 6), and neuropeptide receptors (orexin receptor, opioid receptor KOR). In other embodiments, the membrane protein is selected from the group consisting of EpCAM, PD-L1, ErbB2, CK19, TCR, CD16, CD28, CD32, CD79a, TREM2, and NCAM. In some embodiments, the transporter protein is a neurotransmitter transporter, a dopamine transporter, a serotonin transporter, a GABA transporter, a glutamate transporter, an insulin transporter, a tumor necrosis factor transporter, or a neuropeptide transporter. In some embodiments, the disease or disorder is a neurological disorder, an immunological disorder, a placental disease, or cancer.

In other embodiments, the present invention provides a method of prognosing or monitoring the progression of a neurological disorder in a subject, the method comprising: a) obtaining a biological sample comprising exosomes from the subject; b) contacting a solid support comprising capture agents associated therewith with the biological sample under conditions wherein the capture agents selectively bind to a first biomarker on the exosomes selected from the group consisting of a neuron-specific protein, an astrocyte-specific protein, a microglia-specific protein, and an oligodendrocyte-specific protein, wherein neuron-derived exosomes, astrocyte-derived exosomes, oligodendrocyte-derived exosomes, or microglia-derived exosomes are captured on the solid support; c) separating the solid support from the biological sample; d) measuring a level of a second biomarker selected from the group consisting of a neuron-specific protein, an astrocyte-specific protein, a microglia-specific protein on the exosomes captured on the solid support, wherein the exosomes are not lysed or permeabilized, thereby prognosing or monitoring the progression of the neurological disease in the subject. In some embodiments, the method further comprises obtaining a second biological sample comprising exosomes from the subject and measuring the level of a biomarker of the present invention and comparing the level of the biomarker in the second biological samples to the level of the biomarker in the first biological sample.

In yet another aspect, the invention provides a method of diagnosing and treating a disease or disorder in a subject, the method comprising: a) obtaining a biological sample comprising exosomes from the subject; b) contacting a solid support comprising capture agents associated therewith with the biological sample under conditions wherein the capture agents selectively bind to a first biomarker on the exosomes, wherein exosomes are captured on the solid support; c) separating the solid support from the biological sample; d) detecting a second biomarker on the exosomes captured on the solid support, wherein the exosomes are not lysed or permeabilized; e) diagnosing the subject with the disease or disorder by comparing the level of the second biomarker to a control level of the second biomarker; and f) treating the subject for the disease or disorder if the subject is diagnosed as having the disease or disorder. In some embodiments, the first biomarker is a neuron-specific protein, an astrocyte-specific protein, a microglia-specific protein, or an oligodendrocyte-specific protein. In other embodiments, the second biomarker is a cytosolic protein, a secretory protein, a receptor protein, a transporter protein, or a membrane protein. In some embodiments, the cytosolic protein is selected from the group consisting of GAPDH, CTSD, NRGN, MBP, GFAP, Tau, phosphorylated Tau (e.g., T181), synaptophysin, SNCA, αβ-42, AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, PSG1, or FasL. In other embodiments, the secretory protein is selected from the group consisting of cytokines, growth factors, chemokines, and interleukins. In certain aspects, the cytokine is selected from the group consisting of IL1b, IL34, IL6, IL8, IL16, IL23A, IL32, IL33, CX3CL1, CCL2, CXCL12, TNFalpha, TNFSF10, IL12B, nociceptin, GnRH, FasL and TNFSF13. In other embodiments, the neurotransmitter receptor is selected from the group consisting of dopamine receptors (D1 and D2), serotonin receptors (2A, 2C, and 3B), GABA receptors (1-6, 5. B1, B2), glutamate receptors (1 and 2), insulin receptors, tumor necrosis factor receptors superfamily (TRAL, TNF receptor, death receptor 5 and 6), and neuropeptide receptors (orexin receptor, opioid receptor KOR). In other embodiments, the membrane protein is selected from the group consisting of EpCAM, PD-L1, ErbB2, CK19, TCR, CD16, CD28, CD32, CD79a, TREM2, and NCAM. In some embodiments, the transporter protein is a neurotransmitter transporter, a dopamine transporter, a serotonin transporter, a GABA transporter, a glutamate transporter, an insulin transporter, a tumor necrosis factor transporter, or a neuropeptide transporter. In some embodiments, the disease or disorder is a neurological disorder, an immunological disorder, a placental disease, or cancer.

In yet another aspect, the invention provides a method of diagnosing and treating a neurological disorder in a subject, the method comprising: a) obtaining a biological sample comprising exosomes from the subject; b) contacting a solid support comprising capture agents associated therewith with the biological sample under conditions wherein the capture agents selectively bind to a first biomarker on the exosomes selected from the group consisting of a neuron-specific protein, an astrocyte-specific protein, a microglia-specific protein, and an oligodendrocyte-specific protein, wherein neuron-derived exosomes, astrocyte-derived exosomes, oligodendrocyte-derived exosomes, or microglia-derived exosomes are captured on the solid support; c) separating the solid support from the biological sample; d) detecting a second biomarker selected from the group consisting of a neuron-specific protein, an astrocyte-specific protein, a microglia-specific protein on the exosomes captured on the solid support, wherein the exosomes are not lysed or permeabilized; e) diagnosing the subject with the neurological disorder by comparing the level of the second biomarker to a control level of the second biomarker; and f) treating the subject for the neurological disorder if the subject is diagnosed as having the neurological disorder.

In certain embodiments, the neurological disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), stroke, depression, bipolar disease, epilepsy, autism, schizophrenia, brain tumor, white matter disease, brain atrophy, mental retardation, cerebellar ataxia, multiple system atrophy, concussion, subconcussive impacts, and Parkinson's disease.

In certain embodiments, the first and second biomarkers are membrane-bound proteins or adsorbed proteins on the vesicles, including but not limited to, a neuron-specific protein selected from the group consisting of synaptosome associated protein 25 (SNAP25), neurogranin (NRGN), tau, phosphorylated tau, and synaptophysin, an astrocyte-specific proteins selected from the group consisting of glial fibrillary acidic protein (GFAP) and excitatory amino acid transporter 1 (EAAT1), a microglia-specific protein (CD11b), a cytokine selected from the group consisting of IL1b, IL34, FasL, or IL12B, a chemokine (CX3CL1), CD81, CD171, CTSD, CD63, αβ-42, an oligodendrocyte-specific protein selected from the group consisting of myelin basic protein (MBP) and oligodendrocyte myelin glycoprotein (OMG). In some embodiments, the biomarker is selected from the group consisting of CD81, acetylcholinesterase (AchE), Lysosomal Associated Membrane Protein 1 (LAMP1), CTSD, RE1 Silencing Transcription Factor (REST), synaptotagmin (SYT), NGRN, monocyte chemotactic protein-1 (CCL2), IL34, glycogen synthase (GYS), olfactory receptor (OR), death receptor 6 (DR6), heat shock protein (HSP), IL12beta, alpha-beta (AB),beta-secretase (BACE), dopamine receptors (D1 and D2), serotonin receptors (2A, 2C, and 3B), GABA receptors (1-6, 5, B1, B2), glutamate receptors (1 and 2), insulin receptors, tumor necrosis factor receptors superfamily (TRAL, TNF receptor, death receptor 5 and 6), neuropeptide receptors (orexin receptor, opioid receptor KOR), EpCAM, PD-L1, ErbB2, CK19, TCR, CD16, CD28, CD32, CD79a, TREM2, and NCAM. In some embodiments, the first biomarker is SNAP25 and the second biomarker is selected from the group consisting of CD81, tau, NEFL, TNFa, and IL8. In some embodiments, the first biomarker is EAAT1 and the second biomarker is CD81 or GFAP. In some embodiments, the first biomarker is OMG and the second biomarker is CD81 or MBP. In some embodiments, the first biomarker is CD11b and the second biomarker is SYP.

In some embodiments, the level of one or more biomarkers on exosomes in the biological sample is compared to the level of one or more biomarkers in a control sample, wherein the level of the one or more biomarkers of the biological sample is elevated compared to the control sample. In some embodiments, the level of the one or more biomarkers in the biological sample is compared to the level of one or more biomarkers in a control sample, wherein the level of the one or more biomarkers of the biological sample is decreased compared to the control sample. In some embodiments, the biomarker level determines the disease or disorder status of the subject with at least 40%, 50%, 60%, 70%, 75%, 80%, 85%, 90%, 95%, 99%, or 100% specificity. In some embodiments, the disease or disorder is a neurological disorder, an immunological disorder, a placental disease, or cancer. In some embodiments, the neurological disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), stroke, depression, bipolar disease, epilepsy, autism, schizophrenia, brain tumor, white matter disease, brain atrophy, mental retardation, cerebellar ataxia, multiple system atrophy, concussion, subconcussive impacts, and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In some embodiments, the cancer is breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, or spinal axis tumors.

In another embodiment, the invention includes a method of diagnosing and treating a disease or disorder in a subject, the method comprising: a) obtaining a biological sample comprising exosomes from the subject; b) contacting a solid support comprising capture agents associated therewith with the biological sample under conditions wherein the capture agents selectively bind to a membrane marker on the exosomes wherein the membrane marker is selected from the group consisting of SNAP25, OMG, CD11b, EAAT1 and CD171, wherein exosomes having the membrane marker are captured on the solid support; c) separating the solid support from the biological sample; d) measuring levels of one or more biomarkers selected from the group consisting of CD81, GAPDH, CTSD, NRGN, MBP, GFAP, Tau, phosphorylated Tau, CD63, $\alpha\beta$-42, CX3CL1, IL1b, and IL34 on the exosomes captured on the solid support, wherein the exosomes are not lysed or permeabilized; e) diagnosing the subject with the disease or disorder by comparing the levels of the one or more biomarkers to control levels of the biomarkers in a control sample, wherein increased levels of one or more biomarkers and/or decreased levels of one or more biomarkers compared to the control levels of the one or more biomarkers in the control sample indicate that the subject has the disease or disorder; and f) treating the subject for the disease or disorder if the subject is diagnosed as having the disease or disorder. In some embodiments, the biomarker is selected from the group consisting of CD81, acetylcholinesterase (AchE), Lysosomal Associated Membrane Protein 1 (LAMP1), CTSD, RE1 Silencing Transcription Factor (REST), synaptotagmin (SYT), NGRN, monocyte chemotactic protein-1 (CCL2), IL34, glycogen synthase (GYS), olfactory receptor (OR), death receptor 6 (DR6), heat shock protein (HSP), IL12beta, alpha-beta (AB), beta-secretase (BACE), dopamine receptors (D1 and D2), serotonin receptors (2A, 2C, and 3B), GABA receptors (1-6, 5. B1, B2), glutamate receptors (1 and 2), insulin receptors, tumor necrosis factor receptors superfamily (TRAL, TNF receptor, death receptor 5 and 6), neuropeptide receptors (orexin receptor, opioid receptor KOR), EpCAM, PD-L1, ErbB2, CK19, TCR, CD16, CD28, CD32, CD79a, TREM2, and NCAM. In some embodiments, the disease or disorder is a neurological disorder, an immunological disorder, a placental disease, or cancer.

In another aspect, the invention includes a kit for detecting biomarkers on vesicles, the kit comprising: a) a solid support comprising capture agents associated therewith, wherein the capture agents selectively bind to a first biomarker on the surface of the vesicles; and b) at least one detection agent that selectively binds to a second biomarker on the surface of the vesicles. In certain embodiments, the vesicles are selected from the group consisting of exosomes, microparticles, microvesicles, nanosomes, extracellular vesicles, and ectosomes. In yet other aspects, the invention provides a kit for detecting biomarkers on vesicles, the kit comprising: a) a solid support comprising capture agents associated therewith, wherein at least one capture agent selectively binds to a neuron-specific protein, an astrocyte-specific protein, a microglia-specific protein, or an oligo-dendrocyte-specific protein on exosomes; and b) one or more detection agents, wherein the one or more detection agents selectively binds to cytosolic proteins, secretory proteins, neurotransmitter receptors or membrane proteins on the surface of the exosomes. In some embodiments, the cytosolic proteins are selected from the group consisting of GAPDH, CTSD, NRGN, MBP, GFAP, Tau, phosphorylated Tau (e.g., T181), synaptophysin, SNCA, $\alpha\beta$-42, AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, PSG1, or FasL. In other embodiments, the secretory protein is selected from the group consisting of cytokines, growth factors, chemokines, and interleukins. In certain aspects, the cytokine is selected from the group consisting of IL1b, IL34, IL6, IL8, IL16, IL23A, IL32, IL33, CX3CL1, CCL2, CXCL12, TNFalpha, TNFSF10, IL12B, nociceptin, GnRH, FasL and TNFSF13. In other embodiments, the neurotransmitter receptor is selected from the group consisting of dopamine receptors (D1 and D2), serotonin receptors (2A, 2C, and 3B), GABA receptors (1-6, 5. B1, B2), glutamate receptors (1 and 2), insulin receptors, tumor necrosis factor receptors superfamily (TRAL, TNF receptor, death receptor 5 and 6), and neuropeptide receptors (orexin receptor, opioid receptor KOR). In other embodiments, the membrane protein is selected from the group consisting of EpCAM, PD-L1, ErbB2, CK19, TCR, CD16, CD28, CD32, CD79a, TREM2, and NCAM.

In certain embodiments, the capture agents and detection agents in the kit comprise antibodies, antibody fragments, antibody mimetics, or aptamers that specifically bind to the first biomarker on the vesicles. The antibodies may include, for example, monoclonal antibodies, polyclonal antibodies, chimeric antibodies, nanobodies, recombinant fragments of antibodies, Fab fragments, Fab' fragments, F(ab')$_2$ fragments, Fv fragments, and an scFv fragments. In another embodiment, the capture agents or detection agents comprise antibodies selected from the group consisting of an anti-CD171 antibody, an anti-synaptosome associated protein 25 (SNAP25) antibody, an anti-neurogranin (NRGN) antibody, an anti-tau antibody, an anti-synaptophysin antibody, and anti-CD63 antibody, an anti-αβ-42 antibody, an anti-CD81 antibody, an anti-CTD antibody, an anti-GAPDH antibody, an anti-IL1b antibody, an anti-IL34 antibody, an anti-CX3CL1 antibody, an anti-glial fibrillary acidic protein (GFAP) antibody, an anti-excitatory amino acid transporter 1 (EAAT1) antibody, an anti-myelin basic protein (MBP) antibody, an anti-SNCA antibody, an anti-TH antibody, an anti-CD11b antibody, and an anti-oligodendrocyte myelin glycoprotein (OMG) antibody. In some embodiments, the at least one capture agent selectively binds to CD171, CD63, CD81, SNAP25, EAAT1, CD11b, or OMG on exosomes. In other embodiments, the one or more detection agents selectively binds to CD81, GAPDH, CTSD, NRGN, MBP, GFAP, Tau, phosphorylated Tau (e.g., T181), CD63, αβ-42, CX3CL1, IL1b, or IL34 on the surface of the exosomes. In some embodiments, the at least one or more detection agents selectively binds to CD81, acetylcholinesterase (AchE), Lysosomal Associated Membrane Protein 1 (LAMP1), CTSD, RE1 Silencing Transcription Factor (REST), synaptotagmin (SYT), NGRN, monocyte chemotactic protein-1 (CCL2), IL34, glycogen synthase (GYS), olfactory receptor (OR), death receptor 6 (DR6), heat shock protein (HSP), IL12beta, alpha-beta (AB),beta-secretase (BACE), dopamine receptors (D1 and D2), serotonin receptors (2A, 2C, and 3B), GABA receptors (1-6, 5. B1, B2), glutamate receptors (1 and 2), insulin receptors, tumor necrosis factor receptors superfamily (TRAL, TNF receptor, death receptor 5 and 6), neuropeptide receptors (orexin receptor, opioid receptor KOR), EpCAM, PD-L1, ErbB2, CK19, TCR, CD16, CD28, CD32, CD79a, TREM2, or NCAM.

In certain embodiments, the detection agent in the kit further comprises a detectable label, for example, a fluorescent, chemiluminescent, electrochemiluminescent, bioluminescent, isotopic, or radioactive label.

In another embodiment, the kit further comprises reagents for performing an immunoassay. Exemplary immunoassays include an enzyme-linked immunosorbent assay (ELISA), an immunofluorescent assay (IFA), an immune-polymerase chain reaction assay, an electro-chemiluminescence immunoassay (ECLIA), and a radioimmunoassay (RIA).

In another embodiment, the invention includes a kit for diagnosing or prognosing a disease or disorder in a subject, identifying a subject at risk of a disease or disorder, or prescribing a therapeutic regimen or predicting benefit from therapy in a subject having a disease or disorder, the kit comprising: a) a solid support comprising capture agents associated therewith, wherein at least one capture agent selectively binds to a CD171 membrane marker on exosomes; and b) at least two detection agents, wherein at least one detection agent selectively binds to phosphorylated tau T181 and at least one detection agent selectively binds to neurogranin on the surface of the exosomes. In certain embodiments, at least one capture agent or detection agent comprises an antibody, an antibody fragment, an antibody mimetic, or an aptamer that specifically binds to CD171, phosphorylated tau T181, or neurogranin. In certain embodiments, the antibody is selected from the group consisting of a monoclonal antibody, a polyclonal antibody, a chimeric antibody, a nanobody, a recombinant fragment of an antibody, an Fab fragment, an Fab' fragment, an F(ab')$_2$ fragment, an Fv fragment, and an scFv fragment. In another embodiment, the kit comprises an anti-neurogranin antibody, an anti-phosphorylated tau T181 antibody, and an anti-CD171 antibody. In one embodiment, the disease or disorder is a neurological disorder, an immunological disorder, a placental disease, or cancer.

In some embodiments, the invention provides a method of prognosing or monitoring the progression of a disease or disorder in a subject, the method comprising: a) obtaining a biological sample comprising vesicles or exosomes from the subject; b) contacting a solid support comprising capture agents associated therewith with the biological sample under conditions wherein the capture agents selectively bind to a first biomarker on the vesicles or exosomes, wherein vesicles or exosomes are captured on the solid support; c) separating the solid support from the biological sample; d) measuring a level of a second biomarker protein on the vesicles or exosomes captured on the solid support, wherein the vesicles or exosomes are not lysed or permeabilized, thereby prognosing or monitoring the progression of the disease or disorder in the subject. In other embodiments, the method further comprises repeating (a), (b), (c), and (d) at a second time point with a second biological sample wherein an increase in the levels of the second biomarker relative to its level at the first time point indicates that the disease or disorder is progressing, and a decrease in the level of the second biomarker relative to its level at the first time point indicates that the disease or disorder is regressing. In other embodiments, the methods further comprise treating the subject for the disease or disorder if the disease or disorder is progressing. In still other embodiments, the method further comprises reducing treatment or stopping treatment for the disease or disorder if the disease or disorder is regressing. In some embodiment, the disease or disorder is a neurological disorder, an immunological disorder, a placental disease, or cancer. In other embodiments, the neurological disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), stroke, depression, bipolar disease, epilepsy, autism, schizophrenia, brain tumor, white matter disease, brain atrophy, mental retardation, cerebellar ataxia, multiple system atrophy, concussion, subconcussive impacts, and Parkinson's disease.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting.

BRIEF DESCRIPTION OF THE DRAWINGS

FIGS. 1A and 1B shows methods for quantifying cell-specific biomarkers of exosomes. FIG. 1A shows a schematic depicting the generation of exosomes containing proteins of the cell from which they originated (mother cell). FIG. 1B shows methods of screening exosomes for membrane markers and adsorbed markers.

FIG. 5A shows the detection of the membrane proteins, CD81 and CD171, and the non-membrane proteins, GAPDH and CTSD. FIG. 5B shows the detection of the membrane proteins, CD63, and SNAP25. FIG. 5C shows the detection of the non-membrane proteins, NRGN, MBP, GFAP, tau, T181, and ABETA42.

(FIG. 6D) NRGN, and (FIG. 6E) p-tau T181 were used as detection antibodies.

FIGS. 7A-7L show the stability of plasma levels of various exosome biomarkers of the present invention. Anti-CD81, anti-CD171, anti-SNAP25, anti-EAAT1, and anti-OMG were immobilized to ELISA plate. EDTA plasma was obtained from 7 control subjects every week for 2-3 weeks, and applied to ELISA wells. FIG. 7A shows assay schematic for detecting exosome membrane targets. FIGS. 7B-7F show detection with (FIG. 7B) the anti-CD81 probe on the CD81 plate for total exosome (TE), (FIG. 7C) the anti-CD171 probe on the CD81 plate for CD171-based NDE (cNDE), (FIG. 7D) the anti-SNAP25 probe on the CD81 plate for SNAP25-based NDE (sNDE), (FIG. 7E) the anti-CD81 probe on the EAAT1 plate (ADE), and (FIG. 7F) the anti-CD81 probe on the OMG plate for ODE. FIG. 7G shows assay schematic for exosome surface protein targets. FIGS. 7H-7L show detection with (FIG. 7H) the GFAP probe on the EAAT1 plate, (FIG. 7I) the MBP probe on the OMG plate, (FIG. 7J) the NRGN probe on the SNAP25 plate, (FIG. 7K) the tau probe on the SNAP25 plate, and (FIG. 7L) the NRGN probe on the CD171 plate, respectively.

FIG. 8A shows an exemplary assay schematic. FIG. 8B shows the assay results. Anti-NRGN (medium gray and dark gray columns) or control mouse IgG (black and light gray columns) were immobilized on an ELISA plate. EDTA plasma (light gray and dark gray columns) or PBS alone (black and medium gray columns) were applied to ELISA wells. Antibodies against NRGN, CD171, SNAP25, CD81, EAAT1, OMG and PBS control were used as detection antibodies.

FIG. 9A shows an assay schematic. FIGS. 9B-9D show the assay results. Anti-CD11b (medium gray and dark gray columns) or control mouse IgG (black and light gray columns) were immobi-lized to ELISA plate. EDTA plasma from 7 different donors (IR1-IR7) (light gray and dark gray columns) or PBS alone (black and medium gray columns) were applied to ELISA wells. Antibodies against GFAP (FIG. 9B), MBP (FIG. 9C), or NRGN (FIG. 9D) were used as detection antibodies FIGS. 10A-10F set forth data showing detection of secre-tory proteins (cytokines (IL1b and IL34) and chemokines (CX3CL1)) on the surface of brain-derived exosomes.

Figures 22A, 22B, 22C:
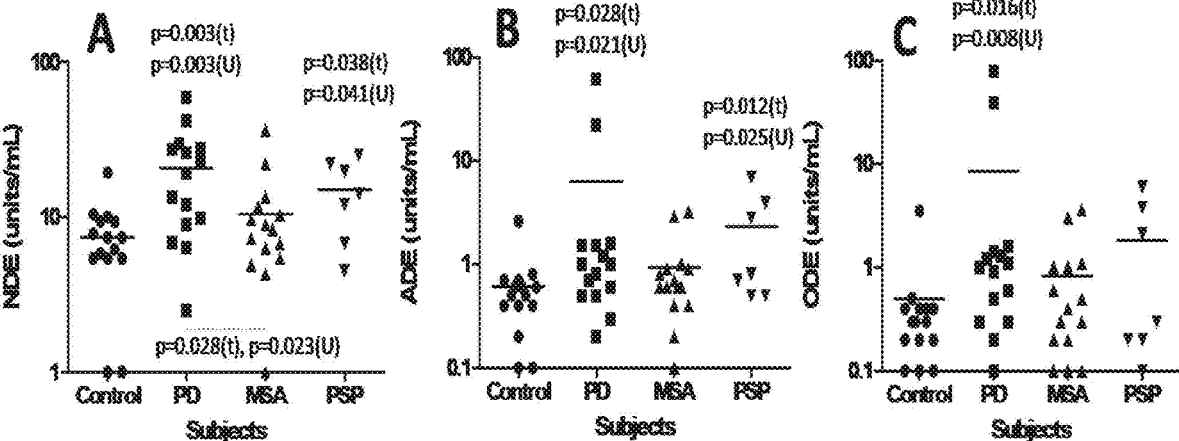

FIGS. 22A-22C set forth data showing enumeration of brain-derived exosomes in human subjects with Parkinson's Disease. NDE (A), ADE (B), and ODE (C) were enumerated in 15 each of control, PD, MSA, and 7 PSP patients. Each dot represents a single individual, and p values were against controls.

Figures 23A, 23B, 23C:
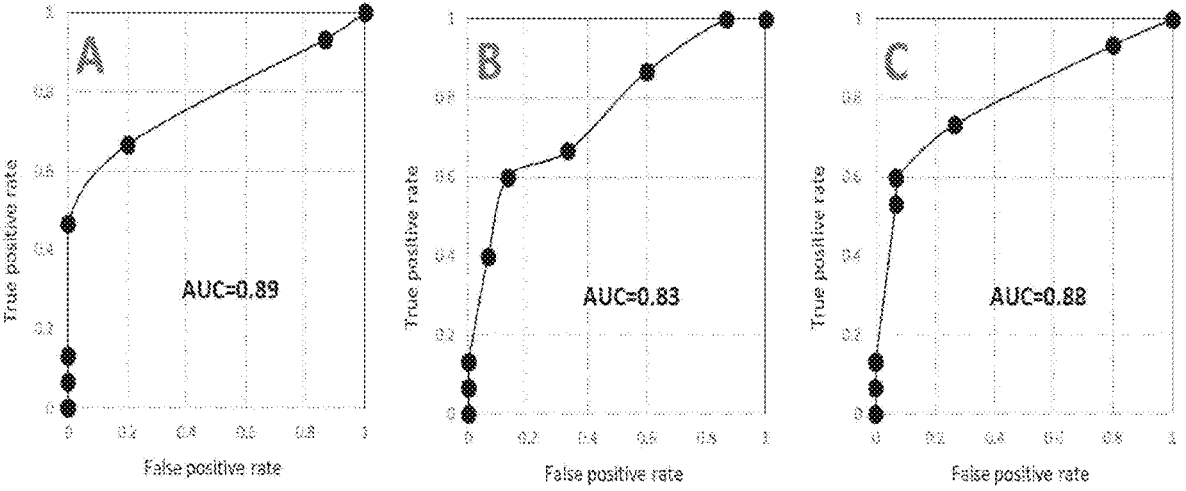
Figures 24A, 24B, 24C, 24D, 24E, 24F:
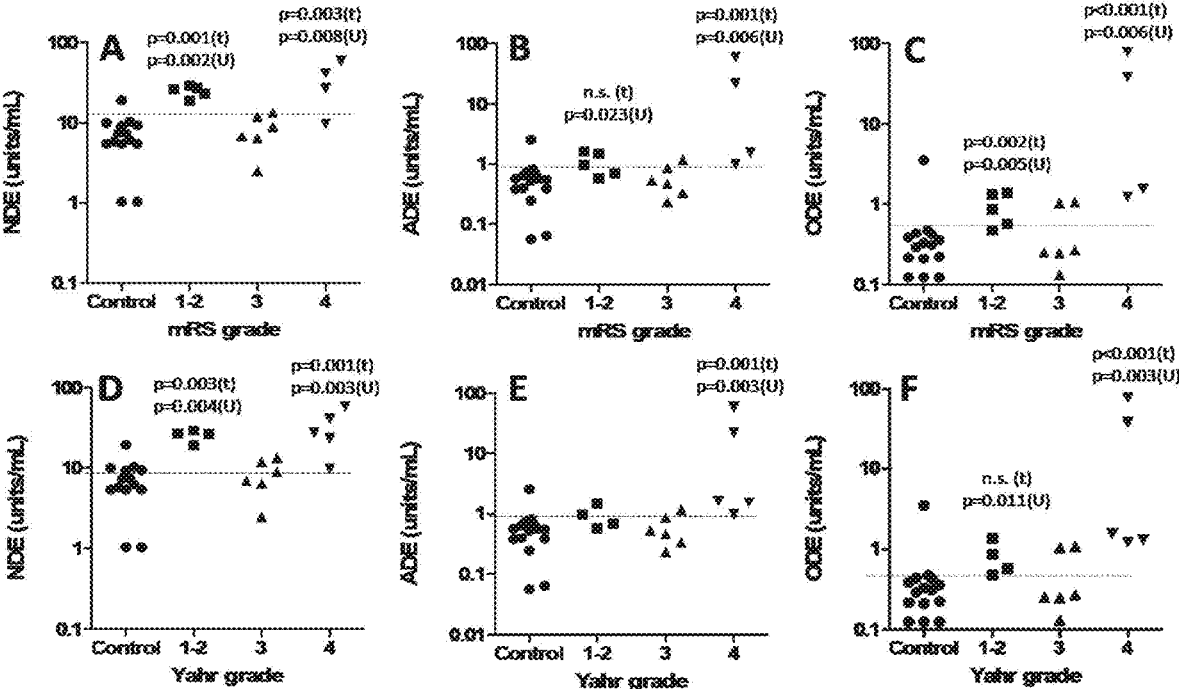
Figures 25A, 25B, 25C, 25D:
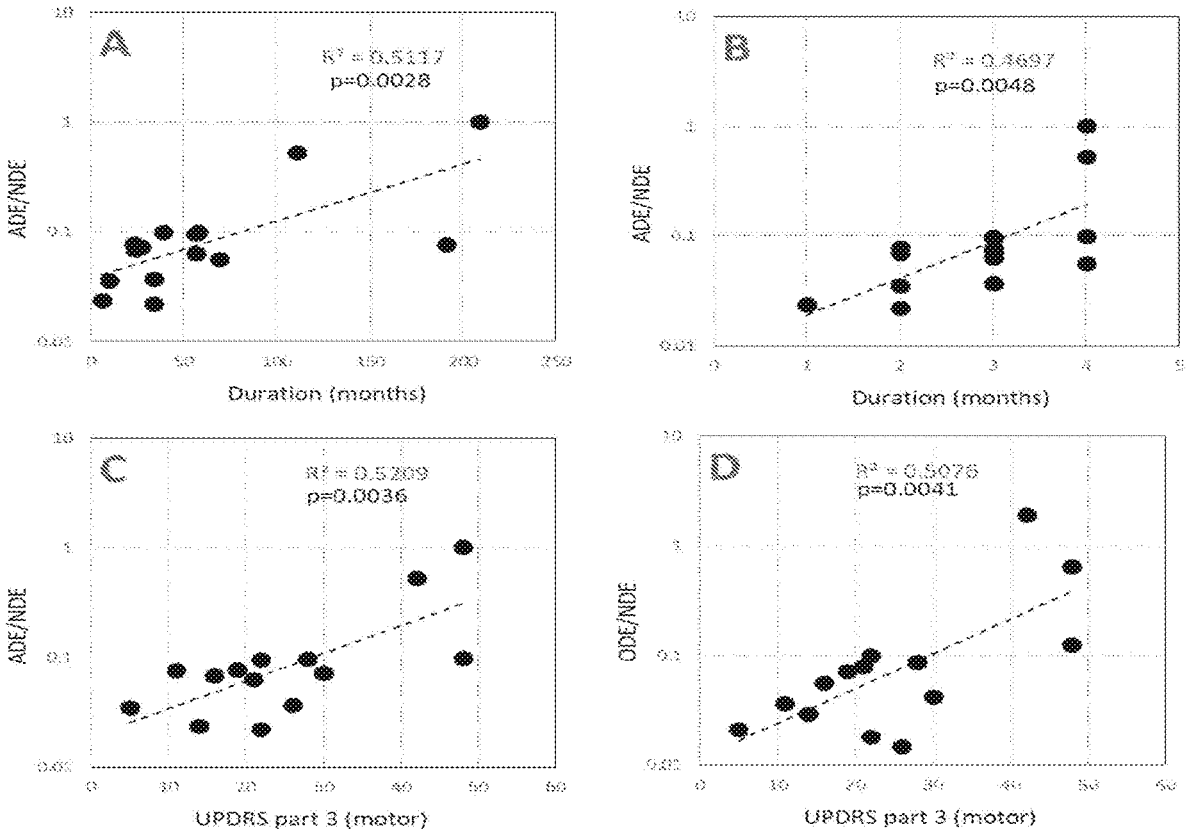
Figures 26A, 26B, 26C, 26D:
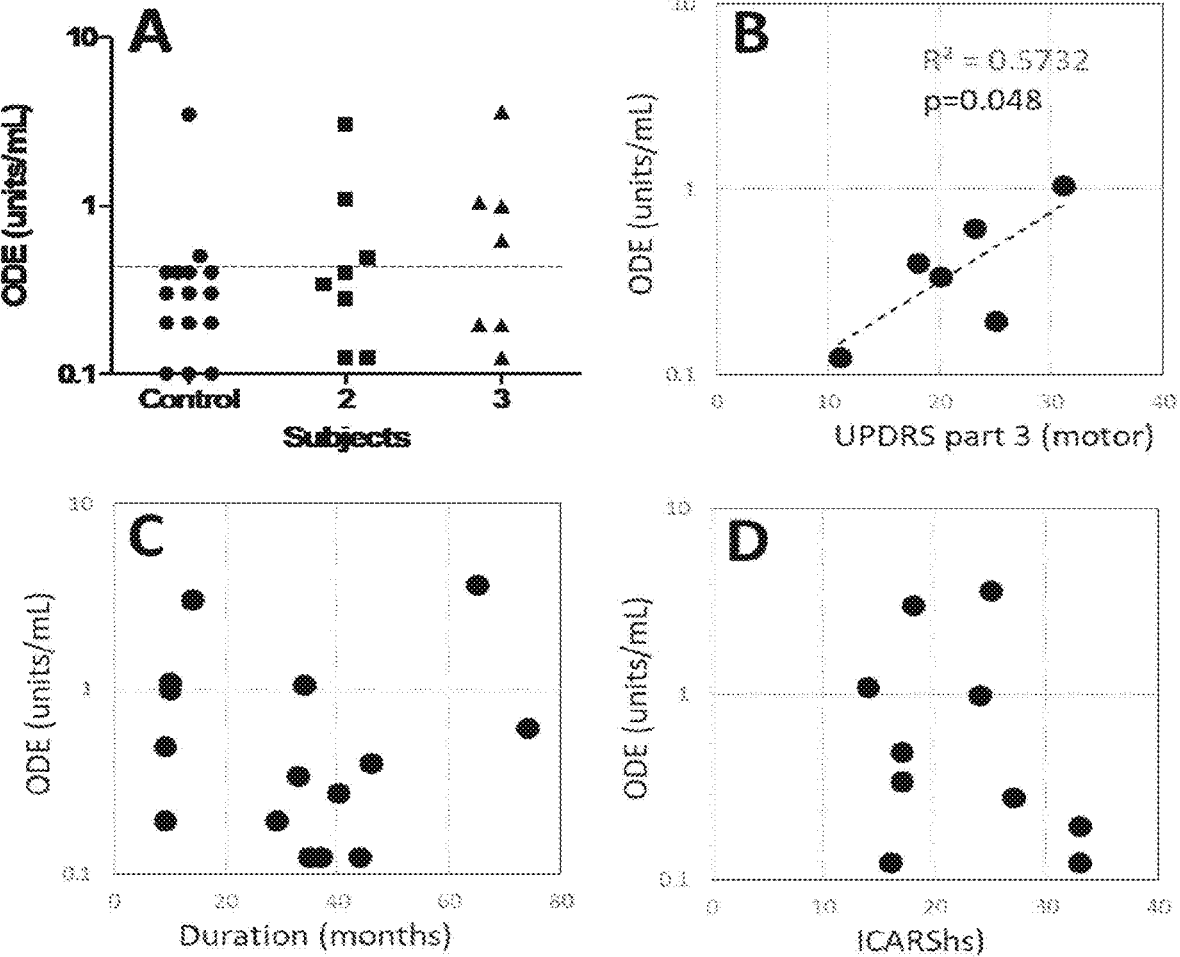
Figures 27A, 27B, 27C, 27D, 27E, 27F:
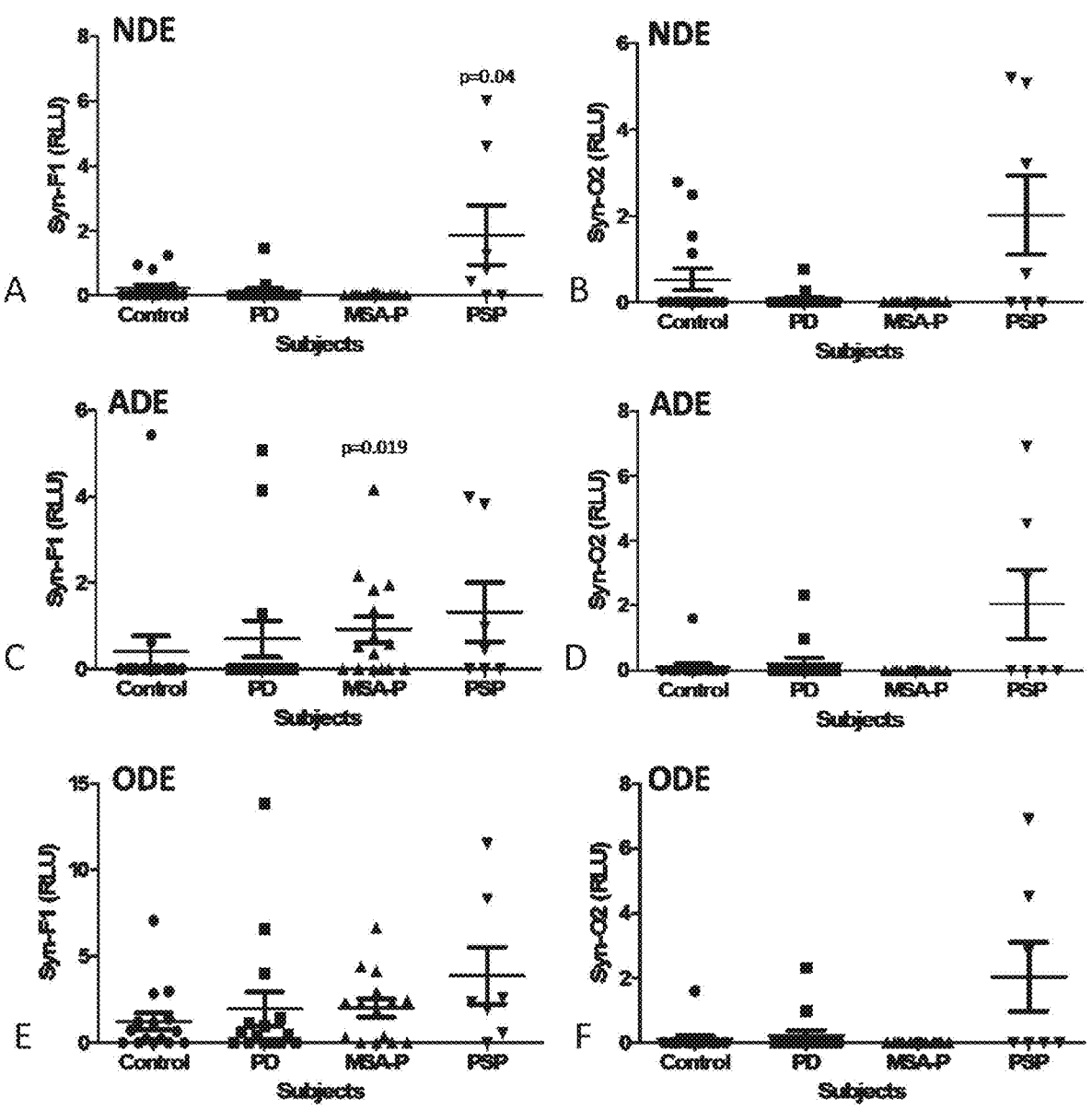

FIGS. 23A-23C set forth data showing Receiver Operat-ing Characteristic (ROC) of NDE and ODE for the differ-ential diagnosis of Parkinson's Disease and controls. ROC was calculated using NDE (A) and ODE (B) data of Par-kinson's Disease and control. Area under curve (AUC) was 88.9% and 88% for NDE and ODE, respectively.

FIGS. 24A-24F set forth data showing the correlation between the levels of plasma BDE and disease severity in plasma samples from subjects with Parkinson's Disease. NDE (A, D), ADE (B, E), and ODE (C, F) of PD patients were classified with the severity scores of mRS (A-C) and Hoehn-Yahr (D-F) and shown with those of controls. Each dot represents a single individual, and statistical p-values were between each severity group and control.

FIGS. 25A-25D set forth data showing correlation of Brain-Derived Exosomes and Parkinson's Disease severity. A: ADE/NDE ratio and disease duration. B: ADE/NDE ratio and mRS score. C: ADE/NDE ratio and UPDRS part 3 (motor). D: ODE/NDE ratio and UPDRS part 3 (motor).

Figure 3A:
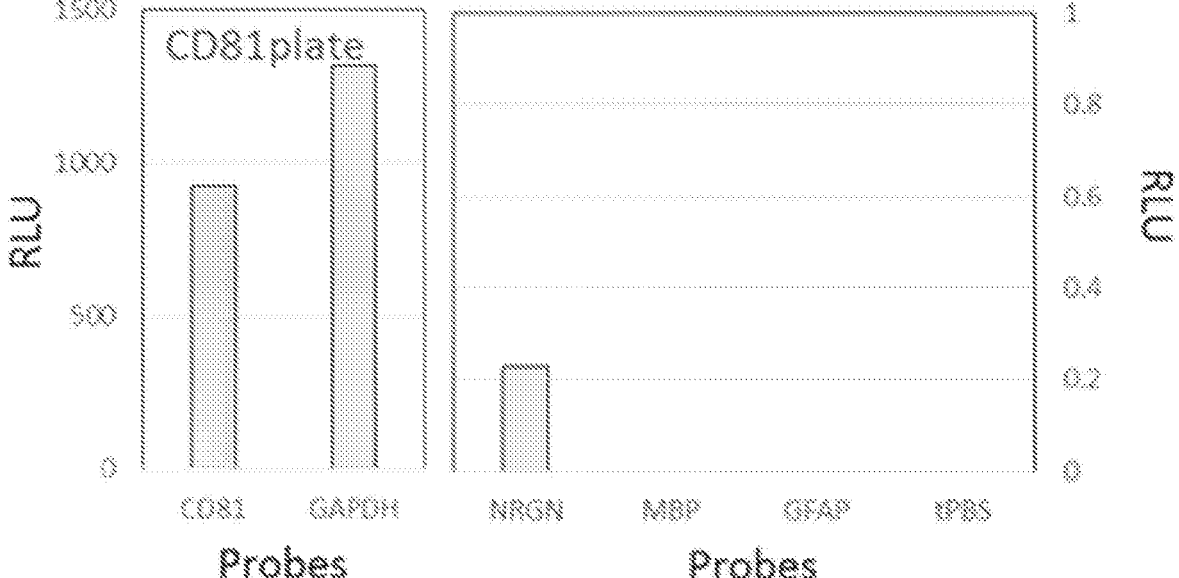
FIGS. 3A-3D show the specificity of marker proteins of the present invention. Antibodies against (FIG. 3A) the exosome surface marker CD81, (FIG. 3B) neuron surface marker SNAP25, (FIG. 3C) astrocyte surface marker (EAAT1), or (FIG. 3D) oligodendrocyte surface marker (OMG) were immobilized onto white ELISA plates. Ten uL of plasma suspended in 40 uL of PBS were applied to the ELISA plates. After overnight incubation at 4° C., unbound materials were removed. Biotin-labeled antibodies against the exosome surface marker CD81, general cytosolic marker GAPDH, cytosolic proteins in neuron (NRGN), oligodendrocyte (MBP), and astrocyte (GFAP) were applied to the ELISA plates. A no antibody control (tPBS) was also included. Conventional chemiluminescent ELISA was carried out, and the relative light unit (RLU) was determined.
Figure 3B:
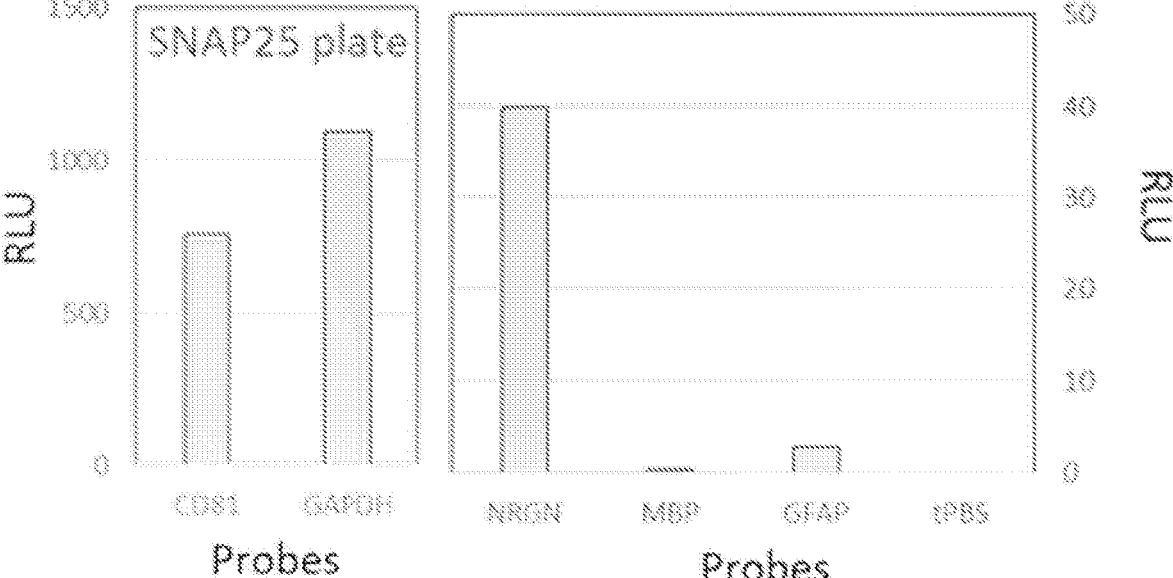
Figure 3C:
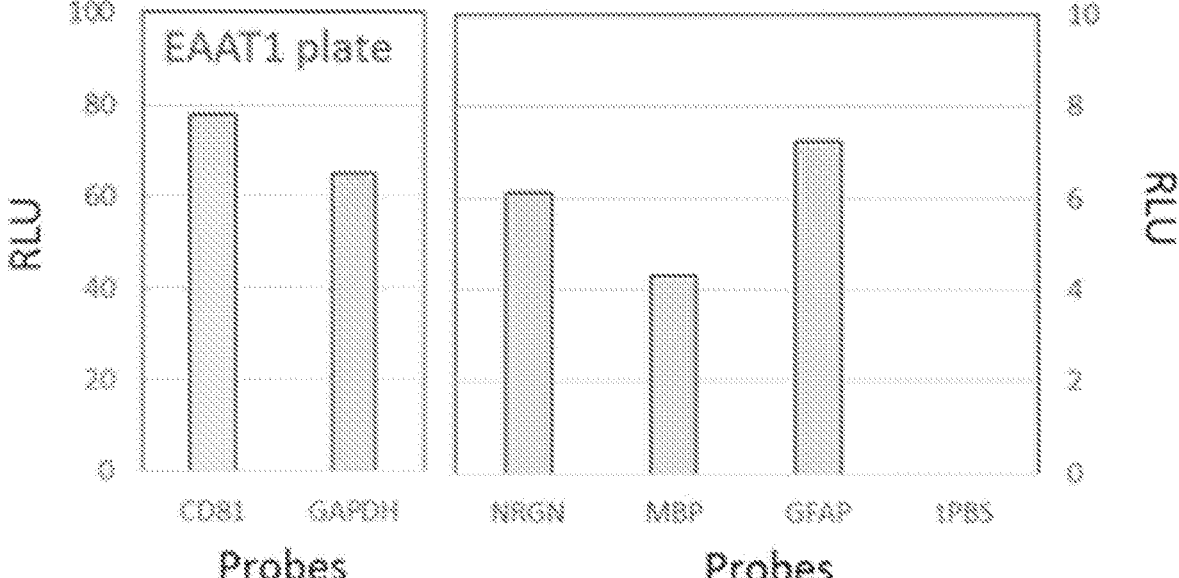
Figure 3D:
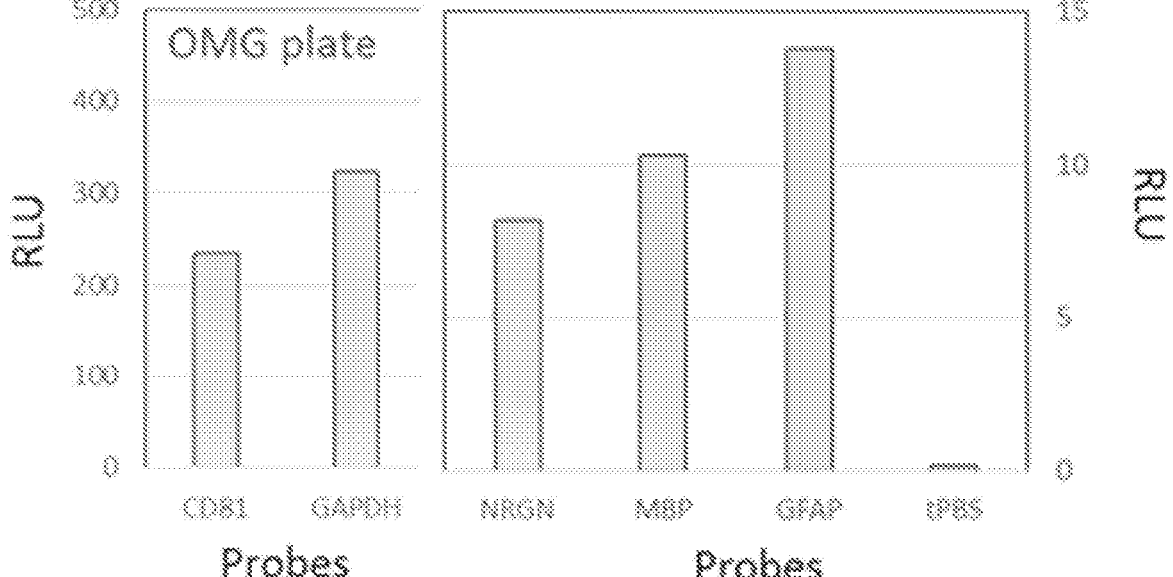

FIGS. 26A-26D set forth data showing correlation between the levels of plasma BDE and disease severity in MSA. A: ODE (A) of MSA patients was classified with the severity scores of mRS and shown with those of controls. Each dot represents a single individual. B: Same data as shown in FIG. 3C. C-E: ODE of each MSA patient was compared with disease duration in months (C), and scores of International Cooperative Ataxia Rating Scale (ICARS) (D) and Unified Parkinson's Disease Rating Scale (UPDRS) 3 (motor) (E). The $r^2$ and p values were shown in E.

FIGS. 27A-27F set forth data showing detection of patho-logical form of a-synuclein on the surface of neuron-, astrocyte-, and oligodendrocyte-derived exosomes.

Figure 28A:
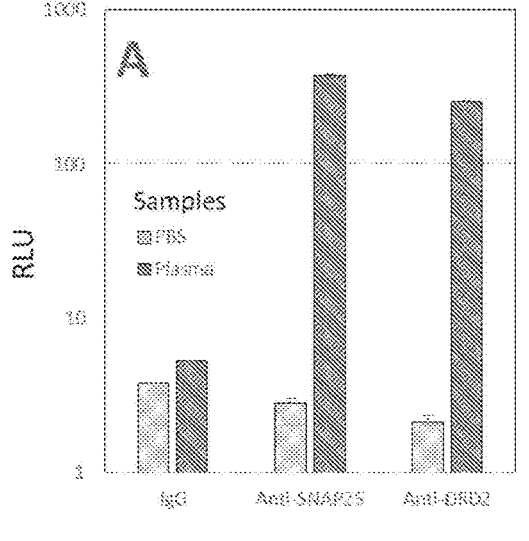
Figure 28B:
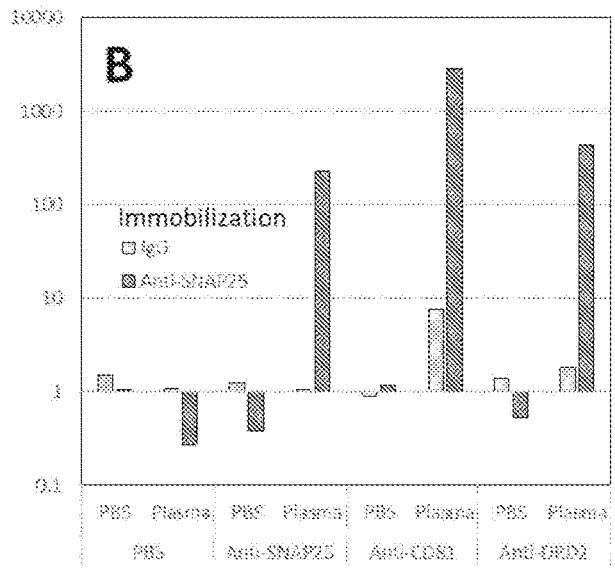

FIGS. 28A-28B set forth data showing detection of dop-amine receptor D2 (DRD2) on the surface of neuron-derived exosomes (NDE).

Figures 29A, 29B, 29C:
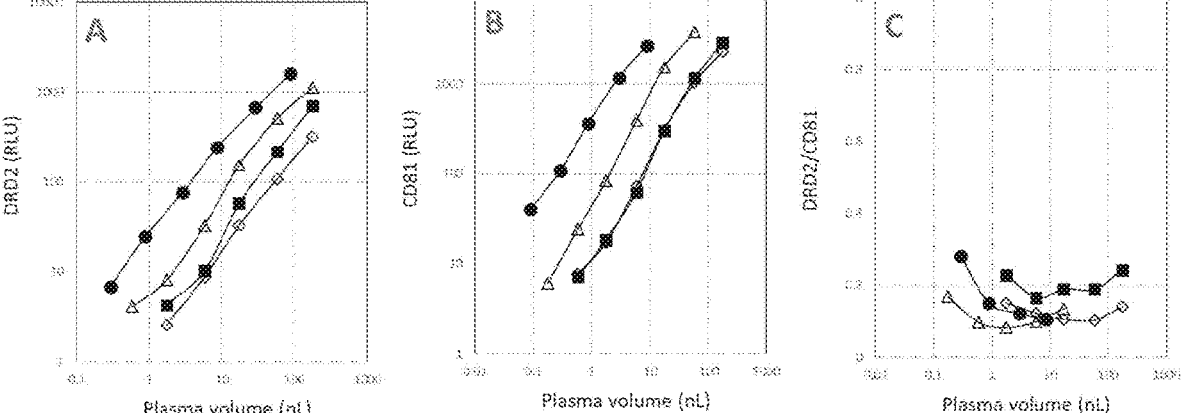
Figures 30A, 30B, 30C, 30D, 30E, 30F, 30G:
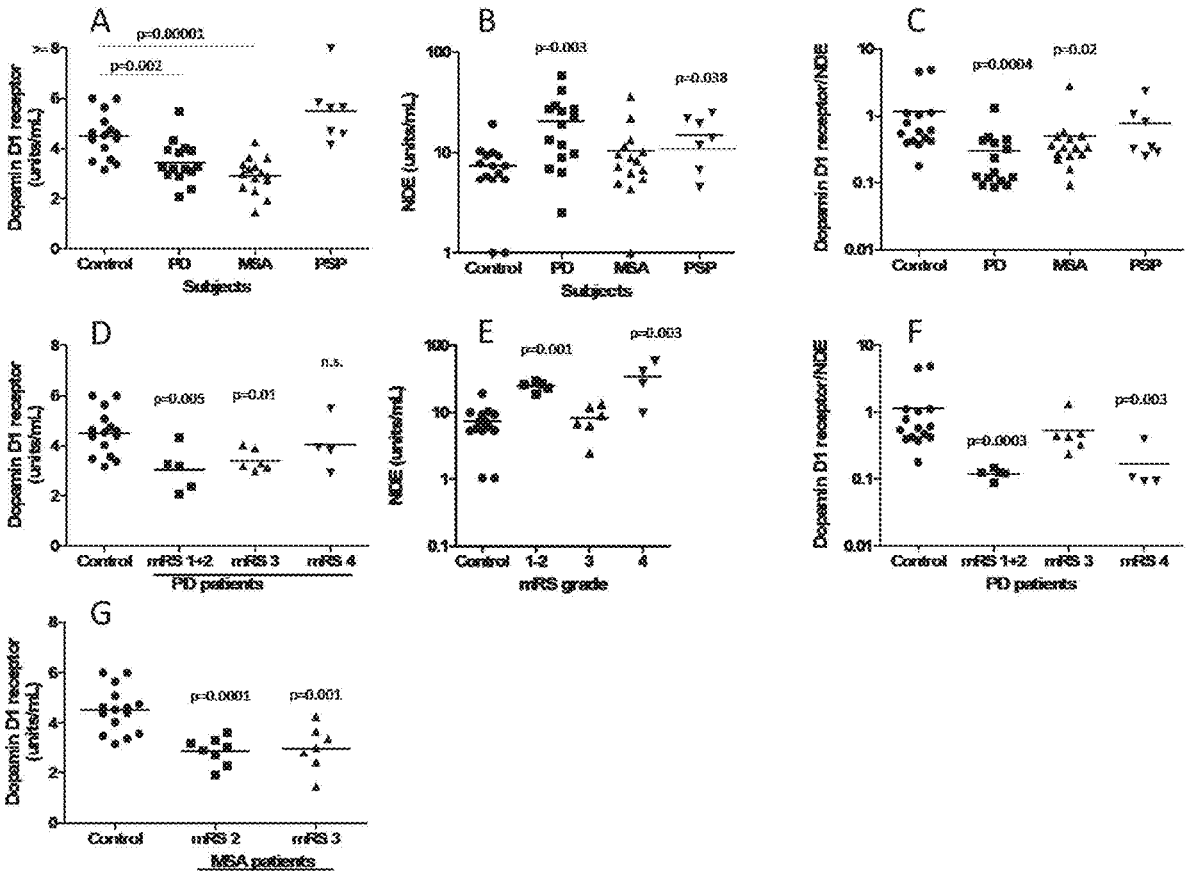

FIGS. 29A-29C set forth data showing plasma dilution study results for DRD2.

FIGS. 30A-30G set forth data showing DRD2 detection in neuron-derived exosomes in plasma samples from humans with neurological disease.

Figure 31:
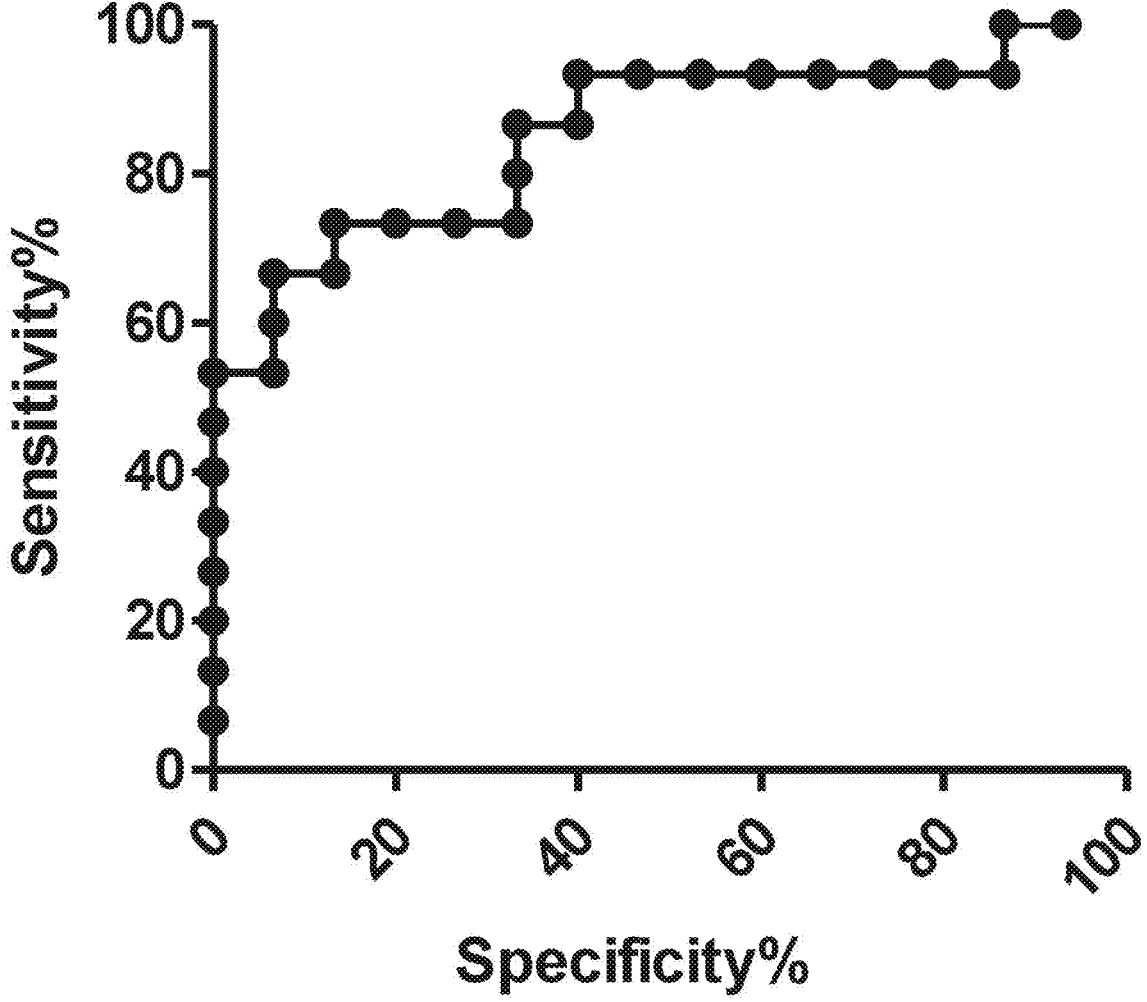

FIG. 31 sets forth data showing ROC curve and area under the curve (AUC) for DRD2 levels between PD and control samples.

FIGS. 32A-32D set forth data showing detection of CD81, SNCA, SNCA oligomer F1, and TH on the surface of DAT+ vesicles.

Figure 33:
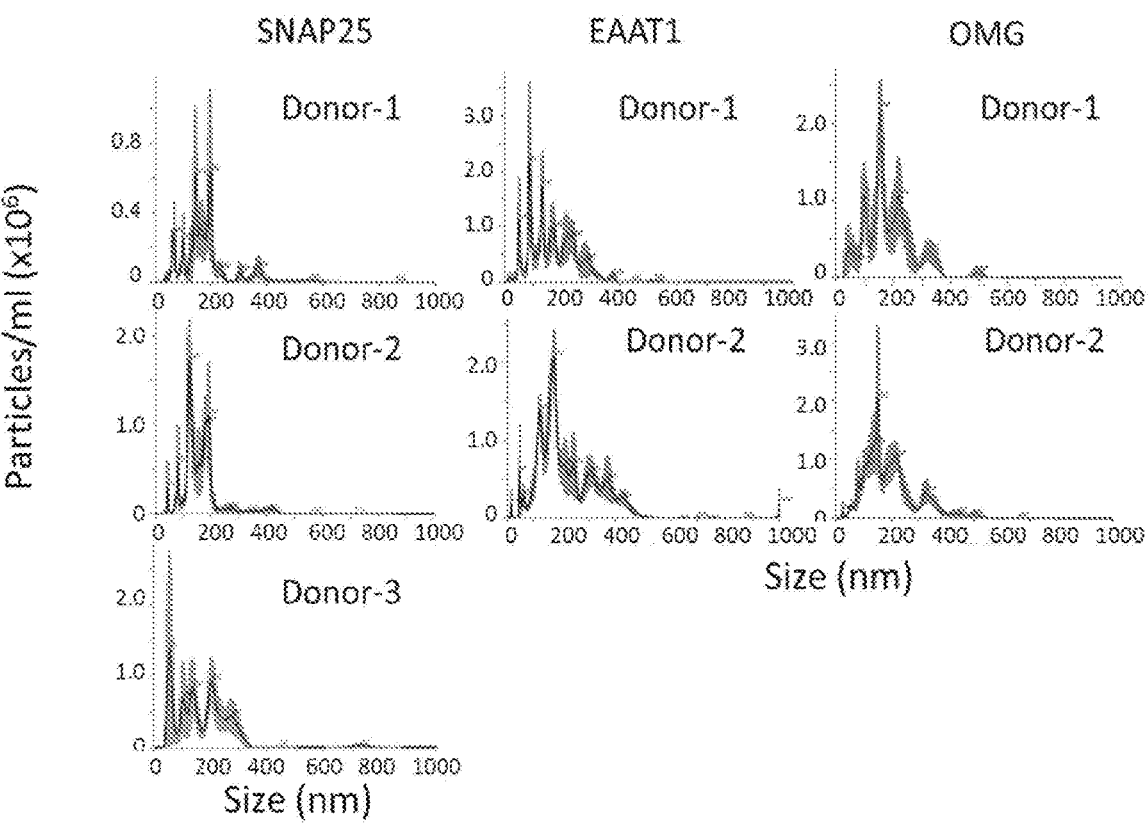

FIG. 33 sets forth data showing detection of SNAP25, EAAT1, and OMG on the surface of vesicles in plasma.

Figure 34:
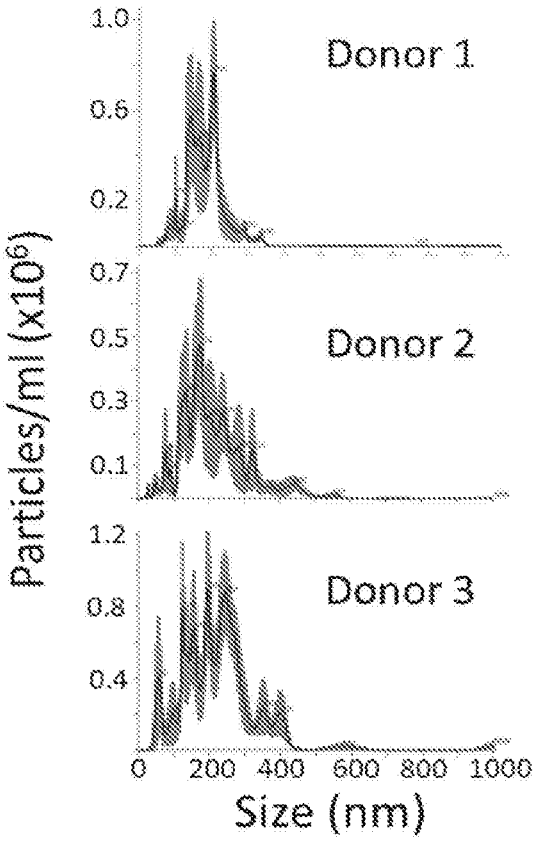

FIG. 34 sets forth data showing particle size for captured DAT+CD81+ vesicles in plasma.

Figure 35:
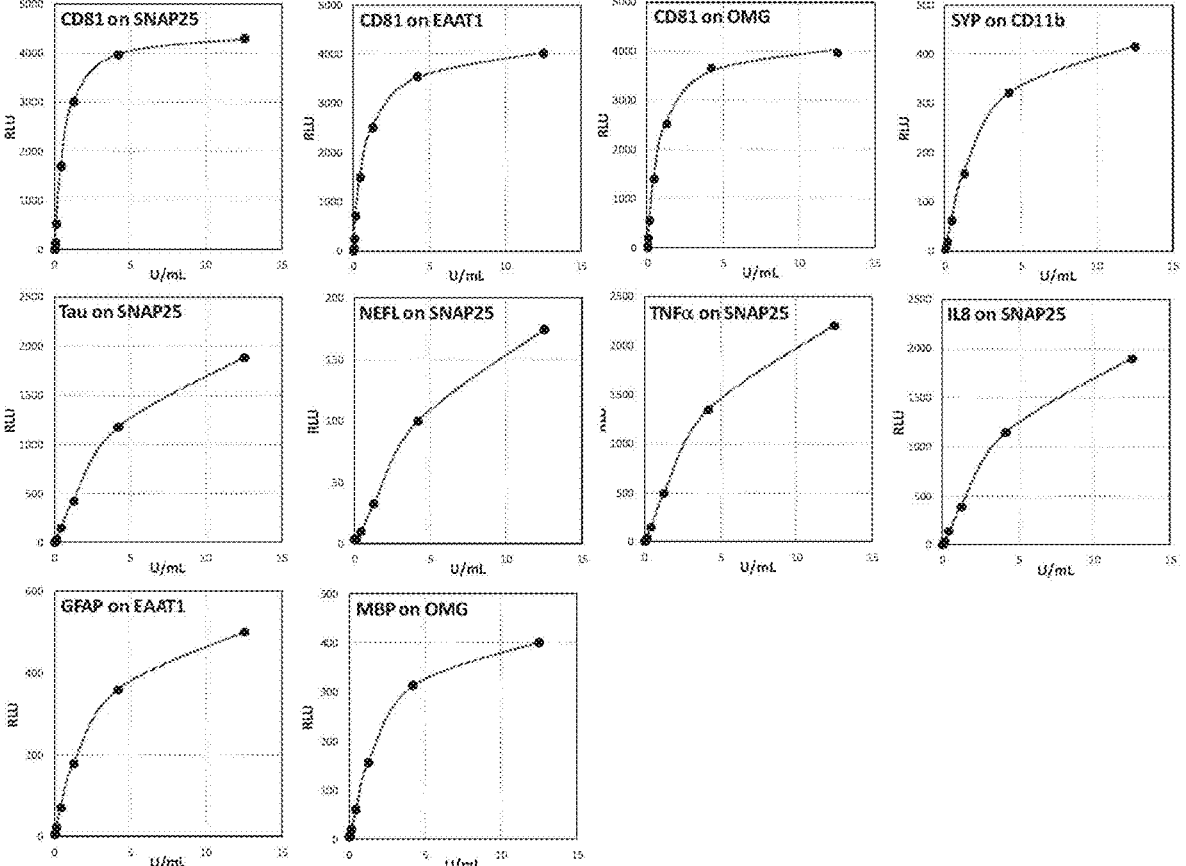

FIG. 35 sets forth data showing detection of various biomarkers on the surface of vesicles in plasma.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the development of an efficient method for detecting and quantitating biomarkers on vesicles. In particular, vesicles are selectively captured on a solid support, and membrane-bound and adsorbed biomarkers on the captured vesicles are detected without lysis or permeabilization of the vesicles. The invention further relates to the use of such biomarkers identified on vesicles in diagnostic and prognostic methods for various diseases.

Additionally, the present invention provides compositions for use in the methods described herein. Such compositions may include a solid support, capture agents which specifically bind to a surface marker (i.e., membrane protein or adsorbed protein) on vesicles to capture vesicles on the solid support, detection agents that specifically bind to biomarkers on vesicles, reagents for performing immunoassays, and other reagents for performing the methods described herein.

The present invention further provides kits for detecting biomarkers on vesicles. The kits may comprise a solid support, one or more capture agents which specifically bind and capture vesicles on the solid support, one or more detection agents which specifically bind a biomarker on vesicles, and optionally, immunoassay reagents and other reagents for performing the methods described herein, one or more containers for collecting and or holding the biological sample, and instructions for using the kits.

The present invention further relates to the discovery that exosomal biomarkers can be assayed to identify subjects having or likely to develop neurological disorders, including, for example, Alzheimer's disease (AD), multiple sclerosis (MS), and frontotemporal dementia (FTD).

The present invention is based, in part, on the discovery of unexpected decreases or increases in certain biomarkers in neuron-derived exosomes present in the circulation of subjects having neurological disease (e.g., Alzheimer's disease). The present invention demonstrates that exosomal levels of these biomarkers may be assayed to diagnose a neurological disorder in a subject having a neurological disease. The present invention further shows that measurement of certain biomarkers in neuron-derived exosomes from a subject may be used to predict the subsequent development of a neurological disease (e.g., identify a subject at risk of developing a neurological disorder).

The section headings are used herein for organizational purposes only, and are not to be construed as in any way limiting the subject matter described herein.

Biological Sample

A biological sample comprising vesicles (e.g., exosomes) may be obtained from a subject. The biological sample obtained from the subject is typically blood, but can be any sample from bodily fluids, tissue or cells comprising the vesicles to be analyzed. The biological sample may include, but is not limited to, whole blood, serum, plasma, urine, interstitial fluid, peritoneal fluid, cerebrospinal fluid, a cervical swab, tears, saliva, a buccal swab, skin, organs, and biopsies. Alternatively, exosomes can be obtained from cultured cells by collection of secreted exosomes from the surrounding culture media.

In some embodiments, the biological sample of the invention is obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of vesicles (e.g., exosomes) present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Enrichment or Isolation of Vesicles (Exosomes, Microparticles, Microvesicles, Nanosomes, Extracellular Vesicles, and Ectosomes)

Samples can be enriched for vesicles through positive selection, negative selection, or a combination of positive and negative selection. In some embodiments, vesicles are directly captured. In other embodiments, blood cells are captured and vesicles are collected from the remaining biological samples. In some embodiments, the vesicles enriched in the biological samples are exosomes, microparticles, microvesicles, nanosomes, extracellular vesicles, or ectosomes. In some embodiments, the vesicles enriched in the biological samples are neuron-derived exosomes, astrocyte-derived exosomes, oligodendrocyte-derived exosomes, or microglia-derived exosomes.

Samples can also be enriched for vesicles based on differences in the biochemical properties of vesicles. For example, samples can be enriched for vesicles based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used. In some of the embodiments based on metabolic differences, dye uptake/exclusion measured by flow cytometry or another sorting technology is used. In some of the embodiments based on gene expression, cell culture with cytokines is used. Samples can also be enriched for vesicles based on other biochemical properties known in the art. For example, samples can be enriched for vesicles based on pH or motility. Further, in some embodiments, more than one method is used to enrich for vesicles. In other embodiments, samples are enriched for vesicles using antibodies, ligands, or soluble receptors.

In other embodiments, surface markers are used to positively enrich vesicles in the sample. In some embodiments, the vesicles are exosomes, microparticles, microvesicles, nanosomes, extracellular vesicles, or ectosomes. In other embodiments, NCAM, CD171, CD9, CD63, CD81, SNAP25, EAAT1, OMG, neuron-specific enolase, diverse neuron or astrocyte adhesive proteins, microglial CD18/11, or CD3 T cell membrane cell surface markers are used to enrich for exosomes. In some embodiments, cell surface markers that are not found on vesicles populations are used to negatively enrich vesicles by depleting cell populations. Flow cytometry sorting may also be used to further enrich for exosomes using cell surface markers or intracellular or extracellular markers conjugated to fluorescent labels. Intracellular and extracellular markers may include nuclear stains or antibodies against intracellular or extracellular proteins preferentially expressed in vesicles. Cell surface markers may include antibodies against cell surface antigens that are preferentially expressed on exosomes (e.g., NCAM). In some embodiments, the cell surface marker is a neuron-derived exosome surface marker, including, for example, NCAM or CD171. In some embodiments, a monoclonal NCAM, CD9, CD63, CD81, neuron-specific enolase or CD171 antibody is used to enrich or isolate exosomes from the sample. In certain aspects, the NCAM, CD9, CD63, CD81, neuron-specific enolase or CD171 antibody is biotinylated. In this embodiment, biotinylated NCAM or CD171 antibody can form an antibody-exosome complex that can be subsequently isolated using streptavidin-agarose resin or beads. In other embodiments, the NCAM, CD9, CD63, CD81, neuron-specific enolase or CD171 antibody is a monoclonal anti-human NCAM, CD9, CD63, CD81, neuron-specific enolase or CD171 antibody. In other embodiments, the cell surface marker is a neuron-specific protein (e.g., synaptosome associated protein 25 (SNAP25), neurogranin (NRGN), tau, phosphorylated tau, αβ-42, and synaptophysin), an astrocyte-specific protein (e.g., glial fibrillary acidic protein (GFAP) and excitatory amino acid transporter 1 (EAAT1)), a microglia-specific protein (CD11b), an oligodendrocyte-specific protein (e.g., myelin basic protein (MBP), an oligodendrocyte myelin glycoprotein (OMG), a cytosolic protein (e.g., glyceraldehyde-3-phosphate dehydrogenase (GAPDH), alpha-synuclein (SNCA), cathepsin D (CTSD), AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, PSG1, or FasL), or a chemokine (CX3CL1) or cytokine (IL1b, IL34, FasL, or IL12B).

In some embodiments, enriched vesicles from the biological sample are subsequently enriched for a specific type of vesicle. For example, the biological sample is enriched for exosomes and then the enriched exosomes are subsequently enriched for neural-derived exosomes. In some embodiments, the biological sample is enriched for individual neural cell sources of vesicles. In certain aspects, the neural cell sources of vesicles are microglia, neurons, or astrocytes.

In other embodiments, vesicles are isolated or enriched from a biological sample by a method comprising: contacting a biological sample with an agent under conditions wherein a vesicle present in said biological sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In certain embodiments, the agent is an antibody or a lectin. Lectins useful for forming a vesicle-lectin complex are described in U.S. Patent Application Publication No. 2012/0077263. In some embodiments, the vesicle is an exosome, a microparticle, a microvesicle, nanosomes, extracellular vesicles, or an ectosome. In some embodiments, the exosomes are neuron-derived exosomes, astrocyte-derived exosomes, oligodendrocyte-derived exosomes, or microglia-derived exosomes. In some embodiments, multiple isolating or enriching steps are performed. In certain aspects of the present embodiment, a first isolating step is performed to isolate exosomes from a blood sample and a second isolating step is performed to isolate neural-derived exosomes from other exosomes.

In yet other embodiments, the methods further comprise releasing the vesicle from the vesicle-agent complex. In other embodiments, the vesicle is released by exposing the vesicle-agent complex to low pH between 3.5 and 1.5. In other embodiments, the vesicle is released using a competing peptide that competes for the binding of the selection antibody used in the methods of the present invention. In yet other embodiments, the released vesicle is neutralized by adding a high pH solution. In other embodiments, the released vesicle is lysed by incubating the released vesicles with a lysis solution. In still other embodiments, the lysis solution contains inhibitors for proteases and phosphatases. Capture and Detection of Vesicles on a Solid Support In other embodiments, a subset of vesicles is separated from other vesicles in a biological sample using capture agents immobilized on a solid support. Such capture agents bind selectively to a surface marker (e.g., membrane protein or adsorbed protein) on vesicles such that the capture agent can "capture" vesicles having the surface marker. By "capture" is meant that the target vesicle can be separated from other vesicles in the sample by virtue of the binding of the capture agent to the surface marker on the vesicle.

The specificity of the capture agent determines the subset of vesicles from a biological sample that are captured on the solid support. One or more capture agents can be used in combination in order to capture vesicles having different surface markers. For example, the solid support may comprise more than one type of capture agent associated therewith, for example, at least 2, 3, 4, 5, 6, 7, 8, 9, 10, 15, 20, or more different capture agents that selectively bind to different biomarkers on the vesicles. In some embodiments, the vesicles targeted by a capture agent are exosomes, microparticles, microvesicles, nanosomes, extracellular vesicles, or ectosomes.

In some embodiments, the capture agent selectively binds to neuron-derived exosomes, astrocyte-derived exosomes, oligodendrocyte-derived exosomes, or microglia-derived exosomes. For example, a capture agent can be chosen that selectively binds to an exosome surface marker (e.g., CD81) to capture exosomes generally, a neuron-specific protein (e.g., synaptosome associated protein 25 (SNAP25), neurogranin (NRGN), tau, phosphorylated tau, $\alpha\beta$-42, and synaptophysin) to capture neuron-derived exosomes, an astrocyte-specific protein (e.g., glial fibrillary acidic protein (GFAP) and excitatory amino acid transporter 1 (EAAT1) to capture astrocyte-derived exosomes, a microglia-specific protein (CD11b) to capture microglia-derived exosomes, an oligodendrocyte-specific protein (e.g., myelin basic protein (MBP) or oligodendrocyte myelin glycoprotein (OMG)) to capture oligodendrocyte-derived exosomes, a cytosolic protein (e.g., glyceraldehyde-3-phosphate dehydrogenase (GAPDH), alpha-synuclein (SNCA) or cathepsin D (CTSD)), or an a chemokine (CX3CL1) or cytokine (IL1b, IL34, FasL, or IL12B) protein to capture a brain-derived exosome. In some embodiments, a capture agent can be chosen that selectively binds to an extracellular vesicle (EV) surface marker (e.g., DAT) to capture extracellular vesicles generally.

Typically, the capture agent is associated with a solid support, either directly or indirectly. Capture agents may be immobilized on the surface of a solid support, such as, but not limited to, a plate, slide, wafer, non-magnetic bead, magnetic bead, rod, particle, strand, disc, membrane, film, or the inner surface of a tube, channel, column, flow cell device, or microfluidic device. A solid support may comprise various materials, including, but not limited to glass, quartz, silicon, metal, ceramic, plastic, nylon, polyacrylamide, agarose, resin, porous polymer monoliths, hydrogels, and composites thereof. Additionally, a substrate may be added to the surface of a solid support to facilitate attachment of a capture agent.

Once captured on the solid support, the vesicles can be screened for one or more membrane-bound and adsorbed biomarkers using detection agents without the need for lysis or permeabilization of the vesicles. Such detection agents bind selectively to membrane-bound or adsorbed biomarkers on the vesicles. In certain embodiments, the detection agent selectively binds to a neuron-specific protein (e.g., synaptosome associated protein 25 (SNAP25), neurogranin (NRGN), $\alpha\beta$-42, tau, phosphorylated tau, and synaptophysin), an astrocyte-specific protein (e.g., glial fibrillary acidic protein (GFAP) and excitatory amino acid transporter 1 (EAAT1)), a microglia-specific protein (CD11b), an oligodendrocyte-specific protein (e.g., myelin basic protein (MBP), an oligodendrocyte myelin glycoprotein (OMG), a cytosolic protein (e.g., glyceraldehyde-3-phosphate dehydrogenase (GAPDH), alpha-synuclein (SNCA), cathepsin D (CTSD), AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, PSG1, or FasL), a chemokine (CX3CL1) or cytokine (IL1b, IL34, FasL, or IL12B), CTSD, GAPDH, CD81, CD63, or CD171, AchE, LAMP1, REST, SYT, TH, SYP, SYNPO, PSD95, SV2A, CCL2, IL34, GYS, OR, DR6, HSP, IL12beta, AB, or BACE. In certain embodiments, detection of biomarkers on vesicles captured on the solid support comprises using more than one type of detection agent, for example, at least 2, 3, 4, 5, 6, 7, 8, 9, 10, 15, 20, or more different detection agents that selectively bind to different biomarkers on the vesicles.

Capture agents and detection agents may comprise, for example, antibodies, antibody fragments, antibody mimetics, or aptamers that specifically bind to a surface marker (e.g., membrane-bound or adsorbed protein) on a vesicle. The phrase "specifically (or selectively) binds" refers to a binding reaction that is determinative of the presence of the surface marker on a vesicle in a heterogeneous population of proteins and other biologics. Thus, under designated assay conditions, the specified capture agents or detection agents bind to a particular surface marker on a vesicle at least two times the background and do not substantially bind in a significant amount to other proteins present in the sample.

In certain embodiments, the capture agent or detection agent comprises an antibody that specifically binds to a surface marker (e.g., membrane protein or adsorbed protein) on a vesicle. Any type of antibody may be used, including polyclonal and monoclonal antibodies, hybrid antibodies, altered antibodies, chimeric antibodies and, humanized antibodies, as well as: hybrid (chimeric) antibody molecules (see, for example, Winter et al. (1991) *Nature* 349:293-299; and U.S. Pat. No. 4,816,567); F(ab')$_2$ and F(ab) fragments; Fv molecules (noncovalent heterodimers, see, for example, Inbar et al. (1972) *Proc Natl Acad Sci USA* 69:2659-2662; and Ehrlich et al. (1980) *Biochem* 19:4091-4096); single-chain Fv molecules (sFv) (see, e.g., Huston et al. (1988) *Proc Natl Acad Sci USA* 85:5879-5883); nanobodies or single-domain antibodies (sdAb) (see, e.g., Wang et al. (2016) *Int J Nanomedicine* 11:3287-3303, Vincke et al. (2012) *Methods Mol Biol* 911:15-26; dimeric and trimeric antibody fragment constructs; minibodies (see, e.g., Pack et al. (1992) *Biochem* 31:1579-1584; Cumber et al. (1992) J Immunology 149B:120-126); humanized antibody molecules (see, e.g., Riechmann et al. (1988) *Nature* 332:323-327; Verhoeyan et al. (1988) *Science* 239:1534-1536; and U.K. Patent Publication No. GB 2,276,169, published 21 Sep. 1994); and, any functional fragments obtained from such molecules, wherein such fragments retain specific-binding properties of the parent antibody molecule (i.e., specifically binds to a target surface marker on a vesicle).

In other embodiments, the capture agent or detection agent comprises an aptamer that specifically binds to the target surface marker on a vesicle. Any type of aptamer may be used, including a DNA, RNA, xeno-nucleic acid (XNA), or peptide aptamer that specifically binds to the target antibody isotype. Such aptamers can be identified, for example, by screening a combinatorial library. Nucleic acid aptamers (e.g., DNA or RNA aptamers) that bind selectively to a target antibody isotype can be produced by carrying out repeated rounds of in vitro selection or systematic evolution of ligands by exponential enrichment (SELEX). Peptide aptamers that bind to a target antibody isotype may be isolated from a combinatorial library and improved by directed mutation or repeated rounds of mutagenesis and selection. For a description of methods of producing aptamers, see, e.g., *Aptamers: Tools for Nanotherapy and Molecular Imaging* (R. N. Veedu ed., Pan Stanford, 2016), *Nucleic Acid and Peptide Aptamers: Methods and Protocols* (Methods in Molecular Biology, G. Mayer ed., Humana Press, 2009), *Nucleic Acid Aptamers: Selection, Characterization,*

*and Application* (Methods in Molecular Biology, G. Mayer ed., Humana Press, 2016), *Aptamers Selected by Cell-SELEX for Theranostics* (W. Tan, X. Fang eds., Springer, 2015), Cox et al. (2001) Bioorg. Med. Chem. 9(10):2525-2531; Cox et al. (2002) Nucleic Acids Res. 30(20): e108, Kenan et al. (1999) Methods Mol Biol. 118:217-231; Platella et al. (2016) Biochim. Biophys. Acta November 16 pii: S0304-4165(16)30447-0, and Lyu et al. (2016) Theranostics 6(9):1440-1452; herein incorporated by reference in their entireties.

In yet other embodiment, the capture agent or detection agent comprises an antibody mimetic. Any type of antibody mimetic may be used, including, but not limited to, affibody molecules (Nygren (2008) FEBS J. 275 (11):2668-2676), affilins (Ebersbach et al. (2007) J. Mol. Biol. 372 (1):172-185), affimers (Johnson et al. (2012) Anal. Chem. 84 (15): 6553-6560), affitins (Krehenbrink et al. (2008) J. Mol. Biol. 383 (5):1058-1068), alphabodies (Desmet et al. (2014) Nature Communications 5:5237), anticalins (Skerra (2008) FEBS J. 275 (11):2677-2683), avimers (Silverman et al. (2005) Nat. Biotechnol. 23 (12):1556-1561), darpins (Stumpp et al. (2008) Drug Discov. Today 13 (15-16):695-701), fynomers (Grabulovski et al. (2007) J. Biol. Chem. 282 (5):3196-3204), and monobodies (Koide et al. (2007) Methods Mol. Biol. 352:95-109).

Detection agents may further comprise a detectable label to facilitate detection and/or quantitation of biomarkers on vesicles. Detectable labels include fluorescent, chemiluminescent, electrochemiluminescent, or bioluminescent tags, metals, dyes, radionuclides, and the like, attached to the specific binding agent (e.g., antibody, antibody fragment, antibody mimetic, or aptamer that specifically binds to a membrane-bound or adsorbed biomarker on vesicles).

Neurological Disorders

The present invention provides methods for diagnosing or prognosing a neurological disorder in a subject, identifying a subject at risk of a neurological disorder, or prescribing a therapeutic regimen or predicting benefit from therapy in a subject having a neurological disorder. In some embodiments, the present invention provides methods for differential diagnosis of a neurological disorder in a subject.

In some embodiments the neurological disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), stroke, depression, bipolar disease, epilepsy, autism, schizophrenia, brain tumor, white matter disease, brain atrophy, mental retardation, cerebellar ataxia, concussion, subconcussive impacts, and Parkinson's disease.

In some embodiments, the present invention enables a medical practitioner to diagnose or prognose one or more neurological disorders in a subject. In other embodiments, the present invention enables a medical practitioner to rule out or eliminate one or more neurological diseases as a diagnostic possibility. In other embodiments, the methods of the present invention allow a medical practitioner to distinguish some forms of FTD from Alzheimer's disease. In yet other embodiments, the present invention enables a medical practitioner to identify a subject at risk of developing a neurological disorder. In other embodiments, the present invention enables a medical practitioner to predict whether a subject will later develop a neurological disorder. In further embodiments, the present invention enables a medical practitioner to prescribe a therapeutic regimen or predict benefit from therapy in a subject having a neurological disorder.

Cancer

The present invention provides methods for diagnosing or prognosing cancer in a subject, identifying a subject at risk of developing cancer, or prescribing a therapeutic regimen or predicting benefit from therapy in a subject having cancer. Generally, a cancer is characterized by the uncontrolled growth of abnormal cells anywhere in a body. The abnormal cells may be termed cancer cells, malignant cells, or tumor cells. Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer, bladder cancer, or pancreatic cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesotheliomia. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be a leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

In some embodiments, the present invention enables a medical practitioner to diagnose or prognose one or more cancers in a subject. In other embodiments, the present invention enables a medical practitioner to rule out or eliminate one or more cancers as a diagnostic possibility. In other embodiments, the methods of the present invention allow a medical practitioner to identify the origin of a cancer. In yet other embodiments, the present invention enables a medical practitioner to identify a subject at risk of developing cancer. In other embodiments, the present invention enables a medical practitioner to predict whether a subject will later develop cancer. In further embodiments, the present invention enables a medical practitioner to prescribe a therapeutic regimen or predict benefit from therapy in a subject having cancer. Exemplary biomarkers of the present invention that are useful in cancer diagnosis and prognosis include, but are not limited to, EpCAM, PD-L1, ErbB2, CK19.

Immunological Disorders

The present invention provides methods for diagnosing or prognosing an immunological disorder in a subject, identifying a subject at risk of developing an immunological disorder, or prescribing a therapeutic regimen or predicting benefit from therapy in a subject having an immunological disorder. Immunological disorders are diseases or conditions caused by a dysfunction of the immune system and include allergy, asthma, autoimmune diseases, autoinflammatory syndromes and immunological deficiency syndromes.

In some embodiments, the present invention enables a medical practitioner to diagnose or prognose one or more immunological disorders in a subject. In other embodiments, the present invention enables a medical practitioner to rule out or eliminate one or more immunological disorders as a diagnostic possibility. In yet other embodiments, the present invention enables a medical practitioner to identify a subject at risk of developing an immunological disorder. In other embodiments, the present invention enables a medical practitioner to predict whether a subject will later develop an immunological disorder. In further embodiments, the present invention enables a medical practitioner to prescribe a therapeutic regimen or predict benefit from therapy in a subject having an immunological disorder. Exemplary biomarkers of the present invention that are useful in immunological disorder diagnosis and prognosis include, but are not limited to, TCR, CD16, CD28, CD32, CD79a, and TREM2.

Placental Disease and Fetal Assessment

The present invention provides methods for diagnosing or prognosing placental disease in a subject, identifying a subject at risk of developing a placental disease, or prescribing a therapeutic regimen or predicting benefit from therapy in a subject having a placental disease. Generally, a placental disease is any disease, disorder, or pathology of the placenta. The methods and biomarkers of the present invention may also be used for fetal assessment or diagnosis of fetal disorders, such as, for example, fetal alcohol syndrome or fetal genetic abnormalities. Exemplary biomarkers of the present invention that are useful in placental disease or fetal assessment diagnosis and prognosis include, but are not limited to, PLAP, CSH1, and PSG1.

Biomarkers

Biomarker levels on vesicles are assayed in a biological sample obtained from a subject having or at-risk of having a disease. In some embodiments, biomarker levels on vesicles are assayed in a biological sample obtained from a subject having or at-risk of having a neurological disorder (e.g., Alzheimer's disease). In other embodiments, biomarker levels on vesicles are assayed in a biological sample obtained from a subject having or at-risk of having cancer. In yet other embodiments, biomarker levels on vesicles are assayed in a biological sample obtained from a subject having or at-risk of having an immunological disorder. In still other embodiments, biomarker levels on vesicles are assayed in a biological sample obtained from a subject having or at-risk of having a placental disorder. In some embodiments, one or more biomarkers are selected from the group consisting of a neuron-specific protein (e.g., synaptosome associated protein 25 (SNAP25), neurogranin (NRGN), tau, and synaptophysin), an astrocyte-specific protein (e.g., glial fibrillary acidic protein (GFAP) and excitatory amino acid transporter 1 (EAAT1)), a microglia-specific protein (CD11b), an oligodendrocyte-specific protein (e.g., myelin basic protein (MBP), an oligodendrocyte myelin glycoprotein (OMG)), and an extracellular vesicle-specific protein (dopamine transporter, DAT). In another embodiment, the biomarkers are CD171, phosphorylated tau T181, SNCA, and NRGN. In other embodiments, the biomarkers are acetylcholinesterase (AchE), Lysosomal Associated Membrane Protein 1 (LAMP1), CTSD, RE1 Silencing Transcription Factor (REST), synaptotagmin (SYT), monocyte chemotactic protein-1 (CCL2), IL34, glycogen synthase (GYS), (OR), death receptor 6 (DR6), heat shock protein (HSP), IL12beta, alpha-beta (AB), and beta-secretase (BACE). In some embodiments, one or more biomarkers are selected from the group consisting of cytosolic proteins, secretory proteins, membrane proteins and receptors and their pathological forms, including aggregates and mutated ones. Biomarkers of the present invention include neurotransmitter receptors, such as, for example, dopamine receptors (D1 and D2), serotonin receptors (2A, 2C, and 3B), GABA receptors (1-6, 5. B1, B2), and glutamate receptors (1 and 2). Other receptor biomarkers of the present invention include, insulin receptors, tumor necrosis factor receptors superfamily (TRAL, TNF receptor, death receptor 5 and 6), and neuropeptide receptors (orexin receptor, opioid receptor KOR). Biomarkers of the present invention include membrane proteins, such as, for example, EpCAM, PD-L1, ErbB2, CK19, TCR, CD16, CD28, CD32, CD79a, TREM2, and NCAM. Other known neurological disorder biomarkers may be used in combination with the biomarkers of the present invention. Examples of such biomarkers are provided in US Patent Application Pub. No. 2015/0119278, the contents of which are hereby incorporated by reference.

One of ordinary skill in the art has several methods and devices available for the detection and analysis of the markers of the instant invention. With regard to polypeptides or proteins on vesicles in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amounts of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, an enzyme-linked immunosorbent assay (ELISA), immunofluorescent assay (IFA), immune-polymerase chain reaction assay, electro-chemilumines-cence immunoassay (ECLIA), radioimmunoassay (RIA), competitive binding assay, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the surface markers on vesicles is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample to capture vesicles through binding to surface markers, and then processed quickly through washes and detection steps with detection reagents, as described above, to generate a measurable signal, such as a colored spot.

The analysis of a plurality of markers may be carried out separately or simultaneously with one test sample. Several markers on vesicles may be captured and/or detected using a combination of multiple capture agents and/or detection agents in one test for efficient processing of multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of neurological disorders (e.g., Alzheimer's disease). Markers of such disorders are typically substances found in a bodily sample that can be measured. The measured amount can correlate to underlying disorder or disease pathophysiology, presence or absence of a neurological disorder, probability of a neurological disorder in the future. In patients receiving treatment for their condition the measured amount will also correlate with responsiveness to therapy. In some embodiments, a decrease or increase in the level of one or more biomarkers of the present invention is indicative of a neurological disorder. For example, an increase in phosphorylated tau T181 levels and/or a decrease in NRGN levels on exosomes having the CD171 membrane marker is indicative of Alzheimer's disease. Accordingly, the methods of the present invention are useful for the differential diagnosis of Alzheimer's disease.

In some embodiments, a biomarker is measured by a method selected from the group consisting of immunohistochemistry, immunocytochemistry, immunofluorescence, immunoprecipitation, electro-chemiluminescence immunoassay, radioimmunoassay, immune-polymerase chain reaction, western blotting, and ELISA.

Clinical Assay Performance

The methods of the present invention may be used in clinical assays to diagnose or prognose a neurological disorder in a subject, identify a subject at risk of a neurological disorder, and/or for prescribing a therapeutic regimen or predicting benefit from therapy in a subject having a neurological disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a neurological disorder in a subject, identifying a subject at risk of a neurological disorder, or for prescribing a therapeutic regimen or predicting benefit from therapy in a subject having a neurological disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 100%.

Compositions

Compositions useful in the methods of the present invention include compositions that specifically recognize a biomarker associated with a neurological disorder. Such compositions may include capture agents and/or detection agents that recognize, for example, a neuron-specific protein biomarker, such as synaptosome associated protein 25 (SNAP25), $\alpha\beta$-42, neurogranin (NRGN), tau, phosphorylated tau, and synaptophysin, an astrocyte-specific protein biomarker, such as glial fibrillary acidic protein (GFAP) and excitatory amino acid transporter 1 (EAAT1), an oligodendrocyte-specific protein biomarker, such as myelin basic protein (MBP) and oligodendrocyte myelin glycoprotein (OMG), a microglia-specific protein (CD11b), a cytosolic protein (e.g., glyceraldehyde-3-phosphate dehydrogenase (GAPDH), alpha-synuclein (SNCA), cathepsin D (CTSD), AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, PSG1, or FasL), or a chemokine (CX3CL1) or cytokine (IL1b, IL34, FasL, or IL12B).

In yet other embodiments, the composition is selected from the group consisting of a peptide, a nucleic acid, an antibody, and a small molecule.

In certain embodiments, the present invention relates to compositions that specifically detect a biomarker associated with a neurological disorder. As detailed elsewhere herein, the present invention is based upon the finding that GAPDH, CTSD, NRGN, MBP, GFAP, Tau, phosphorylated Tau, synaptophysin, $\alpha\beta$-42, CX3CL1, IL1b, IL34, CD81, CD63, CD171, SNAP25, EAAT1, SNCA, CD11b, OMG, AchE, LAMP1, REST, SYT, TH, SYP, SYNPO, PSD95, SV2A, CCL2, IL34, GYS, OR, DR6, HSP, IL12b, AB, and BACE can be used as biomarkers for AD and other neurological disorders. In some embodiments, the compositions of the present invention specifically bind to and detect such biomarkers. For example, a composition may comprise a solid support comprising capture agents associated therewith that selectively bind to CD81, CD63, CD171, SNAP25, EAAT1, CD11b, or OMG. In another example, a composition may comprise detection agents that selectively bind to GAPDH, CTSD, NRGN, MBP, GFAP, Tau, phosphorylated Tau, synaptophysin, $\alpha\beta$-42, SNCA, CX3CL1, IL1b, IL34, OMG, AchE, LAMP1, REST, SYT, TH, SYP, SYNPO, PSD95, SV2A, CCL2, IL34, GYS, OR, DR6, HSP, IL12b, AB, and/or BACE.

In some embodiments, the composition comprises an antibody, where the antibody specifically binds to a biomarker or vesicles of the invention. The term "antibody" as used herein and further discussed below is intended to include fragments thereof which are also specifically reactive with a biomarker or vesicle (e.g., exosome). Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', $F(ab')_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an exosome or a biomarker of the present invention, including, for example, neuron-derived exosomes, astrocyte-derived exosomes, oligodendrocyte-derived exosomes, and microglia-derived exosomes, or neuron-specific proteins selected from the group consisting of synaptosome associated protein 25 (SNAP25), neurogranin (NRGN), tau, phosphorylated tar, and synaptophysin, astrocyte-specific proteins selected from the group consisting of glial fibrillary acidic protein (GFAP) and excitatory amino acid transporter 1 (EAAT1), and oligodendrocyte-specific proteins selected from the group consisting of myelin basic protein (MBP) and oligodendrocyte myelin glycoprotein (OMG), a microglia-specific protein (CD11b), and chemokine (CX3CL1) or cytokine (IL1b, IL34, FasL, or IL12B). In another embodiment, the antibody generated is an anti-CD171 antibody, an anti-synaptosome associated protein 25 (SNAP25) antibody, an anti-neurogranin (NRGN) antibody, an anti-tau antibody, an anti-synaptophysin antibody, and anti-CD63 antibody, an anti-$\alpha\beta$-42 antibody, an anti-CD81 antibody, an anti-CTD antibody, an anti-GAPDH antibody, an anti-IL1b antibody, an anti-IL34 antibody, an anti-CX3CL1 antibody, an anti-glial fibrillary acidic protein (GFAP) antibody, an anti-excitatory amino acid transporter 1 (EAAT1) antibody, an anti-SNCA antibody, an anti-TH antibody, and anti-CD11b antibody, an anti-myelin basic protein (MBP) antibody, an anti-oligodendrocyte myelin glycoprotein (OMG) antibody, an anti-dopamine transporter (DAT) antibody, an anti-AchE antibody AchE, an anti-LAMP1 antibody LAMP1, an anti-REST antibody REST, an anti-SYT antibody SYT, an anti-SYP antibody, an anti-SYNPO antibody, an anti-PSD95 antibody, an anti-SV2A antibody, an anti-CCL2 antibody CCL2, an anti-IL34 antibody IL34, an anti-GYS antibody GYS, an anti-OR antibody OR, an anti-DR6 antibody DR6, an anti-HSP antibody HSP, an anti-IL12b antibody IL12b, an anti-AB antibody AB, or an anti-BACE antibody BACE.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a neurological disorder. As detailed elsewhere herein, the present invention is based upon the findings that the levels of CD81, GAPDH, CTSD, NRGN, MBP, GFAP, Tau, phosphorylated Tau (e.g., T181), synaptophysin, CD63, $\alpha\beta$-42, SNCA, CX3CL1, IL1b, IL34, AchE, LAMP1, REST, SYT, TH, SYP, SYNPO, PSD95, SV2A, CCL2, IL34, GYS, OR, DR6, HSP, IL12b, AB, and/or BACE are implicated in the pathology of a variety of neurological disorders, such as, for example, Alzheimer's disease.

In some embodiments, biomarkers inside vesicles are analyzed in addition to the surface biomarkers. In certain embodiments, the present invention relates to compositions for lysing vesicles (e.g., exosomes) in biological samples obtained from a subject. Lytic agents useful in the methods of the present invention include: RIPA buffer; Tris-HCl (pH 6.8); glycerol; SDS; 2-mercaptoethanol; Triton-X 100; M-PER Reagent; T-PER solution; and CHAPS. Lytic agents may be incubated with biological samples to disrupt the membrane of the vesicles of the present invention and release vesicle cargo (e.g., exosomal proteins) for subsequent analysis.

Methods of Treatment

The present invention provides methods of treating a neurological disorder in a subject, comprising administering to the subject an effective amount of a composition, wherein the composition increases, decreases, or maintains the level of CD81, GAPDH, CTSD, NRGN, MBP, GFAP, Tau, phosphorylated Tau (e.g., T181), synaptophysin, CD63, $\alpha\beta$-42, SNCA, CX3CL1, IL1b, or IL34 in the subject. In yet other embodiments, the composition prevents increases or decreases in CD81, GAPDH, CTSD, NRGN, MBP, GFAP, Tau, phosphorylated Tau (e.g., T181), synaptophysin, CD63, a$\beta$-42, SNCA, CX3CL1, IL1b, IL34, AchE, LAMP1, REST, SYT, TH, SYP, SYNPO, PSD95, SV2A, CCL2, IL34, GYS, OR, DR6, HSP, IL12b, AB, or BACE levels. In other embodiments, the present invention provides methods of treating a neurological disorder in a subject, comprising administering to the subject an effective amount of a composition, wherein the composition normalizes the level of CD81, GAPDH, CTSD, NRGN, MBP, GFAP, Tau, phosphorylated Tau (e.g., T181), synaptophysin, CD63, $\alpha\beta$-42, SNCA, CX3CL1, IL1b, IL34, AchE, LAMP1, REST, SYT, TH, SYP, SYNPO, PSD95, SV2A, CCL2, IL34, GYS, OR, DR6, HSP, IL12b, AB, and/or BACE to a reference level.

Kits

The above-described assay reagents, including a solid support with bound capture agents, detection agents, and optionally reagents for performing immunoassays, such as by ELISA, IFA, immune-polymerase chain reaction assay, ECLIA, or RIA, can be provided in kits, with suitable instructions and other necessary reagents, in order to conduct the assays for detecting biomarkers on vesicles, as described above. The kit will normally contain in separate containers the solid support with bound capture agents, detection agents, control formulations (positive and/or negative), and other reagents that the assay format requires. Instructions (e.g., written, CD-ROM, DVD, Blu-ray, flash drive, digital download, etc.) for carrying out the assay usually will be included in the kit. The kit can also contain, depending on the particular assay used, other packaged reagents and materials (i.e., wash buffers, and the like). Assays, such as those described above, can be conducted using these kits.

In another embodiment, the invention encompasses kits for detecting or monitoring a neurological disorder in a subject. A variety of kits having different components are contemplated by the current invention. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating exosomes in a biological sample. In further aspects, the kit comprises a solid support with bound capture agents for isolating exosomes from a biological sample. In certain aspects, the kit comprises a means for quantifying the amount of a biomarker. In further aspects, the means for quantifying the amount of a biomarker comprises reagents necessary to detect the amount of a biomarker.

In another embodiment, the invention includes a kit for diagnosing or prognosing a neurological disorder in a subject, identifying a subject at risk of a neurological disorder, or prescribing a therapeutic regimen or predicting benefit from therapy in a subject having a neurological disorder, the kit comprising: a) a solid support comprising capture agents associated therewith, wherein at least one capture agent selectively binds to CD171, CD63, CD81, SNAP25, EAAT1, or OMG; and b) one or more detection agents, wherein the one or more detection agents selectively binds to CD81, GAPDH, CTSD, NRGN, MBP, GFAP, Tau, phosphorylated Tau (e.g., T181), CD63, aB-42, CX3CL1, IL1b, IL34, AchE, LAMP1, REST, SYT, SYP, SYNPO, PSD95, SV2A, CCL2, IL34, GYS, OR, DR6, HSP, IL12b, AB, or BACE on the surface of the exosomes. In certain embodiments, at least one capture agent or detection agent comprises an antibody, an antibody fragment, an antibody mimetic, or an aptamer that specifically binds to CD171, phosphorylated tau T181, or neurogranin. In certain embodiments, the antibody is selected from the group consisting of a monoclonal antibody, a polyclonal antibody, a chimeric antibody, a nanobody, a recombinant fragment of an antibody, an Fab fragment, an Fab' fragment, an $F(ab')_2$ fragment, an Fv fragment, and an scFv fragment. In another embodiment, the kit comprises an anti-neurogranin antibody, an anti-phosphorylated tau T181 antibody, and an anti-CD171 antibody.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1: Methods for Quantifying Cell-Specific Biomarkers of Exosomes

Exosomes in biological fluids are a new resource of diagnostics in various diseases, because they carry physiological and pathological materials (proteins, metabolites, RNAs, small molecules, etc.) of the mother cells from which they originate and the microenvironment near the mother cells (FIG. 1A). Thus, quantification of such pathological materials in exosomes will be a foundation of the next generation of diagnostics.

However, current methods for analysis of exosomes are complicated and expensive limiting their use in routine diagnostic testing. Quantification of intra-exosomal materials typically involves isolation of target exosomes, lysis or permeabilization of the exosomes to release exosome cargo, and transfer to suitable assay vessels for analysis. The multiple steps involved in current procedures for exosome analysis are labor-intensive and produce large sample-to-sample and assay-to-assay variation.

Here we describe a method in which exosome materials derived from the original mother cell are measured on the surface of exosomes; hence, eliminating the need for a lysis or permeabilization step. Exosome isolation and analysis are conducted on the same solid support without transferring the samples to other assay vessels, which avoids loss of material.

As shown in FIG. 1B, the method is performed using antibodies against at least two different markers on the surface of an exosome, which may include exosome membrane proteins and/or adsorbed markers. For example, a first antibody against an exosome marker, such as a membrane marker (CD81, SNAP25, CD171, EAAT1, OMG, etc.) or adsorbed marker (Tau, NRGN, GFAP, MBP, etc.) is immobilized on an ELISA plate to allow capture of exosomes having that marker. A second antibody against another exosome marker of interest, which can also be a membrane marker (CD81, SNAP25, CD171, EAAT1, OMG, etc.) or adsorbed marker (Tau, NRGN, GFAP, MBP, etc.), is subsequently used to screen the exosomes captured by the first antibody.

Example 2: Detection of Cytosolic Non-Membrane Proteins on the Surface of Exosomes Cytosolic non-membrane proteins were detected on the surface of exosomes as follows. Neuron-specific anti-SNAP25 (FIGS. 2A-2C) or control mouse IgG (FIGS. 2D-2F) were immobilized onto white ELISA plates. Various volume (10, 2.5, and 0 uL) of plasma was suspended in PBS, 0.1% tween-20, or 0.1% triton-X100 PBS in a final volume of 40 uL, and applied to the ELISA plates. After overnight incubation at 4° C., unbound materials were removed, then biotin-labeled antibodies against the exosome surface marker CD81, and 2 different soluble cytosolic proteins (GAPDH and CTSD) were applied to ELISA plates. For PBS samples, antibodies were suspended in PBS without tween-20. For samples with tween-20 and triton-X100, labeled antibodies were suspended in 0.1% tween-20 PBS. Then, conventional chemiluminescent ELISA procedure was carried out, and relative light unit (RLU) was determined.

Figure 2A:
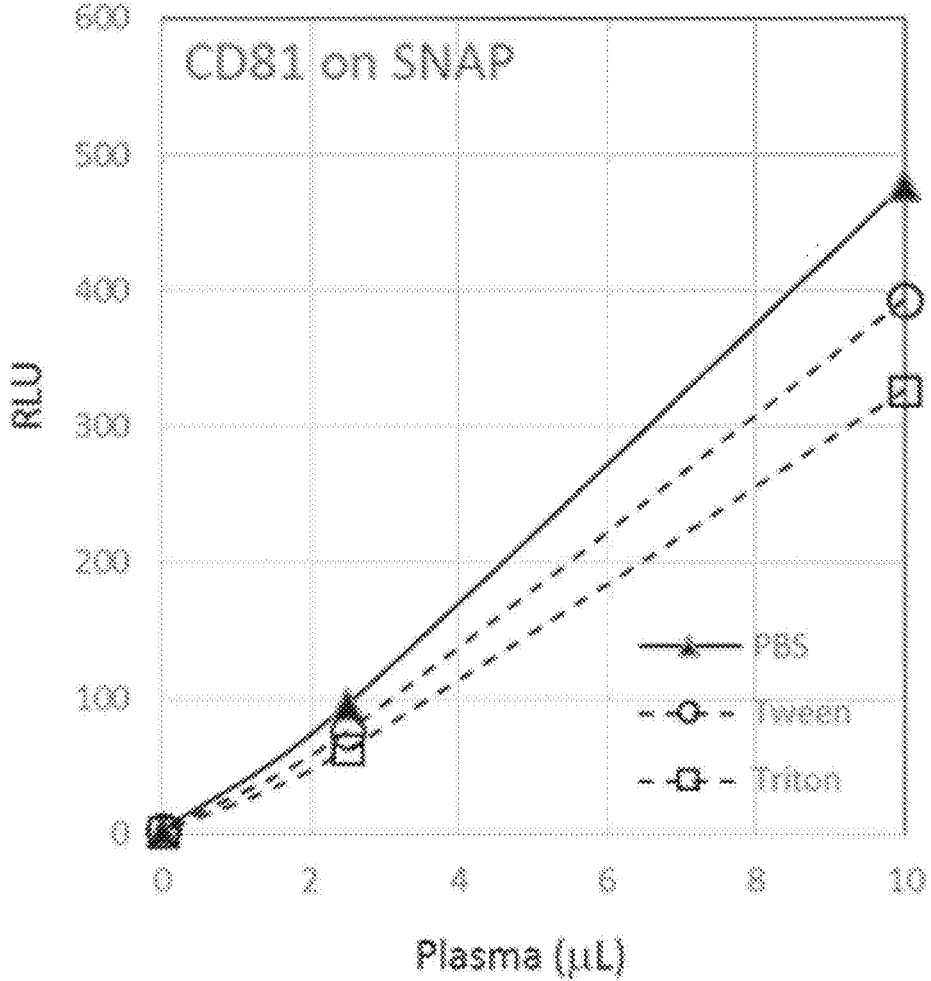
FIGS. 2A-2F show exemplary detection of cytosolic (non-membrane) proteins on the surface of exosomes. Neuron-specific anti-SNAP25 (FIGS. 2A-2C) or control mouse IgG (FIGS. 2D-2F) were immobilized on white ELISA plates. Various volumes (10, 2.5, and 0 uL) of plasma was suspended in PBS (▲), 0.1% tween-20 PBS (●), or 0.1% triton-X100 PBS (□) in a final volume of 40 uL, and applied to the ELISA plates. After overnight incubation at 4° C., unbound materials were removed. Then, biotin-labeled antibodies against the exosome surface marker, CD81 (FIGS. 2A and 2D), and 2 different soluble cytosolic proteins, GAPDH (FIGS. 2B and 2E)) and CTSD (FIGS. 2C and 2F), were applied to ELISA plates. For PBS samples (▲), antibodies were suspended in PBS without tween-20. For samples with tween-20 (○) and triton-X100 (□) labeled antibodies were suspended in 0.1% tween-20 PBS. Conventional chemiluminescent ELISA procedure was carried out, and relative light unit (RLU) was determined.
Figure 2B:
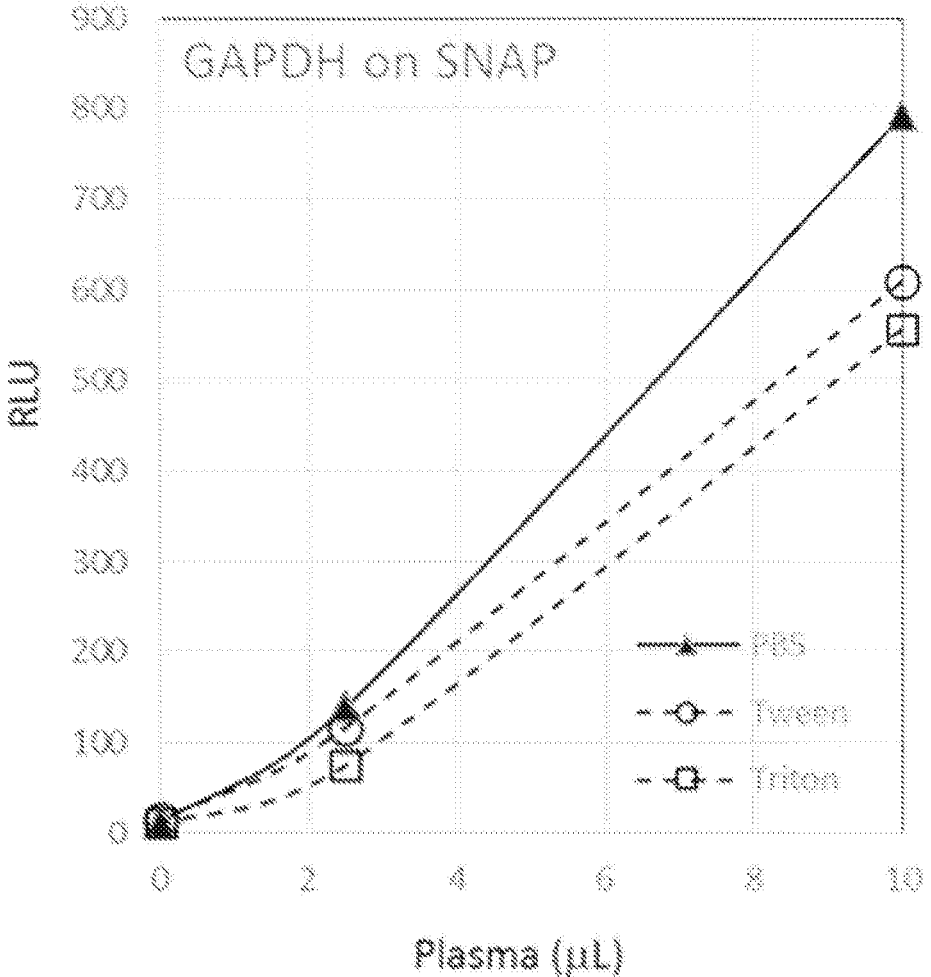
Figure 2C:
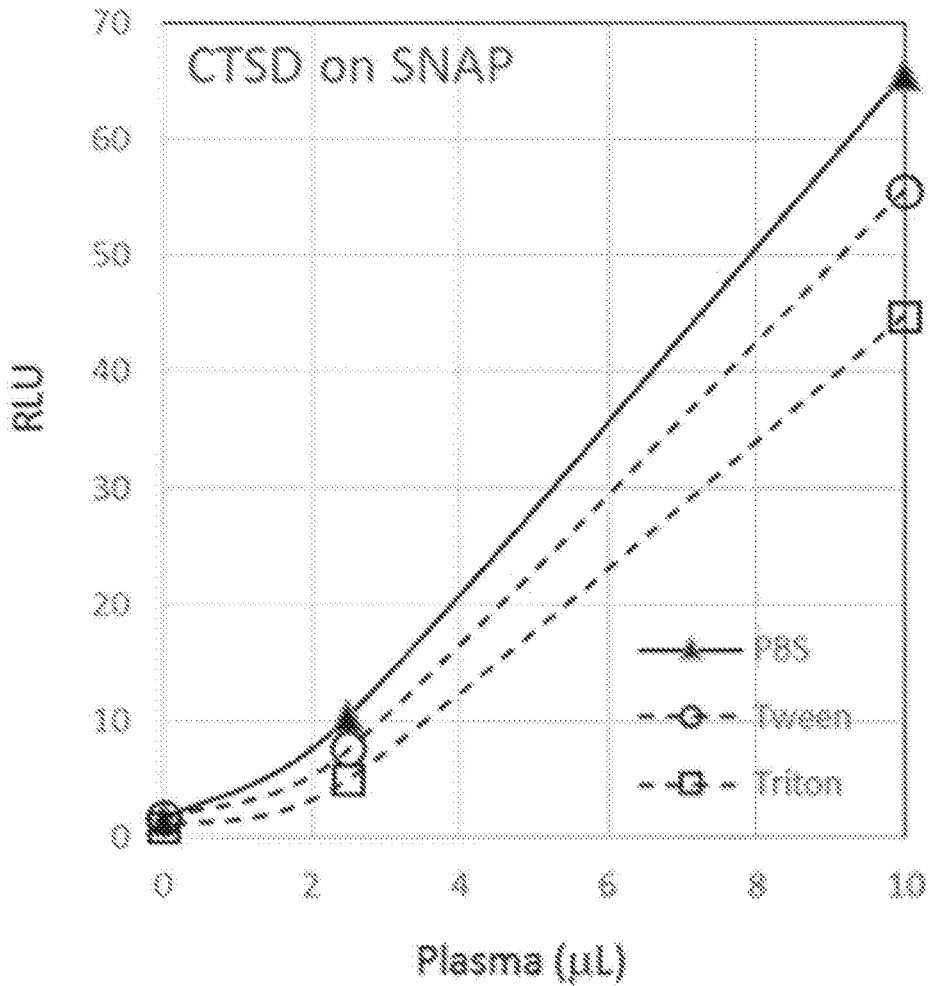
Figure 2D:
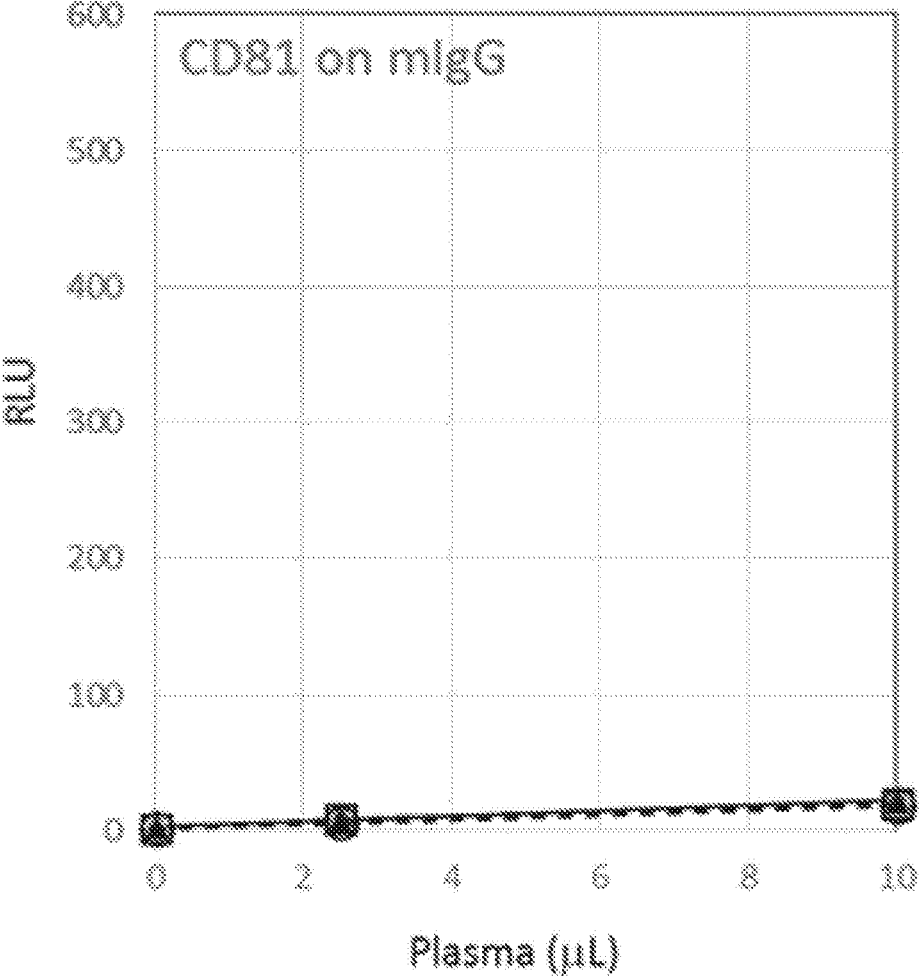
Figure 2E:
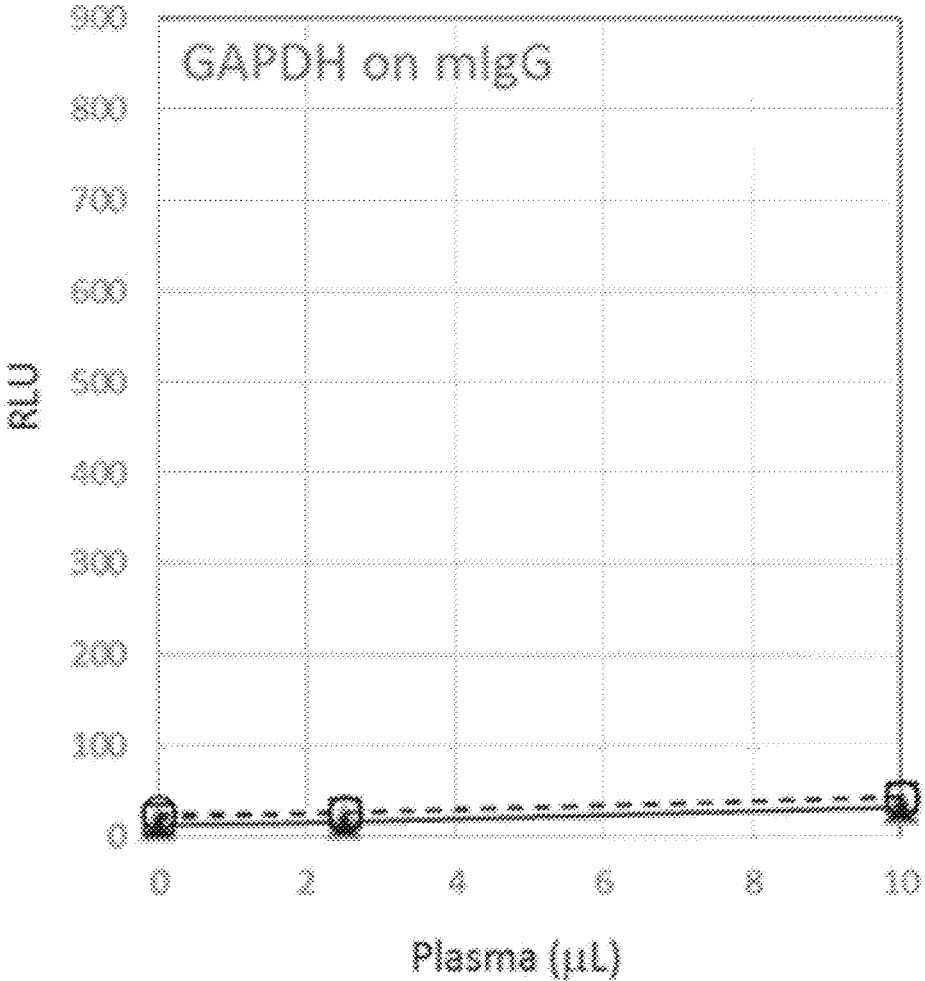
Figure 2F:
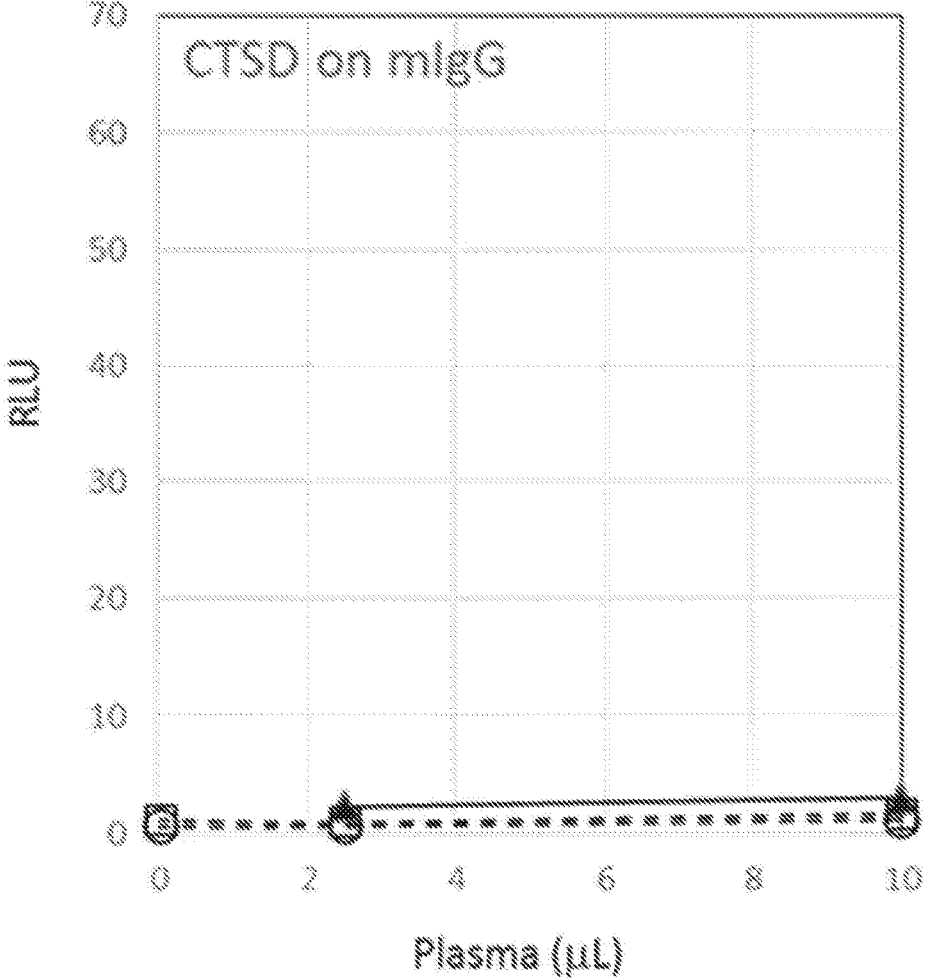

Because GAPDH and CTSD are cytosolic proteins, we hypothesized that these would be detected only after permeabilization of exosomes by tween-20 or triton-X100, whereas membrane protein CD81 would show up in both cases. However, as shown in FIGS. 2A-2C, all 3 markers were detected in a plasma volume dependent manner, whereas no signal was detected on the mouse IgG-immobilized control ELISA plates. These results clearly showed that soluble cytosolic proteins such as GAPDH and CTSD may be detected on the surface of exosomes. These results further showed that the methods and compositions of the present invention are useful for detecting biomarkers on vesicles captured on a solid support using a detection agent that selectively binds to the biomarkers, wherein the vesicles are not lysed or permeabilized.

Example 3: Origin of Cytosolic Non-Membrane Proteins on the Surface of Exosomes

The origin of cytosolic non-membrane proteins on the surface of exosomes was determined as follows. Antibodies against exosome surface marker CD81, neuron surface marker SNAP25, astrocyte surface marker (EAAT1), or oligodendrocyte surface marker (OMG) were immobilized onto white ELISA plates. Ten uL of plasma suspended in 40 uL of PBS were applied to the ELISA plates. After overnight incubation at 4° ° C., unbound materials were removed, then biotin-labeled antibodies against exosome surface marker CD81, general cytosolic marker GAPDH, cytosolic proteins in neuron (NRGN), oligodendrocyte (MBP), and astrocyte (GFAP) were applied to ELISA plates. No antibody control (tPBS) was also included. Then, conventional chemiluminescent ELISA procedure was carried out, and relative light unit (RLU) was determined (FIGS. 3A-3D).

Both CD81 and GAPDH were detected on all ELISA plates (left), indicating that each ELISA plate captured exosomes with GAPDH attached on the surface. In CD81 plate (FIG. 3A) which captured whole exosomes, MBP and GFAP was not detected. Although NRGN was detected, values were very low. In the SNAP25 plate (FIG. 3B) where neuron-derived exosomes were captured, neuron specific NRGN was detected, whereas MBP and GFAP were very low. In the EAAT1 plate (FIG. 3C), where astrocyte-derived exosomes were captured, astrocyte specific GFAP was detected, although NRGN and MBP were also detected. In the OMG plate (FIG. 3D), where oligodendrocyte-derived exosomes were captured, oligodendrocyte specific MBP was detected, though NRGN and GFAP were also detected.

These results showed that soluble markers on the surface of exosomes are derived from mother cells before releasing to outside or from microenvironment shortly after releasing from mother cells. These results further showed that the methods and compositions of the present invention are useful for detecting biomarkers on vesicles, wherein the vesicles are not lysed or permeabilized.

Example 4: Quantification of Marker Proteins

Marker proteins of the present invention were quantified as follows. Since immobilized antibody and biotin-labeled detection antibody bind to 2 different target molecules (such as CD81 and SNAP25), detectable targets standards should have both antigens in the single molecules. Thus, unlike conventional ELISAs, purified proteins or recombinant proteins are not applicable as a quantification standard. Thus, we first screened various plasma samples and found appropriate ones, which contained a large quantity of target exosomes. By assigning 100 units/mL to this plasma, dilution studies were carried out on SNAP25, EAAT1, and OMG plates (FIGS. 4A-4D).

Figure 4A:
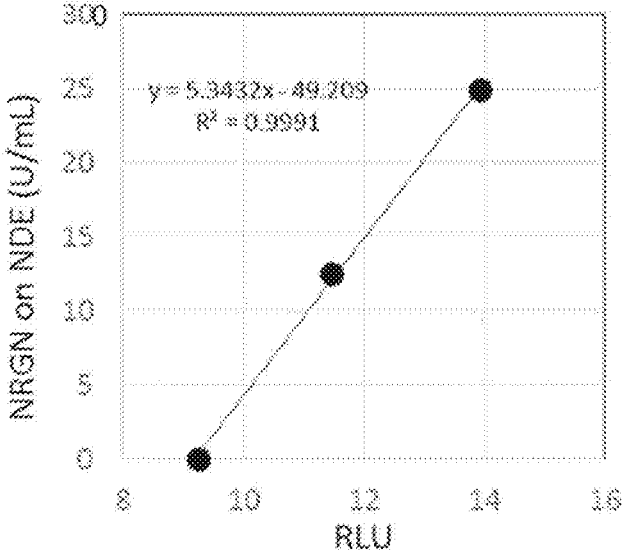
FIGS. 4A-4D show detection and quantification of exosome biomarkers of the present invention. Anti-SNAP25 (FIG. 4A and FIG. 4B), anti-EAAT1 (FIG. 4C), or anti-OMG (FIG. 4D) were immobilized to ELISA plate. Various volume of standard plasma was suspended in PBS, and applied to ELISA wells in a final volume of 40 mL. Antibodies against NRGN (FIG. 4A), tau (FIG. 4B), GFAP (FIG. 4C), and MBP (FIG. 4D) were used as detection antibodies.
Figure 4B:
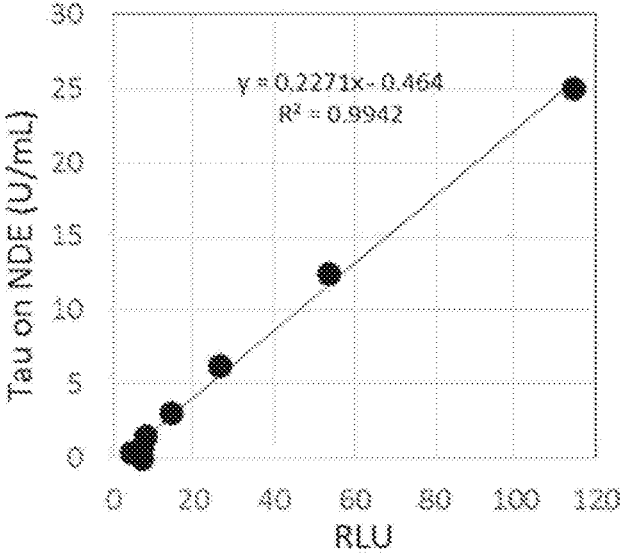
Figure 4C:
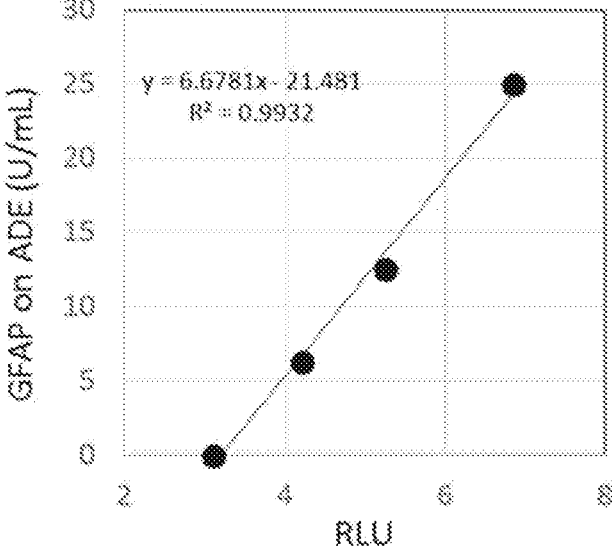
Figure 4D:
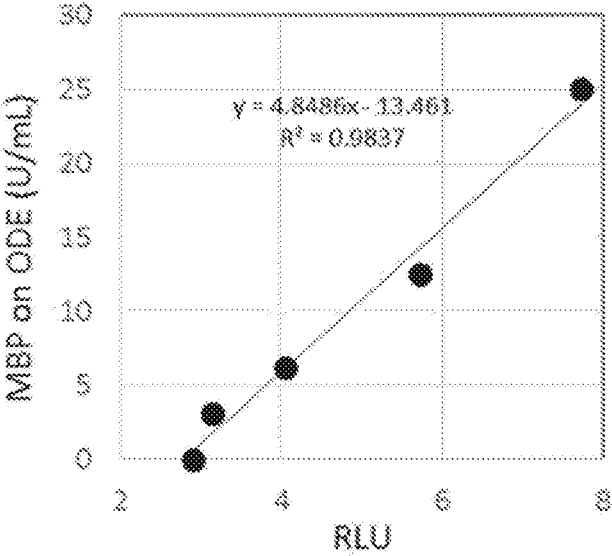

As shown in FIGS. 4A and 4B, the ELISA readings RLU (x-axis) of NRGN (FIG. 4A) and tau proteins (FIG. 4B) on anti-SNAP25-immobilized ELISA (neuron-derived exosome, NDE) plates showed linear changes. Similarly, GFAP (FIG. 4C) and MBP (FIG. 4D) on anti-EAAT1 (astrocyte-derived exosome, ADE) and anti-OMG (oligodendrocyte-derived exosome, ODE) immobilized plates, respectively showed linear changes. Thus, RLU can be successfully converted to units/mL. These results showed that the methods and compositions of the present invention are useful for detecting and measuring biomarkers on vesicles, wherein the vesicles are not lysed or permeabilized.

Example 5: Screening of Exosome Adsorbed Biomarkers

Figure 5A:
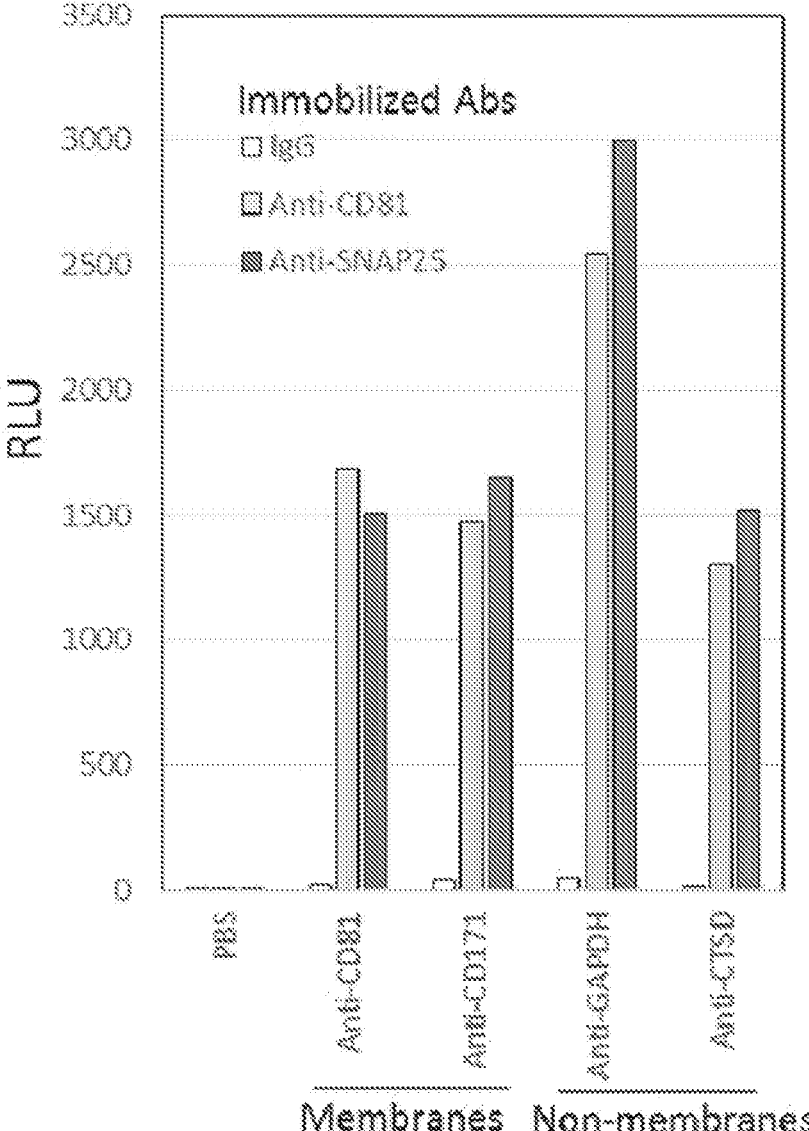
FIGS. 5A-5C show screening of exosome adsorbed markers. Control mouse IgG (open columns), mouse anti-human CD81 (light gray columns), or mouse anti-human synaptosomal-associated protein 25 (SNAP25) (dark gray columns) were immobilized on an ELISA plate, then pooled human plasma was applied to all of ELISA wells. The various detection antibodies listed were used to carry out the ELISA. Detection antibodies (all biotinylated) were against not only exosome membrane proteins (CD81, CD171, CD63, and SNAP25), but also various non-membrane proteins (glyceraldehyde 3-phosphate dehydrogenase (GAPDH), cathepsin D (CTSD), neurogranin (NRGN), myelin basic protein (MBP), glial fibrillary acidic protein (GFAP), tau, microtubule associated protein tau (tau) and phosphorylated tau T181, and amyloid b1-42 peptide (ABETA42). As a negative control, PBS without any biotinylated antibody was used.
Figure 5B:
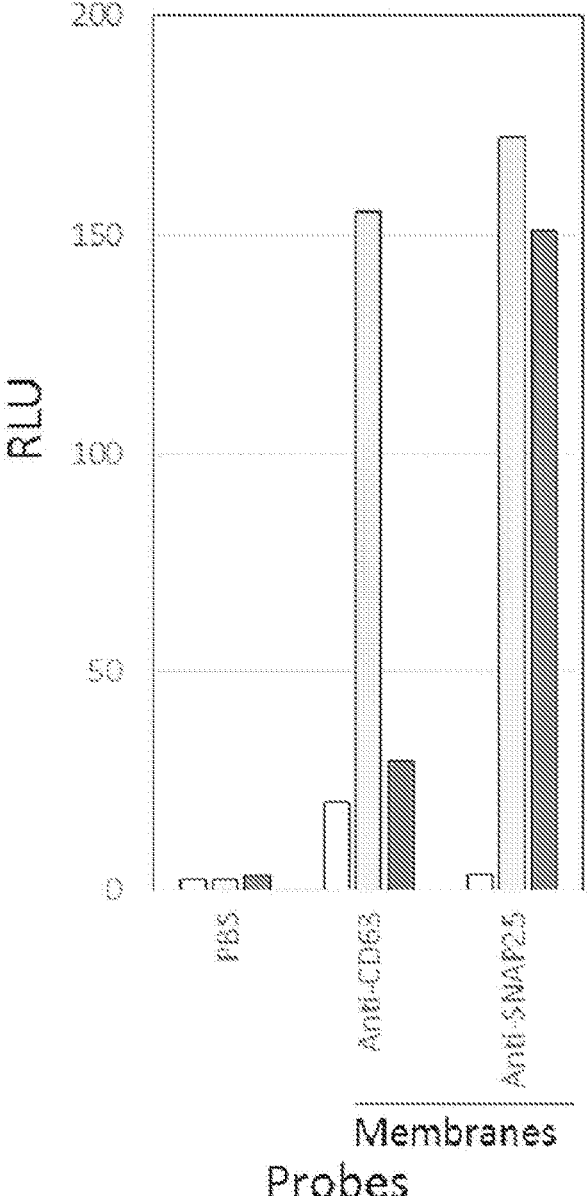
Figure 5C:
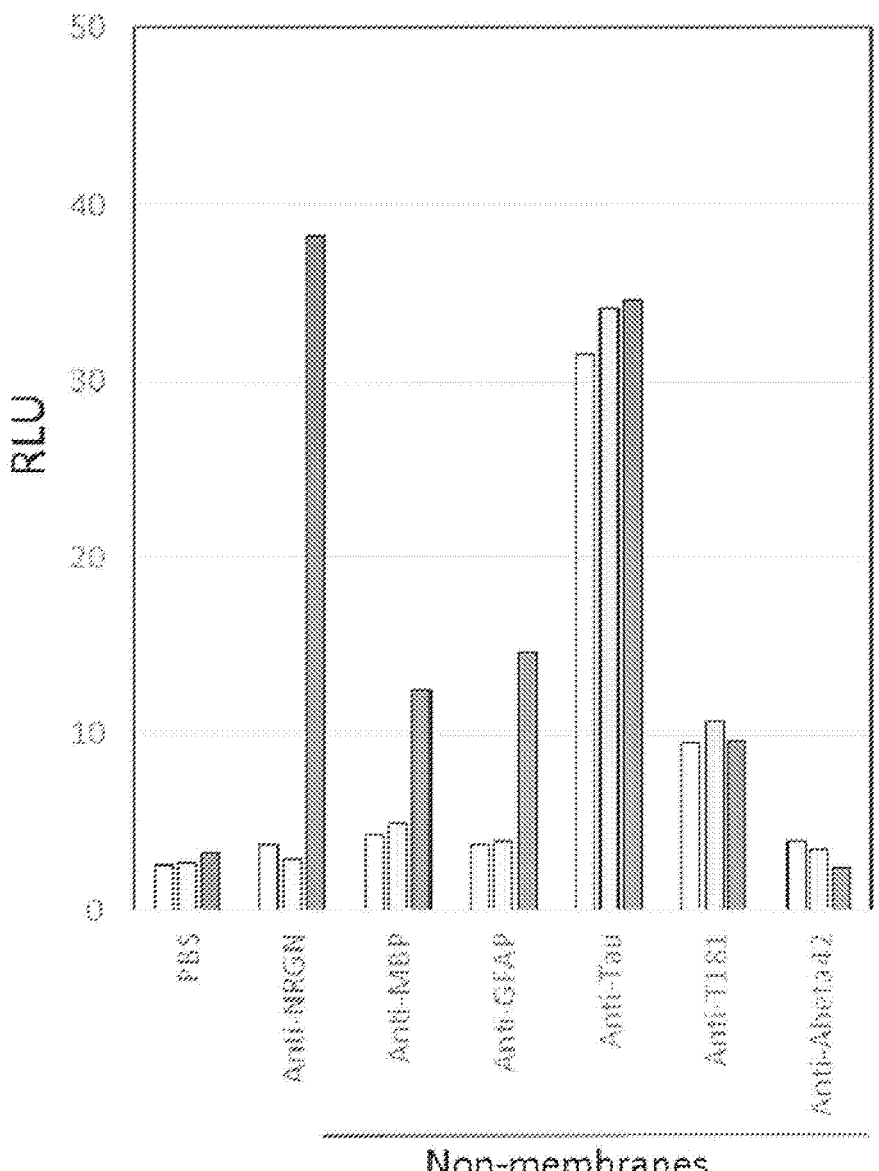
Figure 6A:
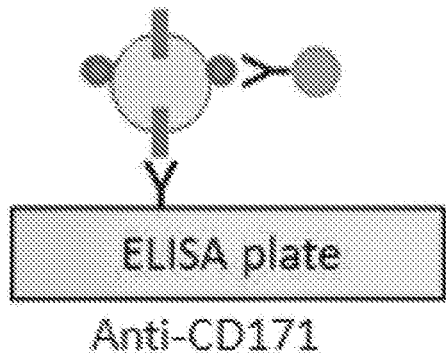
FIG. 6A-6E shows clinical applications for diagnosis of Alzheimer's disease. Anti-CD171 antibodies were immobilized on an ELISA plate as shown in the assay schematic in FIG. 6A. Twelve EDTA plasma samples from subjects with Alzheimer's disease and an age, gender-matched control were applied to ELISA wells, and antibodies against (FIG. 6B) CD81, (FIG. 6C) CTSD.
Figure 6B:
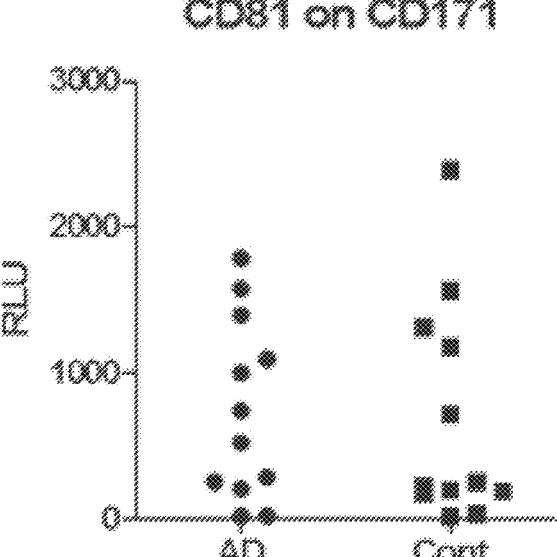
Figure 6C:
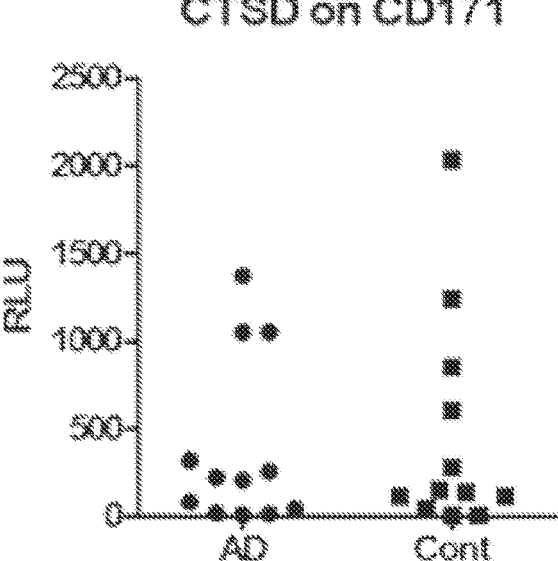
Figure 6D:
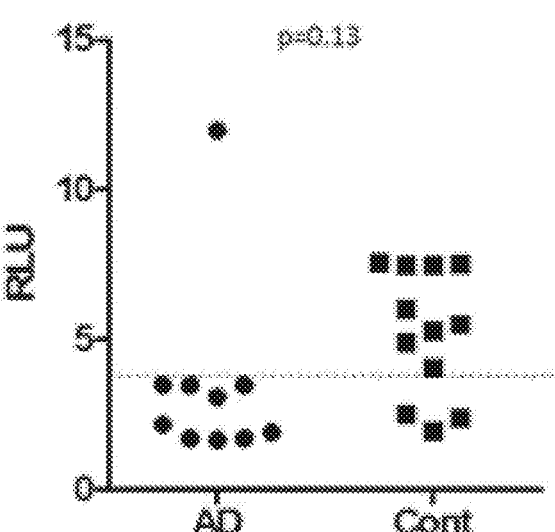
Figure 6E:
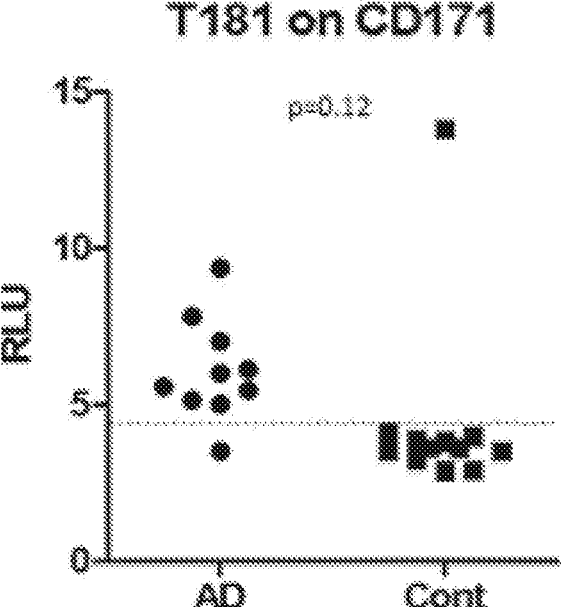
Figure 7A:
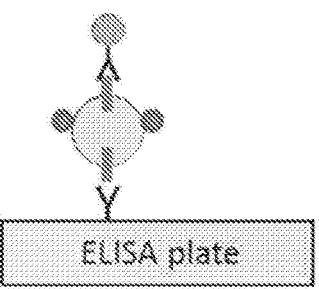
Figure 7B:
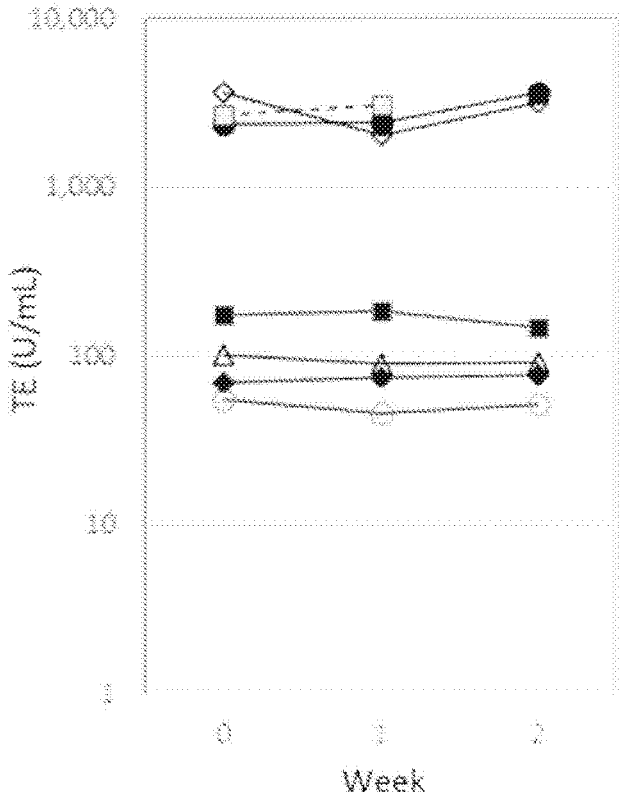
Figure 7C:
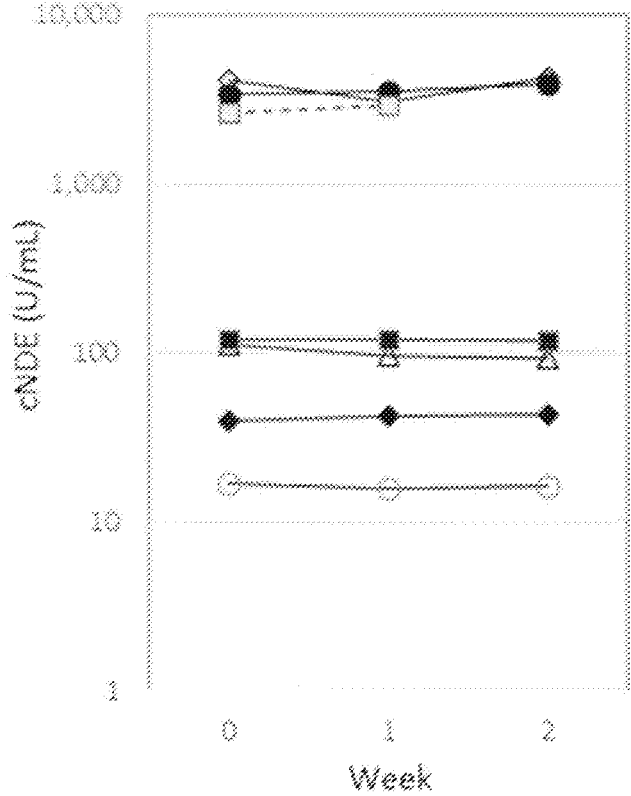
Figure 7D:
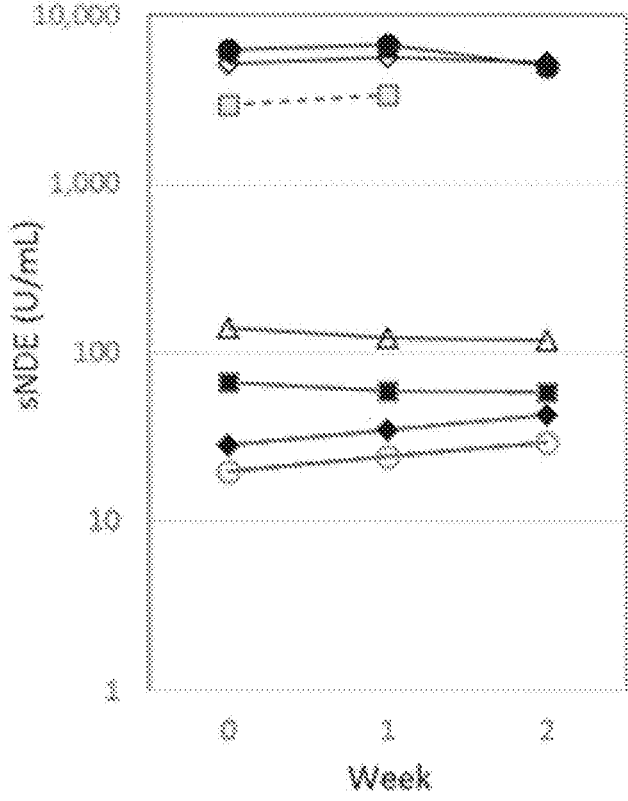
Figure 7E:
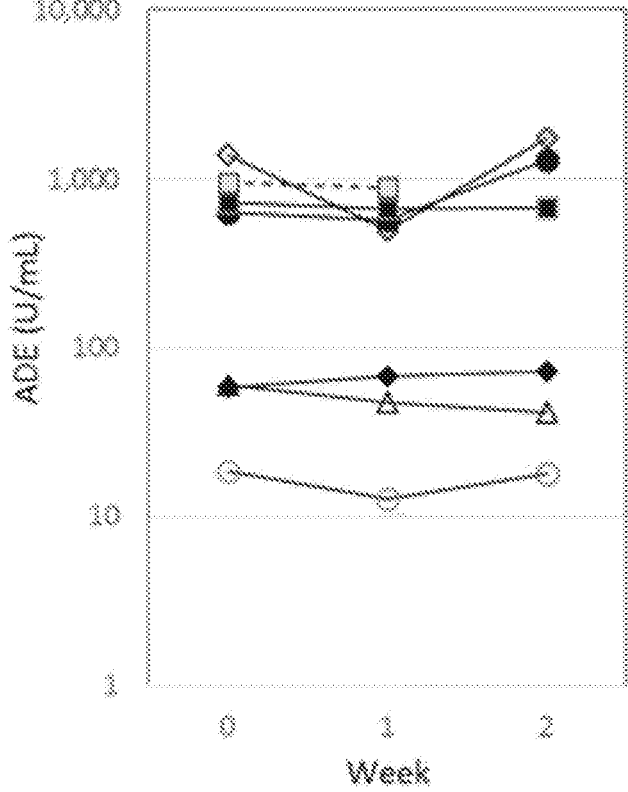
Figure 7F:
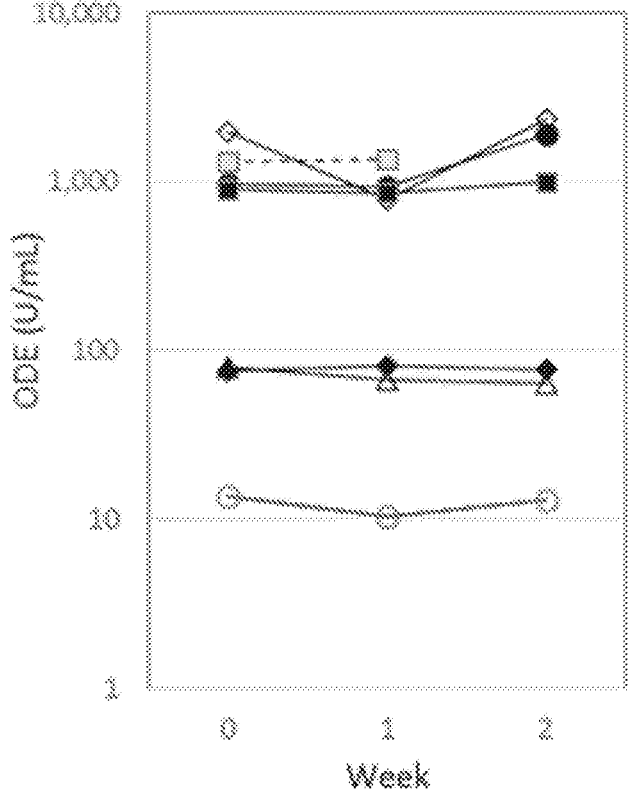
Figure 7G:
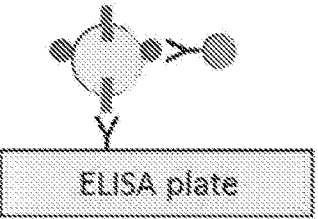
Figure 7H:
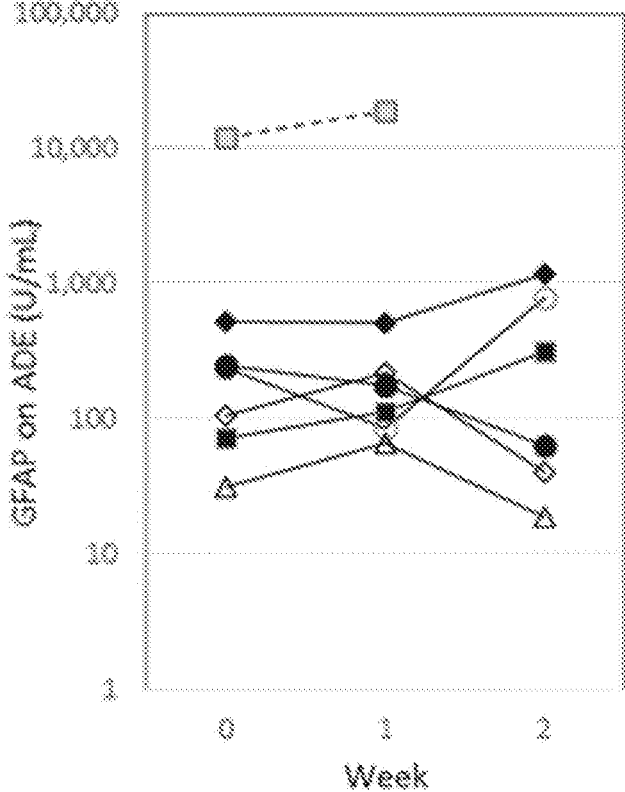
Figure 71:
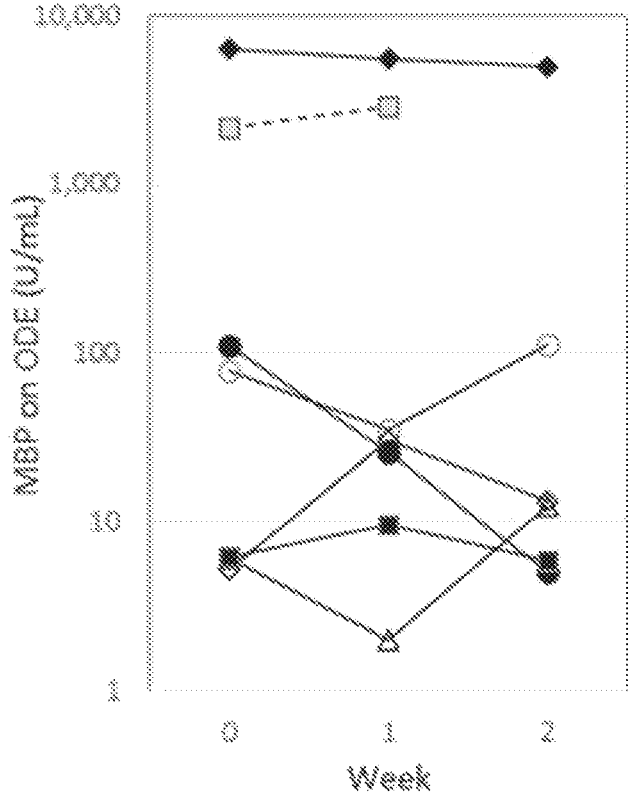
Figure 7J:
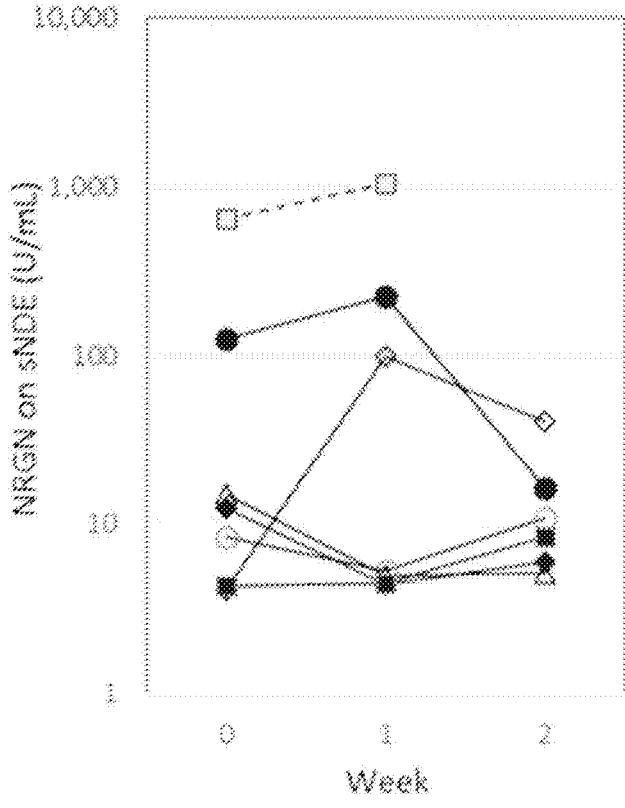
Figure 7K:
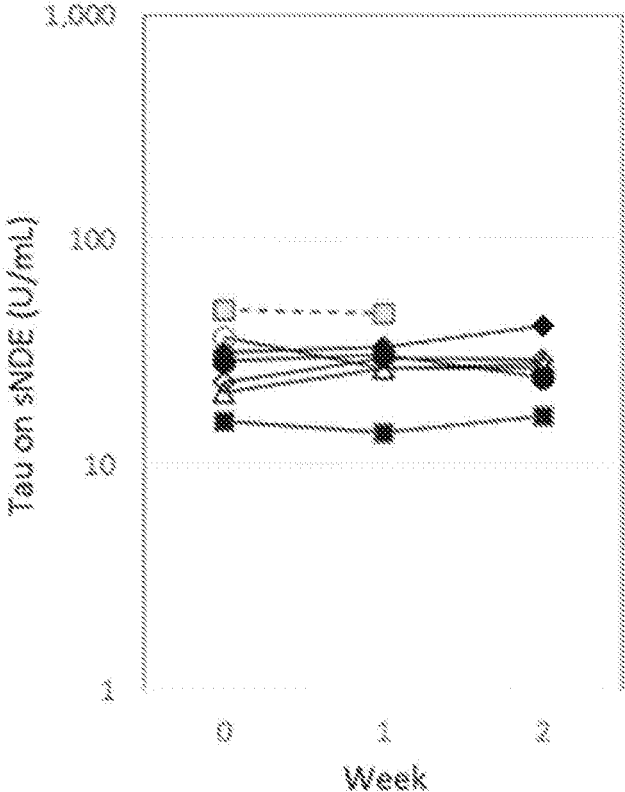
Figure 7L:
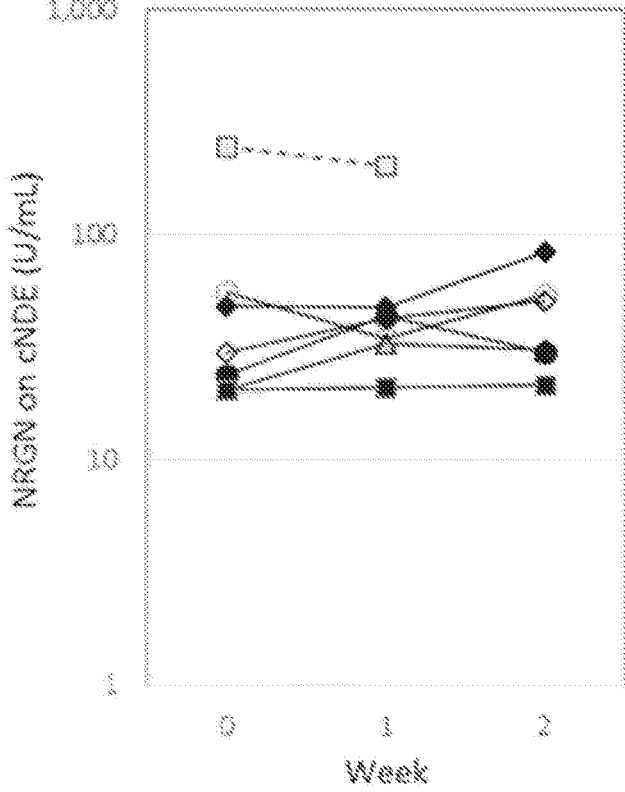

Exosome adsorbed biomarkers were identified as follows. Control mouse IgG, mouse anti-human CD81, or mouse anti-human synaptosomal-associated protein 25 (SNAP25) were immobilized to ELISA plate, then pooled human plasma was applied to all of ELISA wells (FIGS. 5A-5C). Various detection antibodies (all biotinylated) were used to carry out the ELISAs, which included not only antibodies against exosome membrane proteins (CD81, CD171, CD63, and SNAP25), but also, antibodies against various non-membrane proteins (glyceraldehyde 3-phosphate dehydrogenase (GAPDH), cathepsin D (CTSD), neurogranin (NRGN), myelin basic protein (MBP), glial fibrillary acidic protein (GFAP), tau, microtubule associated protein tau (tau) and phosphorylated tau T181, and amyloid b1-42 peptide). As a negative control, PBS without any biotinylated antibody was used.

As shown in FIG. 5A, ELISA signals (RLU) were clearly positive for both the anti-CD81 and anti-SNAP25-immobilized plate, whereas very few signal was detected on control mouse IgG-immobilized plate, indicating that the system was CD81 or SNAP25 specific. As shown in PBS, nonspecific signal without detection antibodies were very low, indicating that the assay was detection antibody specific. The detection of membrane proteins (CD81, CD171, CD63, and SNAP25) confirmed that the assay captured exosomes (FIGS. 5A and 5B). Surprisingly, non-membrane proteins such as GAPDH, CTSD, NRGN, MBP, and GFAP were also detected (FIG. 5C). These results showed that the methods and compositions of the present invention are useful for identifying, detecting, and measuring biomarkers on vesicles, wherein the vesicles are not lysed or permeabilized.

Example 6: Diagnosis of Alzheimer's Disease in Humans

The methods and compositions of the present invention were used to diagnose Alzheimer's disease in biological samples from humans as follows. Anti-CD171 were immobilized on an ELISA plate. Twelve samples of EDTA plasma from subjects having Alzheimer's disease (AD) and age, gender-matched controls were applied to ELISA wells, and antibodies against CD81, CTSD. NRGN, p-tau T181 were used as detection antibodies (FIGS. 6A-6E).

As shown in Table 1 below, NRGN values were lower in AD samples than the control, and T181 values were higher in AD samples than the control. A chi square test showed that these 2 groups were significantly different (p=0.002 for NRGN, p=0.0001 for T181), as shown in Table 1. These results showed that the methods and compositions of the present invention could be used to diagnose Alzheimer's disease.

TABLE 1

| NRGN on CD171 | | |
| --- | --- | --- |
| | High | Low |
| AD | 1 | 9 |
| Cont | 9 | 3 | p = 0.002

| T181 on CD171 | | |
| --- | --- | --- |
| | High | Low |
| AD | 9 | 1 |
| Cont | 1 | 11 | p = 0.0001

Example 7: Stability of Plasma Exosomal Biomarker Levels

The stability of plasma exosomal biomarker levels was determined as follows. Anti-CD81, anti-CD171, anti-SNAP25, anti-EAAT1, and anti-OMG were immobilized on separate ELISA plates. EDTA plasma was obtained from 7 control subjects every week for 2-3 weeks, and applied to the ELISA wells. For detection of exosome membrane targets (FIGS. 7A-7F), an anti-CD81 probe was used on the CD81 plate (total exosome, TE); an anti-CD171 probe was used on the CD81 plate (CD171-based NDE, cNDE); an anti-SNAP25 probe was used on the CD81 plate (SNAP25-based NDE, sNDE); an anti-CD81 probe was used on the EAAT1 plate (ADE); and an anti-CD81 probe was used on the OMG plate (ODE). For detection of exosome surface protein targets (FIGS. 7G-7L), GFAP probe on EAAT1 plate, MBP probe on OMG plate, NRGN probe on SNAP25 plate, tau probe on SNAP25 plate, and NRGN probe on CD171 plate, respectively.

Although each value was largely spread among tested subjects (except tau on SNAP25 plate), the values were quite constant within the same individual except NRGN on SANP25 plate. These results showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing a neurological disorder in a subject. These results further suggested that the methods and compositions of the present invention would be useful for diagnosing a disease or disorder.

Example 8: Plasma on Anti-NRGN-Immobilized ELISA Plate

Plasma exosomal biomarkers were identified as follows. Anti-NRGN or control mouse IgG were immobilized on an ELISA plate. EDTA plasma or PBS alone were applied to the ELISA wells. Antibodies against NRGN, CD171, SNAP25, CD81, EAAT1, OMG were used for detection, and a PBS control was used for comparison.

Figure 8A:
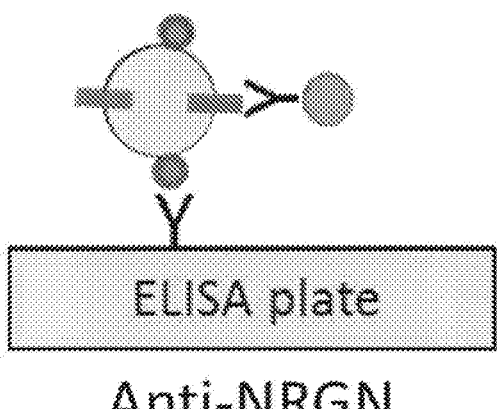
FIGS. 8A and 8B show detection and quantification of exosome biomarkers of the present invention in plasma using an anti-NRGN-immobilized ELISA plate.
Figure 8B:
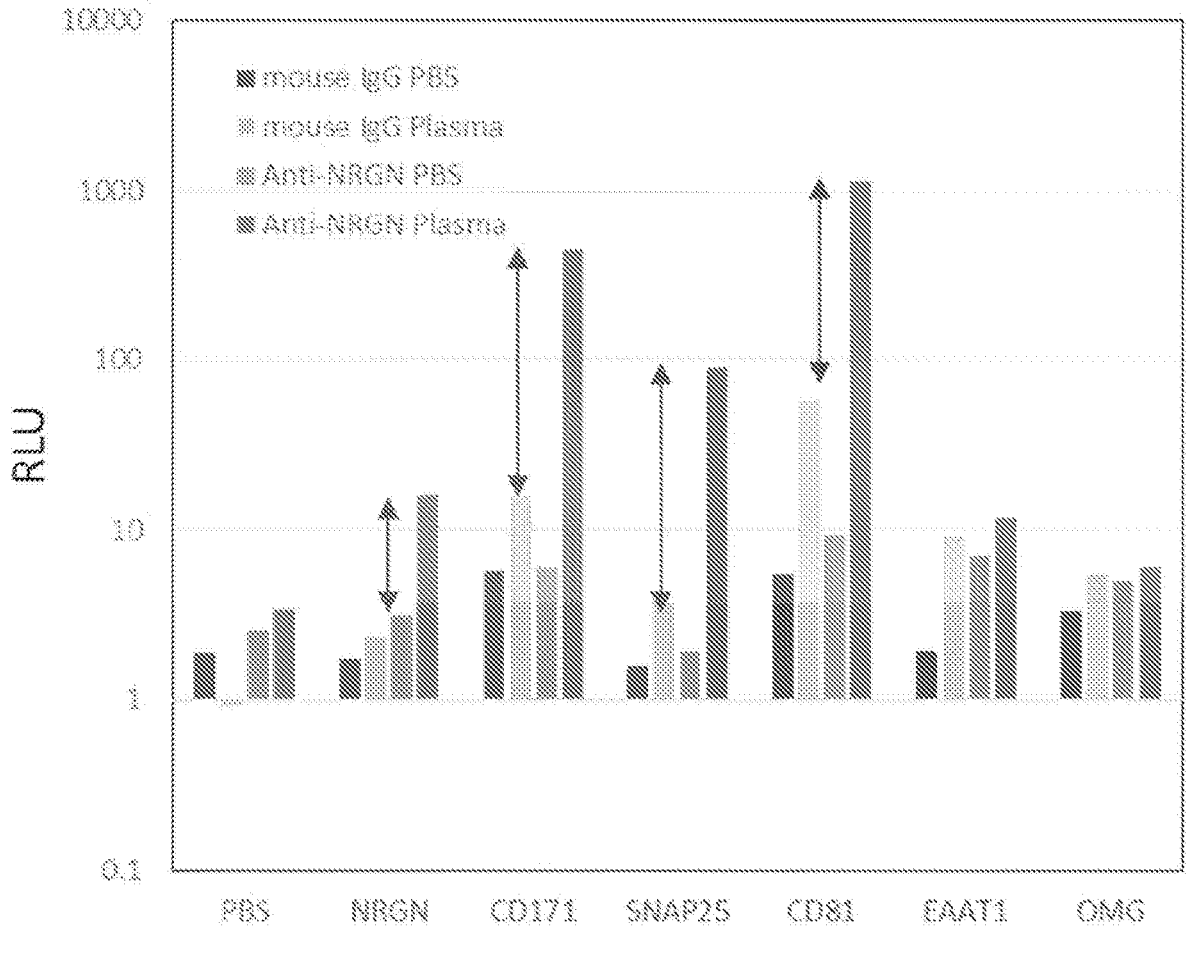

As shown in FIG. 8B, plasma applied on the anti-NRGN immobilized ELISA plate tested positive for NRGN, CD171, SNAP25, and CD81, but not EAAT1 and OMG, indicating specificity for neurons of NRGN on the SNAP25 plate, but not astrocytes or oligodendrocytes (FIG. 8B). These results showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing a neurological disorder in a subject. These results further suggested that the methods and compositions of the present invention would be useful for diagnosing a disease or disorder.

Example 9: Microglia Targeting of Exosome Biomarkers

Microglia targeting of exosome biomarkers was performed as follows. An anti-CD11b antibody or a control mouse IgG were immobilized on ELISA plates. EDTA plasma from 7 different donors (IR1-IR7) or PBS alone were applied to ELISA wells. Antibodies against GFAP (FIG. 9B), MBP (FIG. 9C), or NRGN (FIG. 9D) were used as detection antibodies.

Figure 9A:
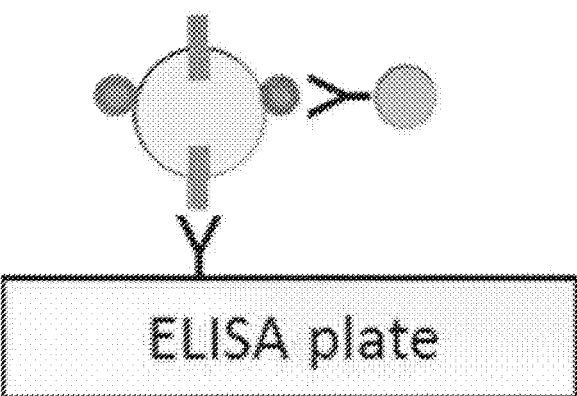
FIGS. 9A-9D show microglia targeting of exosome bio-markers of the present invention.
Figure 9B:
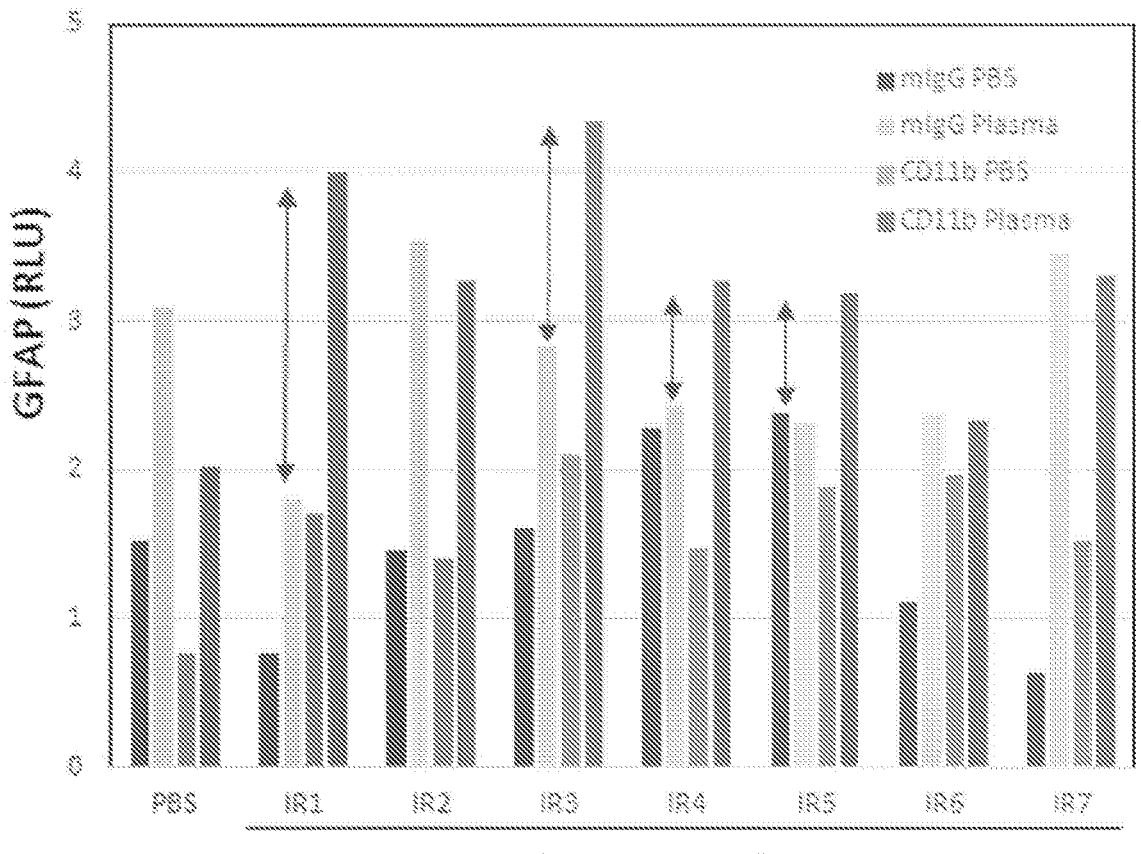
Figure 9C:
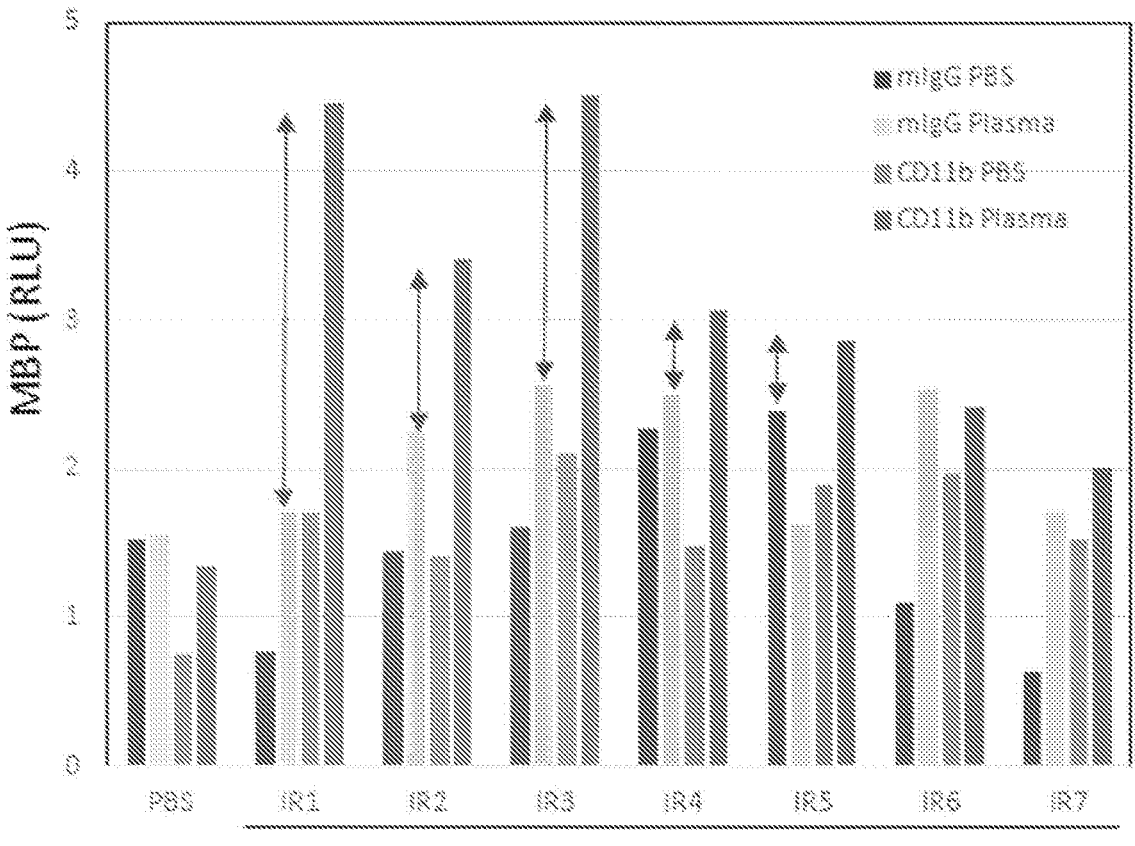
Figure 9D:
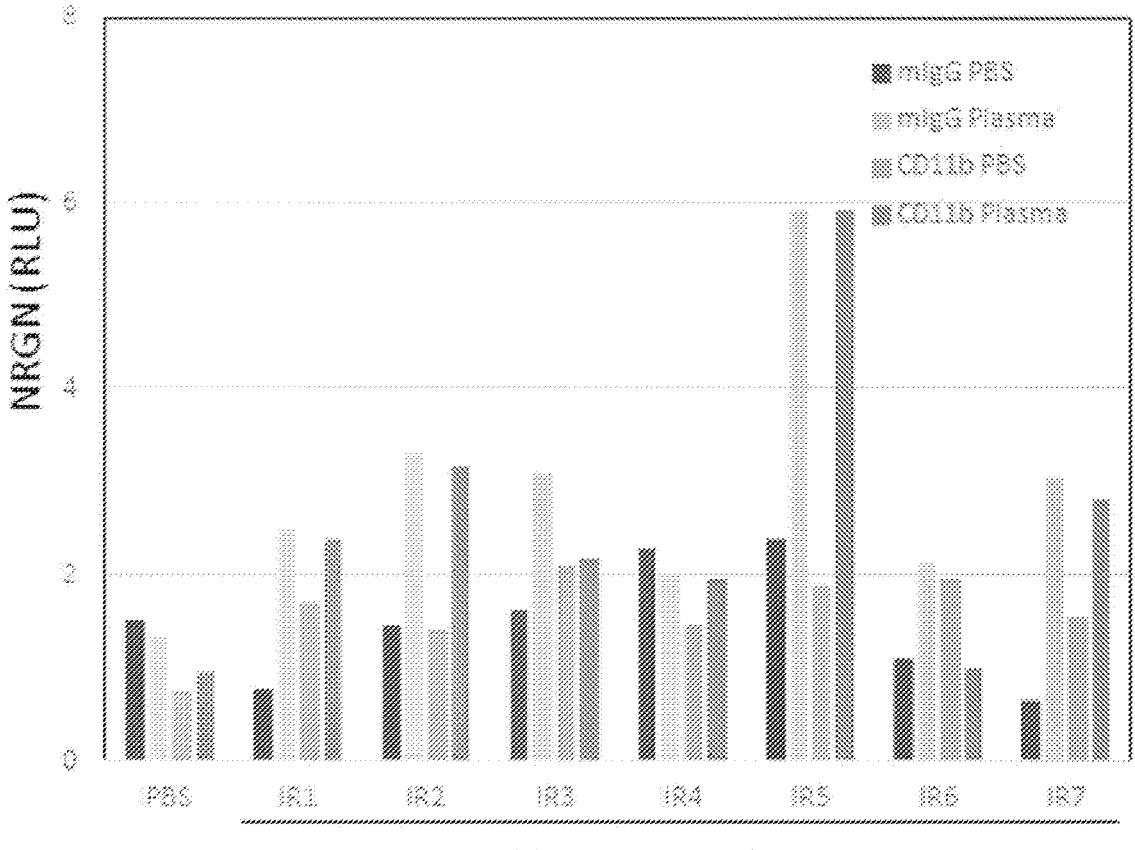

As shown in FIGS. 9B-9D, although no microglia-specific antibody is available, and anti-CD11b binds to both microglia and peripheral macrophages, microglia analysis can be done by assessing brain-derived proteins on the surface of CD11b⁺ exosomes. Four (GFAP) to five (MBP) donors showed positive signals higher than the 3 controls (PBS on IgG plate, plasma on IgG plate and PBS on CD1b plate), indicating the interaction of microglia with astrocytes and oligodendrocytes in these donors. None of the seven subjects, however, failed to show NRGN (FIG. 9D).

These results showed that the methods of the present invention are useful for detecting biomarkers (GFAP, MBP, and NGRN) on microglia-derived exosomes. These results showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing neurological disease in a subject. These results further suggested that the methods and compositions of the present invention would be useful for diagnosing a disease or disorder.

Example 10: Detection of Secretory Proteins (Cytokines IL1b and IL34 and Chemokines CX3CL1) on the Surface of Brain-Derived Exosomes Secretory proteins (cytokines and chemokines) were detected on the surface of brain-derived exosomes as follows. Various concentrations of standard plasma (FIGS. 10A, 10C, and 10E) and fixed dilution of seven control plasma samples (⅛ dilution for IL1b and IL34 and ¼ dilution for CX3CL1) and PBS control was applied to ELISA plates containing immobilized antibodies (anti-SNAP25, anti-EAAT1, anti-OMG, and control mouse IgG) to capture NDE, ADE, and ODE, respectively. Control mouse IgG was used to evaluate non-specific bindings.

Figure 10A:
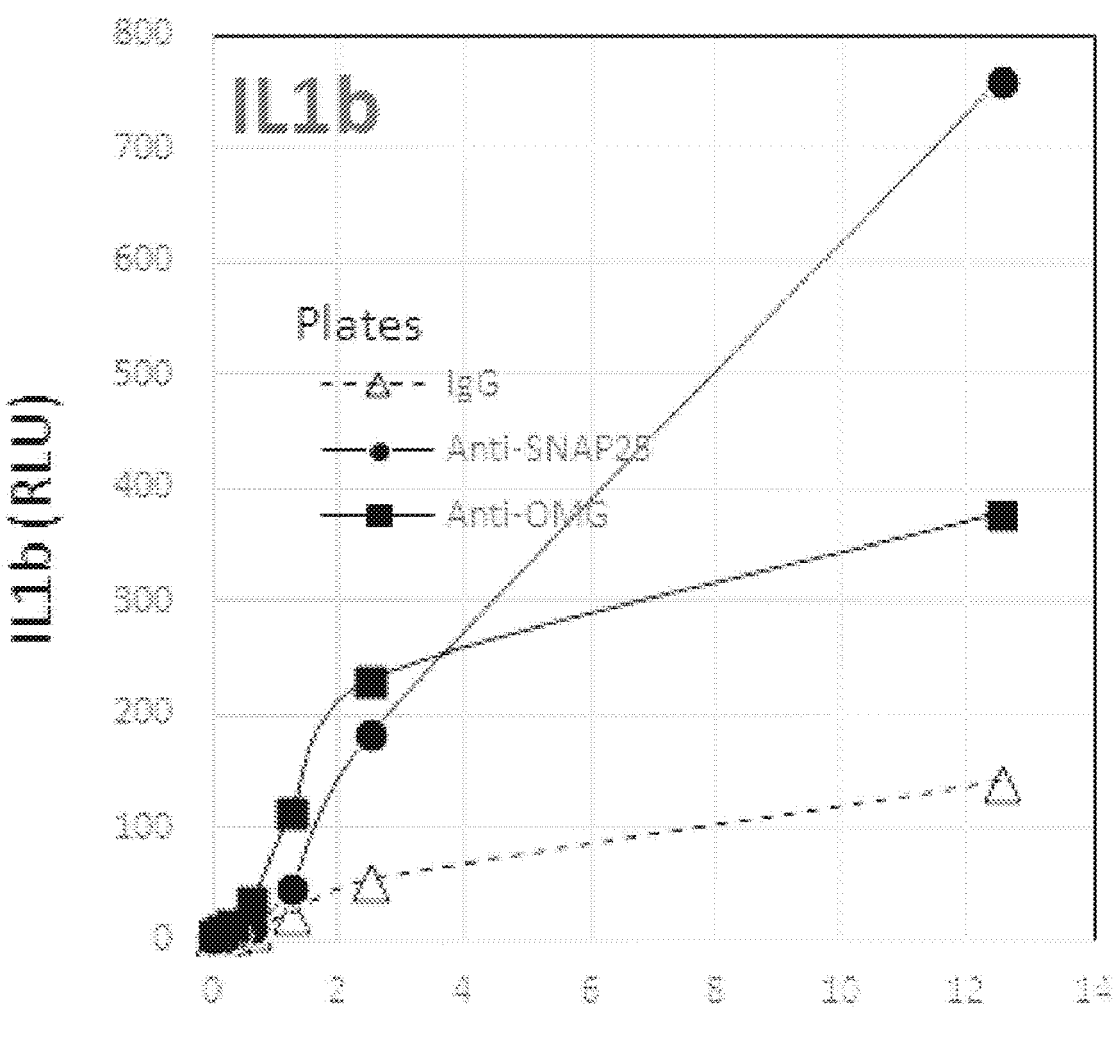
Figure 10B:
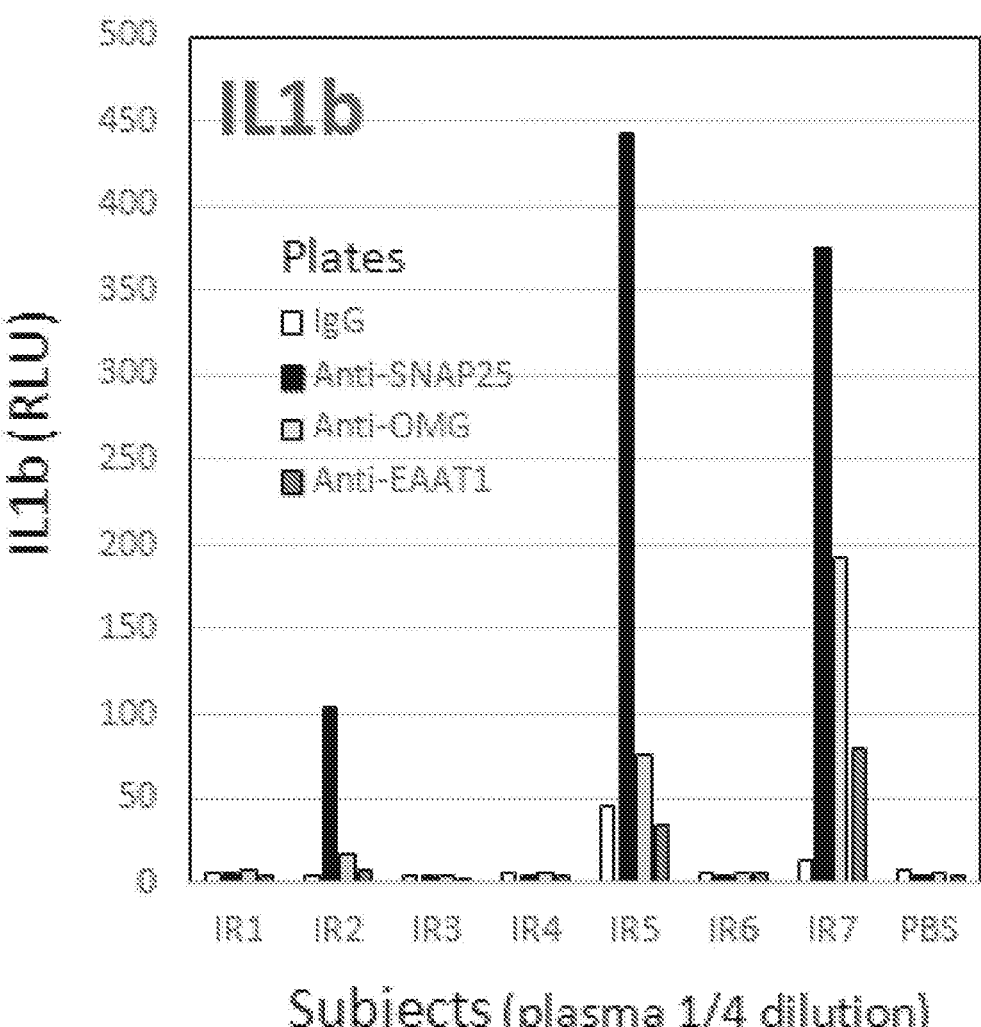
Figure 10C:
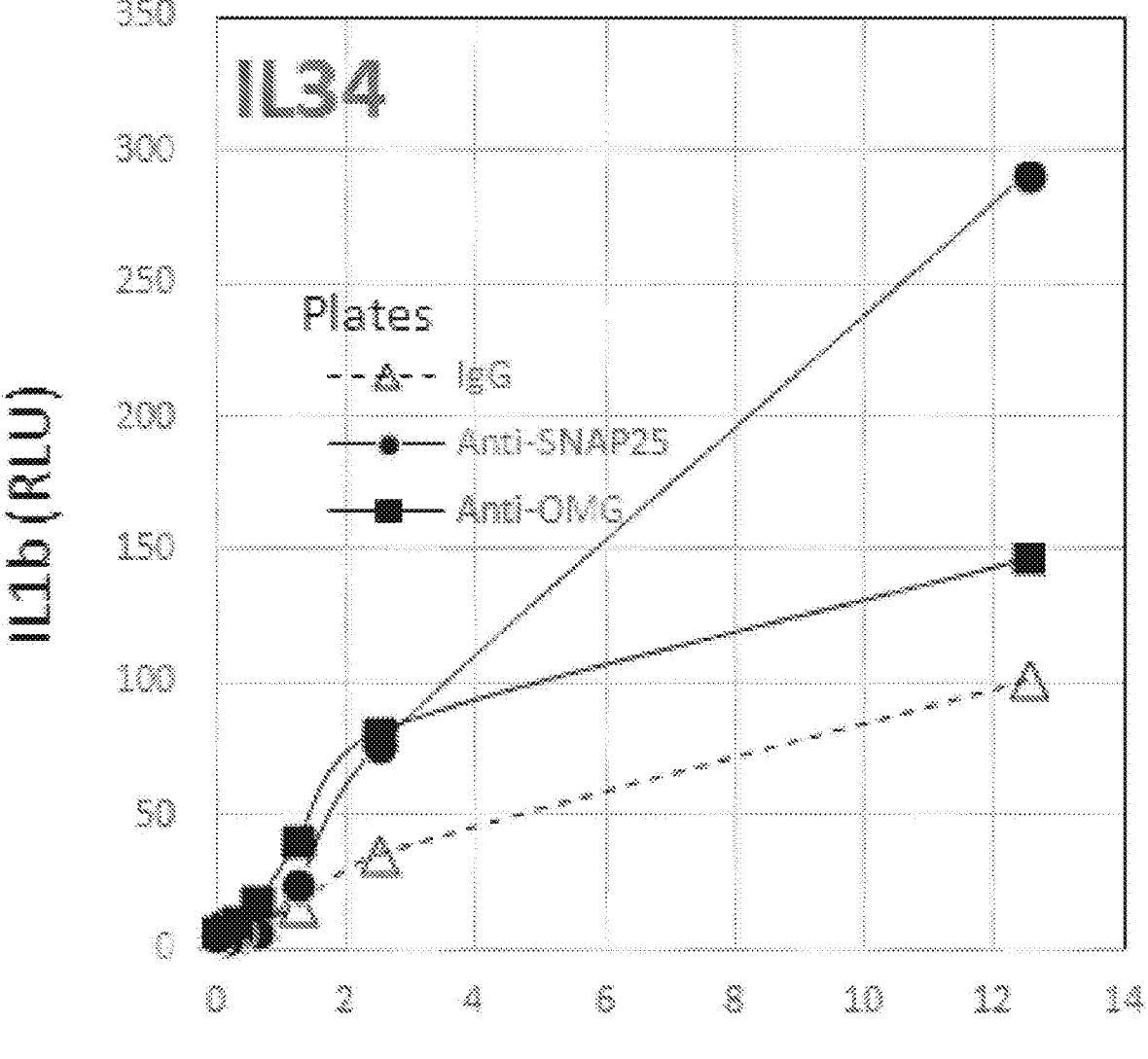
Figure 10D:
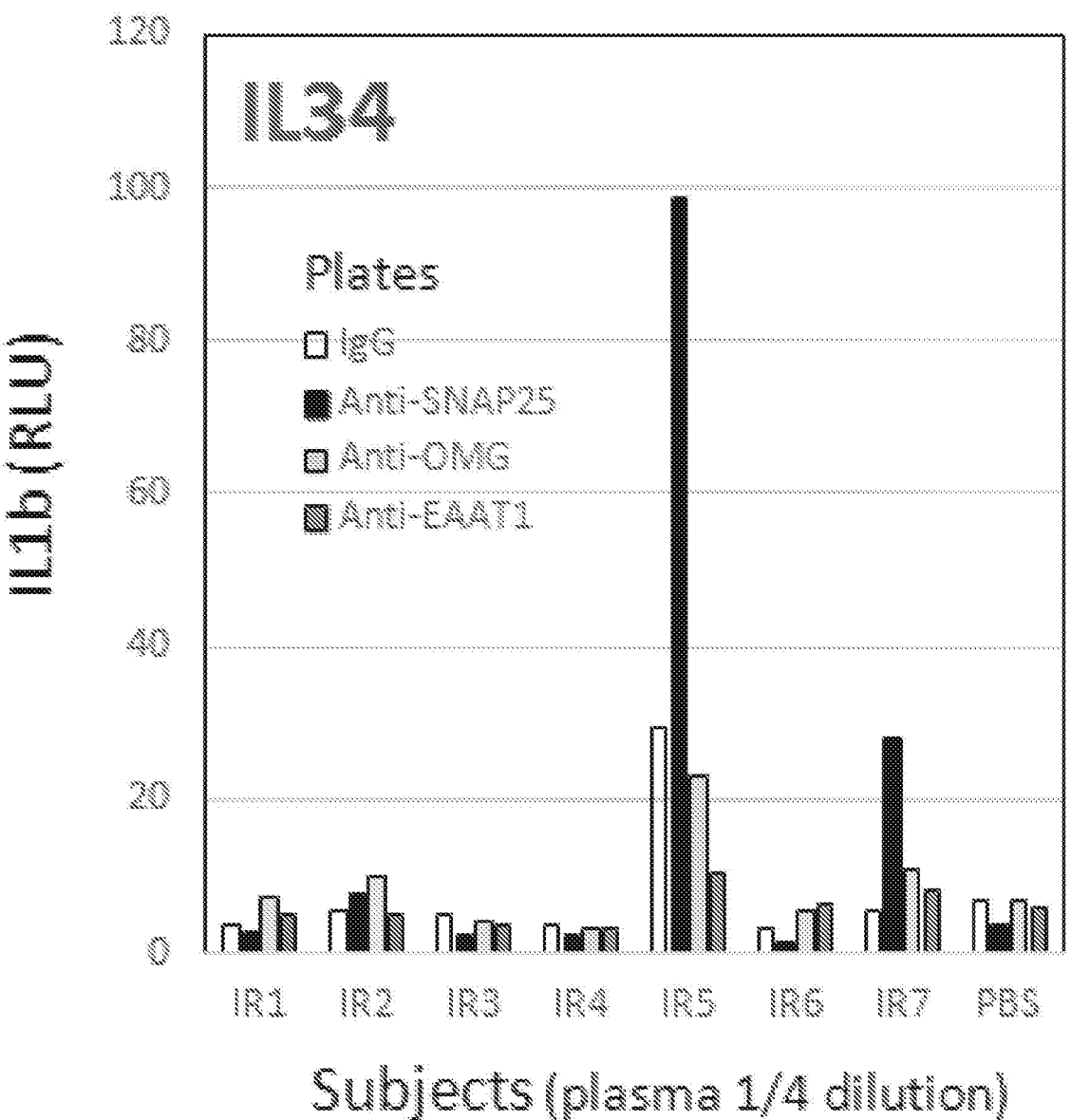
Figure 10E:
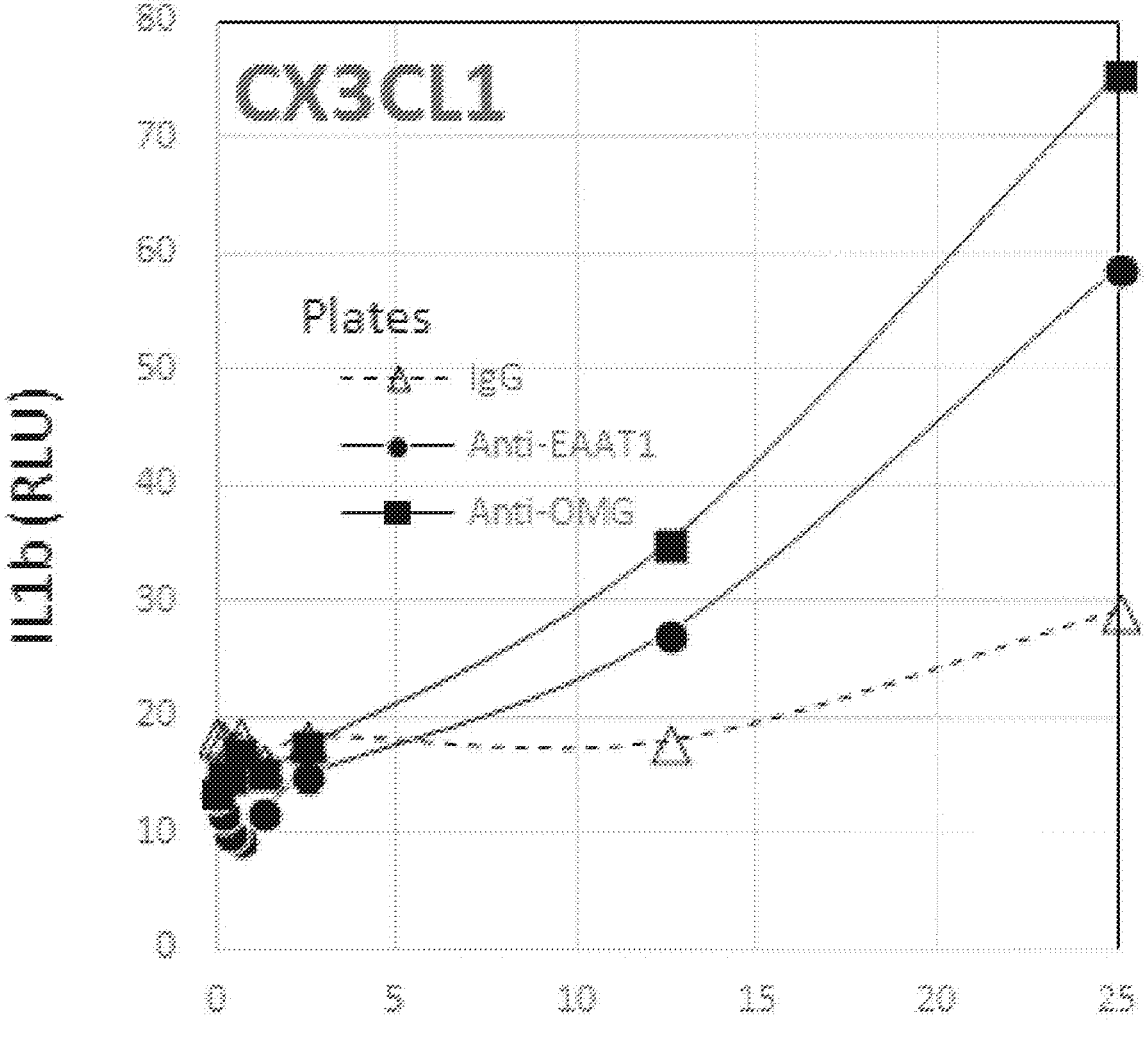
Figure 10F:
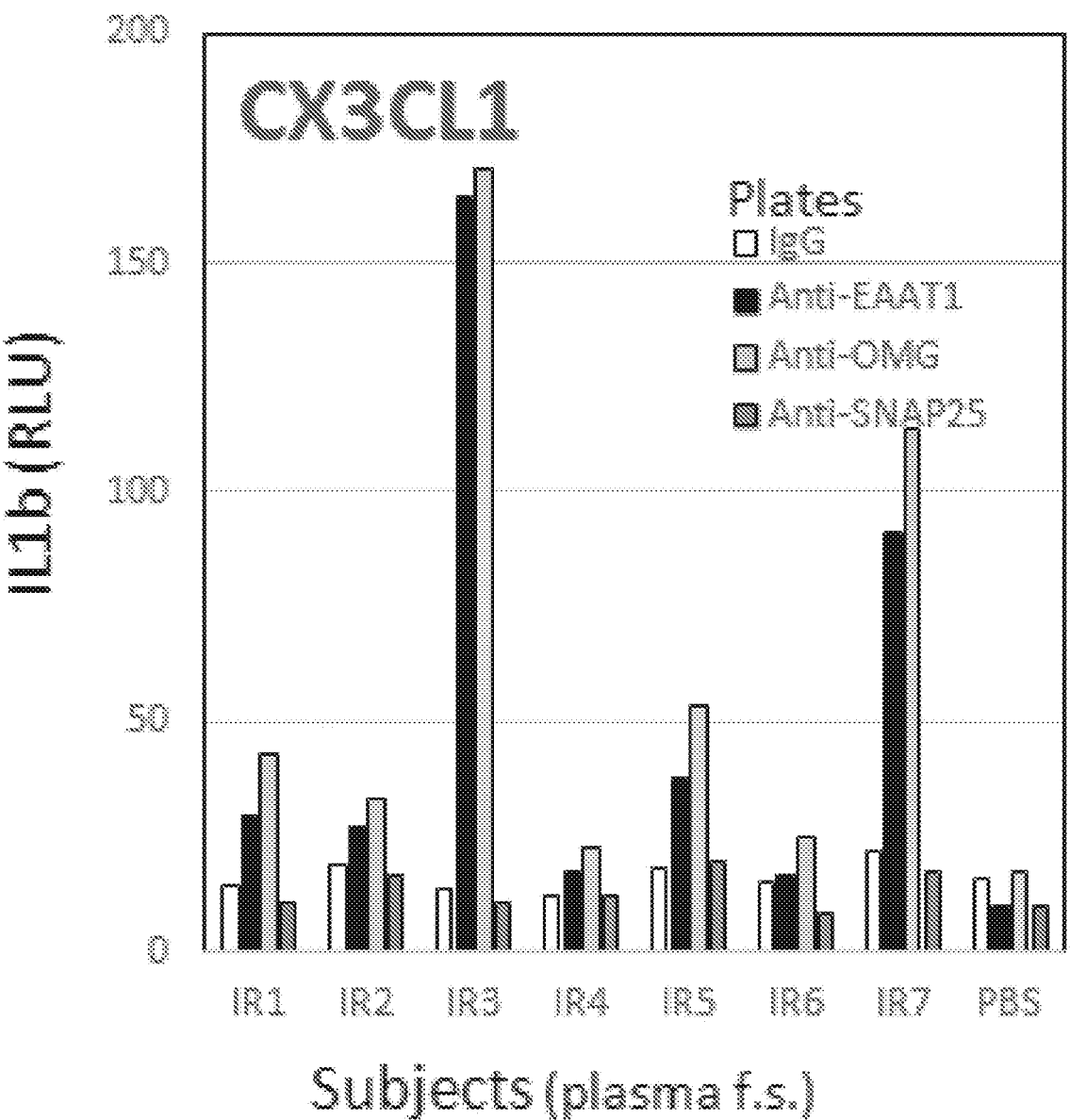

As shown in FIGS. 10A, 10C, and 10E, standard plasma showed volume dependent increases in IL1b, IL34 and CX3CL1 levels on SNAP25, EAAT1, and OMG ELISA plates compared to control IgG-immobilized plates. IL1b and IL34 on anti-OMG-immobilized plates were saturated at 2.5% plasma (see FIGS. 10A and 10C).

Plasma samples (IR1, IR4, IR6) were negative for IL1b, IL34, and CX3CL1, similar to those of negative control PBS alone. However, IR2 was IL1b positive on the SNAP25 ELISA plate, and IR3 was CX3CL1 positive on EAAT1 and OMG ELISA plates. IR5 showed positive IL1b levels and IL34 on SNAP25 plates, and detectable levels of CX3CL1 on EAAT1 and OMG ELISA plates. IR7 showed positive IL1b on all ELISA plates, IL34 on SNAP25 ELISA plate, and detectable levels of CX3CL1 on both EAAT1 and OMG ELISA plates.

These results showed that methods of the present invention are useful for detecting cytokines (IL1b and IL34) and chemokines (CX3CL1) on the surface of exosomes (SNAP25+ NDE, EAAT1+ ADE, and OMG+ ODE). These results also showed that cytokine and chemokine profiles are unique to each subset of brain-derived exosomes (NDE, ADE, and ODE). These results showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing neurological disease in a subject. These results further suggested that the methods and compositions of the present invention would be useful for diagnosing a disease or disorder.

Example 11: Detection of Membrane Proteins and Receptors on the Surface of Exosomes Multiple membrane proteins and receptors were detected on the surface of exosomes as follows. Various antibodies were suspended in a coating buffer, and applied to an ELISA plate. After an hour of incubation, each well was washed once, then blocking solution (0.5% BSA in Blocker casein) was added, and incubation was continued for an additional hour. After washing each well twice, plasma or buffer control (phosphate buffered saline, PBS) was added, then incubation was continued in a refrigerator overnight. After washing each well twice, biotinylated anti-CD81 or anti-SNAP25 was added and incubation was continued for an hour. After washing each well twice, streptavidin-horserad-ish peroxidase was added, and incubation was continued for another 30 minutes. After washing each well three times, SuperSignal substrate was added and chemiluminescent signals were measured in a luminometer.

As shown in Table 2 below, multiple cytosolic proteins, secretary proteins, and membrane proteins and receptors were detected on the surface of exosomes.

TABLE 2

Antibody immobilization, probed with CD81/SNAP25.

| Experiment | Categories | Targets (immobilization) | | Probes | samples applied | | | Clinical area |
|---|---|---|---|---|---|---|---|---|
| | | | | | PBS (RLU) | Plasma (RLU) | Positive (O) | |
| Exp-1160 | Control | IgG | | | 6.5 | 36 | | |
| | | CD81 | | CD81 | 3.7 | 1,443 | O | |
| | Cytoslic proteins | CTSD | Cathepsin D | | 9.9 | 226 | O | Neurology, oncology |
| | | NRGN (R&D) | neurogranin | | 6.4 | 91 | | Neurology |
| | | NRGN (BioLegend) | | | 6.4 | 592 | | Neurology |
| | Membrane proteins | PD-L1 | Programmed death-ligand 1 | | 7.2 | 453 | O | Immunology, oncology |
| | | ErbB2 | v-erb-b2 erythroblastic leukemia viral oncogene homolog 2 | | 185.4 | 193 | O | Immunology, oncology |
| | | RBC | Red blood cells | | 3.5 | 674 | O | Hematology |
| | | NCAM | Neural cell adhesion molecule | | 3.8 | 179 | O | Immunology, oncology |
| | | CD11b | | | 4.8 | 415 | O | Immunology, oncology |
| | | CD11a | | | 2.4 | 745 | O | Immunology, oncology |
| | | CD16 | | | 4.5 | 40 | O | Immunology, oncology |
| | | CD28 | | | 3.8 | 392 | O | Immunology, oncology |
| | | CD79a | | | 3.2 | 351 | O | Immunology, oncology |
| | | TCR ab | T cell receptor | | 20.8 | 47 | | Immunology, oncology |
| | | TCR γd | | | 5.3 | 815 | O | Immunology, oncology |
| | | CD32 | | | 5.5 | 36 | | Immunology, oncology |
| Exp-1193 | Control | IgG | | CD81 | 4.0 | 20 | | |
| | | SNAP | | | 1.4 | 1,618 | O | Neurology |
| | | CD81 | | | 1.5 | 1,075 | O | Neurology |
| | Cytosolic proteins | REST | | | 2.6 | 1,724 | O | Neurology |
| | | SYP | synaptophysin | | 1.4 | 1,963 | O | Neurology |
| | | SYT | synaptotagmin | | 2.0 | 1,309 | O | Neurology |
| | | SYMPO | synaptopodin | | 1.8 | 3,051 | O | Neurology |
| | | SYN | synapsin | | 1.6 | 85 | | Neurology |
| | | NEFL | neurofilamant light chain | | 1.3 | 2,711 | O | Neurology |
| Exp-1203-1 | Control | NRGN (Santa Cruz) | | SNAP25 | 4.0 | 1,275 | O | Neurology |
| | | SNAP25 | | | 2.8 | 375 | O | Neurology, oncology |
| | | IgG | | | 3.8 | 5 | | |
| | Cytosolic proteins | Caspase 3 | | | 3.0 | 364 | O | Neurology, oncology |
| | | GYS | Glycogen synthase 1 | | 3.5 | 111 | O | Neurology |
| | | Ubiquitin | | | 3.0 | 388 | O | Neurology |
| | | HSP70 | | | 8.8 | 289 | O | Neurology |
| | | Beta amyloid | | | 2.8 | 394 | O | Neurology |
| | Secretary proteins | CCL2 | | | 2.8 | 208 | O | Neurology, immunology |
| | | IL8 | interleukin 8 | | 2.5 | 344 | O | Neurology, immunology |
| | | IL12B | | | 2.8 | 163 | O | Neurology, immunology |
| | | IL16 | | | 3.4 | 185 | O | Neurology, immunology |
| | | Orexin | | | 2.2 | 2 | | Neurology |
| | Membrane proteins | Insulin Receptor | | | 3.2 | 364 | O | Neurology, metabolic |
| | | TRAIL | Tumor necrosis factor ligand superfamily member 10 | | 3.3 | 346 | O | Neurology, oncology |
| | | TNF Receptor 1 | | | 2.5 | 214 | O | Neurology, oncology |
| | | Death Receptor 5 | | | 3.1 | 309 | O | Neurology, oncology |
| | | Death Receptor 6 | | | 3.8 | 82 | O | Neurology, oncology |
| | | Cannabinoid receptor-1 | | | 2.3 | 2 | | Neurology |

TABLE 2-continued

Antibody immobilization, probed with CD81/SNAP25.

| Experiment | Categories | Targets (immobilization) | Probes | samples applied | | | Clinical area |
| | | | | PBS (RLU) | Plasma (RLU) | Positive (O) | |
|---|---|---|---|---|---|---|---|
| | | Orexin receptor | | 2.4 | 547 | O | Neurology |
| | | Dopamin receptor D1 | | 2.4 | 280 | O | Neurology |
| | | Dopamin receptor D2 | | 2.1 | 255 | O | Neurology |
| | | Serotonin receptor 2A | | 2.8 | 267 | O | Neurology |
| Exp-1203-2 | Control | SNAP25 | SNAP25 | 4.1 | 389 | O | |
| | | IgG | | 5.2 | 8 | | |
| | Cytosolic proteins | Dopa decarboxylase | | 6.8 | 7 | | |
| | Secretory proteins | Enkephalin | | 6.5 | 174 | O | Neurology |
| | | Nociceptin | | 5.5 | 123 | O | Neurology |
| | Membrane proteins | Serotonin receptor 2C | | 4.6 | 366 | O | Neurology |
| | | Serotonin receptor 3B | | 3.9 | 432 | O | Neurology |
| | | GABA receptor 1-6 | | 5.1 | 349 | O | Neurology |
| | | GABA Receptor-5 | | 5.4 | 130 | O | Neurology |
| | | GABA Receptor B1 | | 4.5 | 423 | O | Neurology |
| | | GABA Receptor B2 | | 4.8 | 384 | O | Neurology |
| | | Opioid receptor KOR | | 6.1 | 349 | O | Neurology |
| | | Glutamate receptor-1 | | 6.0 | 256 | O | Neurology |
| | | Glutamate receptor-2 | | 7.4 | 232 | O | Neurology |
| Exp-1206 | Control | SNAP | SNAP25 | 1.9 | 417 | O | Neurology |
| | | IgG | | 2.4 | 2 | | |
| | Cytosolic proteins | LAMP1 | Lysosome-associated membrane glycoprotein 1 | 0.9 | 310 | O | Neurology |
| | | PSEN1 | Presenilin-1 | 1.0 | 320 | O | Neurology |
| | | BACE | be-ta secretase | 2.5 | 299 | O | Neurology |
| | | TREM2 | Triggering receptor expressed on myeloid cells 2 | 3.0 | 319 | O | Neurology |
| | | AchE | Acetylcholinesterase | 3.6 | 267 | O | Neurology |
| | | GSK | Glycogen synthase kinase | 1.6 | 258 | O | Neurology |
| | | IL6 | | 3.2 | 365 | O | Neurology, immunology |
| | | TNFa | tumor necrosis factor | 0.8 | 404 | O | Neurology, immunology |
| | | CX3CL1 | | 0.9 | 360 | O | Neurology, immunology |
| Exp-1220 | Control | IgG | CD81 | 6.1 | 120 | O | Neurology |
| | | CD81 (1.3.3.22) | | 3.0 | 2,773 | O | |
| | | CD81 (5A6) (BioL) | | 5.0 | 886 | O | |
| | | CD81 (D4) | | 3.2 | 1,938 | O | |
| | | CD81 (5A6) SC | | 6.3 | 3,162 | O | |
| | | CD81 (B11) | | 2.1 | 3,280 | O | |
| | | CD81 (BD) | | 4.7 | 3,064 | O | |
| | | CD61 (Sino) | | 10.8 | 1,858 | O | |
| | | CD63 (MX49.129) | | 5.7 | 2,629 | O | |
| | | SNAP25 | | 2.8 | 3,712 | O | |
| | Cytosolic proteins | ACTB | beta-actin | 16.1 | 1,968 | O | Neurology |
| | | SNCA | alpha synuclein | 3.3 | 2,608 | O | Neurology |
| | Secretory proteins | GnRH | Gonadotropin-releasing hormone | 2.3 | 3,424 | O | Neurology, endocrinology |
| | Membrane proteins | CD171 U1127.11 | | 2.0 | 3,331 | O | |
| | | CD171 D5 | | 2.9 | 2,111 | O | |
| | | CD171 (eBio) | | 4.2 | 49 | | |
| | | CTSD (SC) | cathepsin D | 10.6 | 349 | O | Neurology, oncology |
| | | CTSD (R&D) | | 6.4 | 350 | O | Neurology, oncology |

TABLE 2-continued

Antibody immobilization, probed with CD81/SNAP25.

| Experiment | Categories | Targets (immobilization) | | Probes | samples applied | | | Clinical area |
|---|---|---|---|---|---|---|---|---|
| | | | | | PBS (RLU) | Plasma (RLU) | Positive (O) | |
| | | EpCAM | Epithelial cell adhesion molecule | | 1.9 | 3,655 | O | Oncology |
| | | CK19 | cytokeratin 19 | | 2.4 | 3,255 | O | Oncology |
| | | IgG | | SNAP25 | 3.2 | 4 | O | |
| | | CD81 (1.3.3.22) | | | 1.7 | 159 | O | |
| | | CD81 (5A6) (BioL) | | | 1.5 | 71 | O | |
| | | CD81 (D4) | | | 1.5 | 157 | O | |
| | | CD81 (5A6) SC | | | 4.0 | 340 | O | |
| | | CD81 (B11) | | | 1.6 | 332 | O | |
| | | CD81 (JS81) (BD) | | | 1.7 | 361 | O | |
| | | CD61 (Sino) | | | 1.4 | 108 | O | |
| | | CD63 (MX49.129) | | | 2.0 | 243 | O | |
| | | SNAP25 | | | 1.1 | 277 | O | |
| Exp-1225 | | IgG | | CD81 | 3.0 | 11 | O | |
| | | CD81 | | | 2.1 | 315 | O | |
| | | PLAP | Alkaline phosphatase, placental | | 2.7 | 19 | O | OBGYN |
| | | CSH1 | Chorionic somatomammotropin hormone 1 | | 2.5 | 32 | O | OBGYN |
| | | PSG1 | Pregnancy-specific beta-1-glycoprotein 1 | | 2.3 | 16 | O | OBGYN |
| | | FasL | Tumor necrosis factor superfamily 6 | | 2.9 | 67 | O | OBGYN, oncology |

To confirm the proteins detected in Table 2 above, a second series of experiments were performed as follow. Positive antibodies were biotinylated, and used on the ELISA where PBS or plasma was applied to anti-SNAP25–, or control IgG-immobilized plates. As shown in Table 3 below, all positive antibodies in Table 2 were also positive in this series of experiments.

TABLE 3

Anti-SNAP25 or control IgG-immobilized plate, probed with various biotinylated antibodies.

| Experiment | Categories | Target (biotinylated probes) | Immobilized | PBS (RLU) | Plasma (RLU) | Positive (O) |
|---|---|---|---|---|---|---|
| | | | | samples applied | | |
| Exp-1197 | Control | SNAP | SNAP25 | 2.5 | 405 | O |
| | | CD81 | | 3.2 | 4503 | O |
| | Cytosolic proteins | REST | | 2.9 | 30 | O |
| | | SYP | | 2.9 | 226 | O |
| | | SYT | | 3.5 | 92 | O |
| | | SYMPO | | 2.7 | 28 | O |
| | | NEFL | | 2.6 | 82 | O |
| | | NRGN | | 2.3 | 50 | O |
| Exp-1205 | Control | PBS | IgG | 0.3 | 0.3 | |
| | Cytosolic proteins | Tau | | 4.7 | 11.1 | |
| | | Abeta | | 7.1 | 10.6 | |
| | | Caspase | | 1.2 | 2.8 | |
| | | HSP | | 1.2 | 7.3 | |
| | | ubiquitin | | 1.3 | 5.2 | |
| | | GYS | | 7.7 | 15.6 | |
| | Secretary proteins | CCL2 | | 3.4 | 7.3 | |
| | | IL8 | | 1.0 | 8.7 | |
| | | IL12B | | 0.8 | 6.1 | |
| | | IL16 | | 10.1 | 12.3 | |
| | Membrane proteins | DRD1 | | 5.9 | 7.1 | |
| | | SR2A | | 4.8 | 6.1 | |
| | | SR2C | | 1.0 | 4.3 | |
| | | TNFR1 | | 0.9 | 2.3 | |
| | | DR6 | | 12.2 | 12.3 | |
| | Control | PBS | SNAP25 | 0.2 | 0 | |
| | Cytosolic proteins | Tau | | 2.5 | 1085 | O |
| | | Abeta | | 2.1 | 1259 | O |
| | | Caspase | | 1.0 | 396 | O |
| | | HSP | | 0.9 | 1403 | O |
| | | ubiquitin | | 1.2 | 692 | O |
| | | GYS | | 2.0 | 1338 | O |
| | Secretary proteins | CCL2 | | 2.0 | 580 | O |
| | | IL8 | | 0.5 | 1256 | O |
| | | IL12B | | 0.4 | 670 | O |
| | | IL16 | | 3.7 | 724 | O |
| | Membrane proteins | DRD1 | | 2.1 | 489 | O |
| | | SR2A | | 1.6 | 495 | O |
| | | SR2C | | 0.9 | 672 | O |
| | | TNFR1 | | 0.4 | 499 | O |
| | | DR6 | | 3.6 | 953 | O |
| Exp-1207 | Control | PBS | IgG | 1.5 | 1.1 | |
| | | CD81 | | 0.9 | 7.7 | |
| | | SNAP25 | | 1.3 | 1.1 | |
| | Cytosolic proteins | LAMP1 | | 1.2 | 2.0 | |
| | | PSEN1 | | 3.3 | 5.6 | |
| | | BACE | | 3.5 | 2.2 | |
| | | AchE | | 3.2 | 3.5 | |
| | Secretary proteins | IL6 | | 17.3 | 2.4 | |
| | | TNFa | | 0.5 | 1.0 | |
| | | CX3CL1 | | 0.6 | 1.6 | |
| | | ENK | | 3.6 | 3.7 | |
| | Membrane proteins | OR | | 3.4 | 2.4 | |
| | | DRD2 | | 1.4 | 1.8 | |
| | | KOR | | 2.5 | 2.5 | |
| | | TREM2 | | 2.1 | 2.2 | |
| | Control | PBS | SNAP25 | 1.1 | 0 | |
| | | CD81 | | 1.2 | 2844 | O |
| | | SNAP25 | | 0.4 | 227 | O |
| | Cytosolic proteins | LAMP1 | | 0.3 | 250 | O |
| | | PSEN1 | | 1.3 | 334 | O |
| | | BACE | | 1.1 | 267 | O |
| | | AchE | | 1.1 | 381 | O |

TABLE 3-continued

Anti-SNAP25 or control IgG-immobilized plate, probed with various biotinylated antibodies.

| Experiment | Categories | Target (biotinylated probes) | Immobilized | samples applied | | |
| | | | | PBS (RLU) | Plasma (RLU) | Positive (O) |
|---|---|---|---|---|---|---|
| | Secretary proteins | IL6 | | 4.3 | 440 | O |
| | | TNFa | | 0.5 | 704 | O |
| | | CX3CL1 | | 0.5 | 988 | O |
| | | ENK | | 1.0 | 1257 | O |
| | Membrane proteins | OR | | 1.1 | 543 | O |
| | | DRD2 | | 0.5 | 437 | O |
| | | KOR | | 0.7 | 563 | O |
| | | TREM2 | | 0.9 | 638 | O |

These results showed that methods of the present invention are useful for detecting cytosolic proteins, secretary proteins, and membrane proteins and receptors on the surface of exosomes. These results showed that the methods and compositions of the present invention are useful for identifying, detecting, and measuring biomarkers on exosomes, wherein the exosomes are not lysed or permeabilized. These results further suggested that the methods and compositions of the present invention would be useful for diagnosing neurological disease in a subject. These results further suggested that the methods and compositions of the present invention would be useful for diagnosing a disease or disorder.

Example 12: Quantification Standards for Multi-Target ELISA

Figure 11:
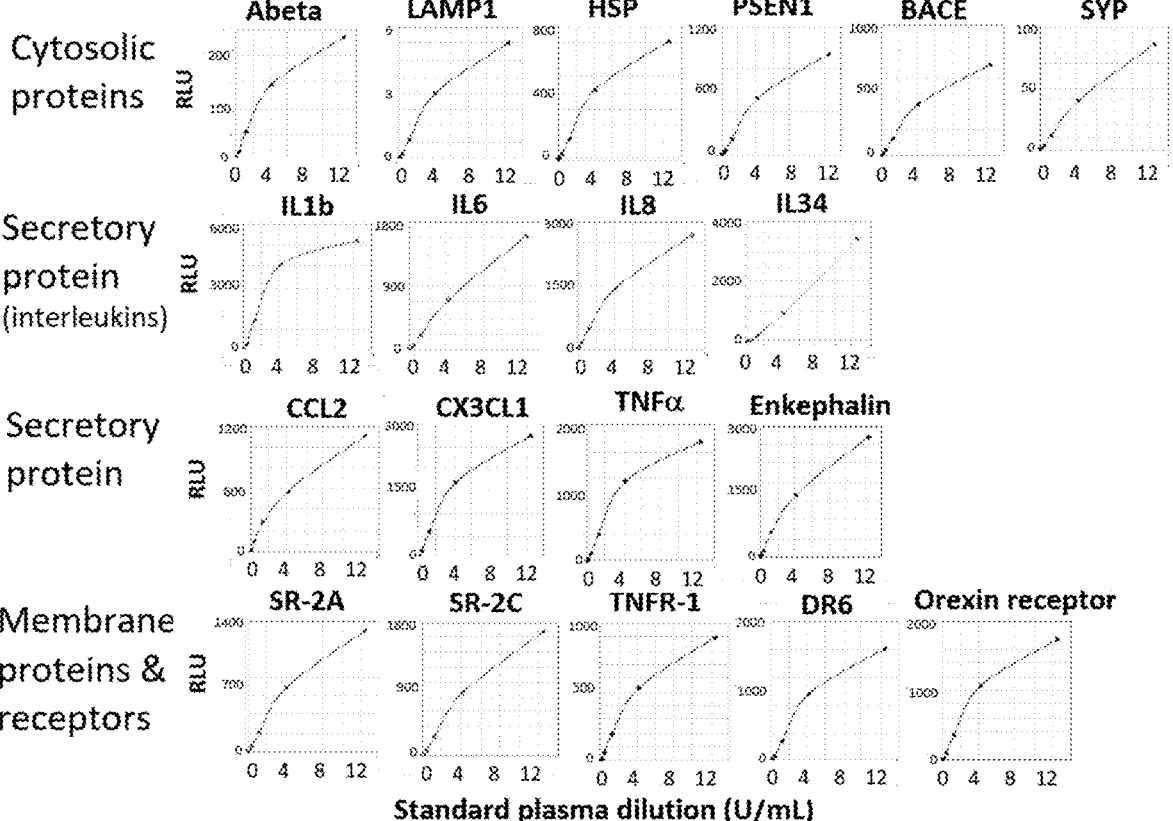
FIG. 11 sets forth data showing dilution of standard plasma as an ELISA quantification standard.

ELISA assays require quantification standards to determine levels of target molecules in a test sample. The exemplary assays of the present invention utilize two antibodies against different target molecules. Accordingly, purified or recombinant proteins are not applicable as a standard for such ELISA assays. Thus, various plasma samples were screened, and one particular plasma sample was selected, for having high values of exosomes including NDE, ADE, and ODE positive exosomes. This plasma sample was subsequently used as a quantification standard. As shown in FIG. 11, this plasma sample performed well as a standard for multiple ELISAs of the present invention. A standard curve was generated for each target by using four parameter logistic regression analysis.

Example 13: Differential Diagnosis of Alzheimer's Disease and Mild Cognitive Impairment in Humans The methods and compositions of the present invention were used for differential diagnosis of Alzheimer's disease and mild cognitive impairment in biological samples from humans as follows. Anti-SNAP25 antibodies were immobilized on an ELISA plate. Eight samples of EDTA plasma from subjects having Alzheimer's disease (AD, n=4) or mild cognitive impairment (MCI, n=4) and eight age and gender-matched controls were applied to ELISA wells, and antibodies against 16 cytosolic proteins, secretary proteins, and membrane proteins and receptors were used as detection antibodies (FIG. 12).

Figure 12:
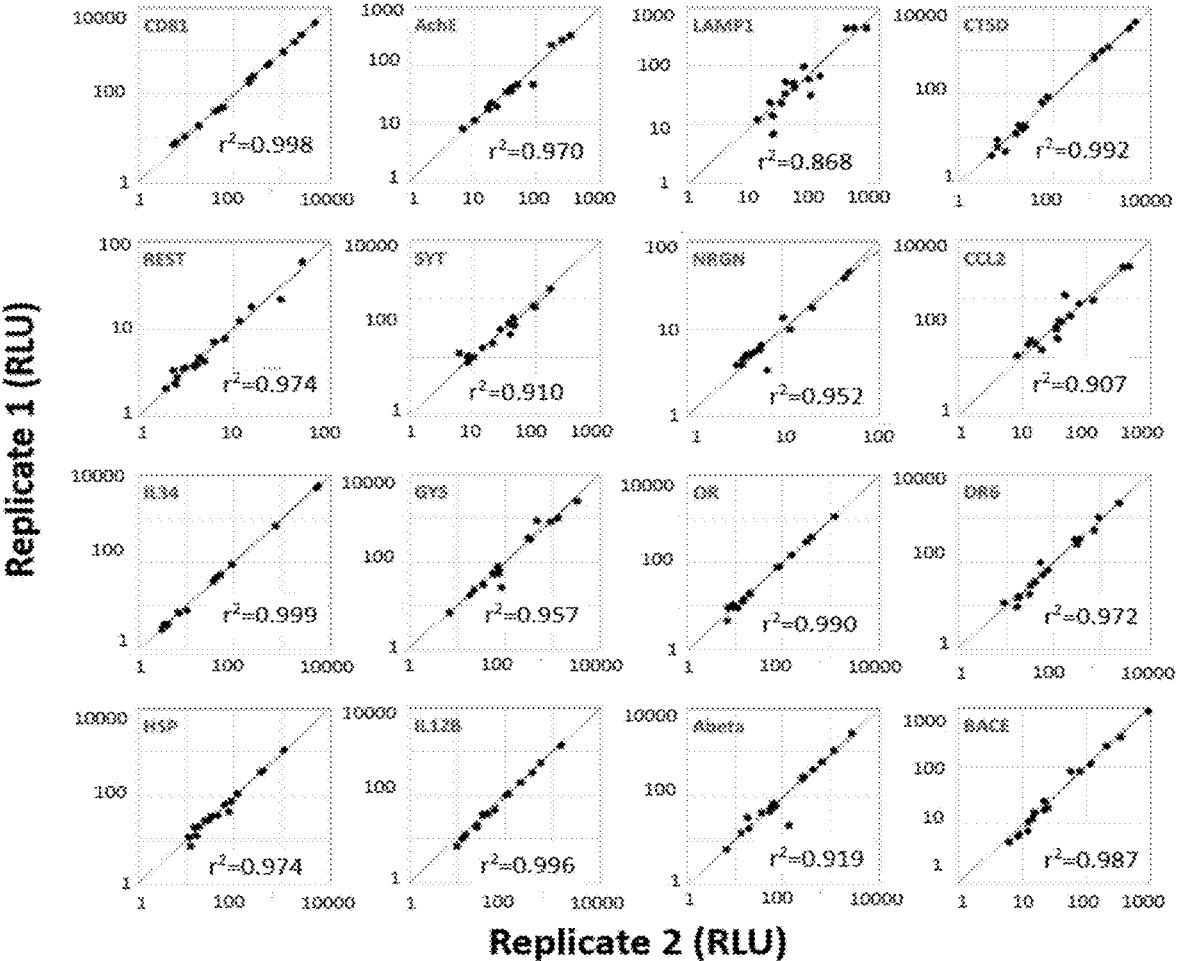
FIG. 12 sets forth data showing duplicate variation for plasma levels of 16 exosomal biomarkers of the present invention.
Figure 13:
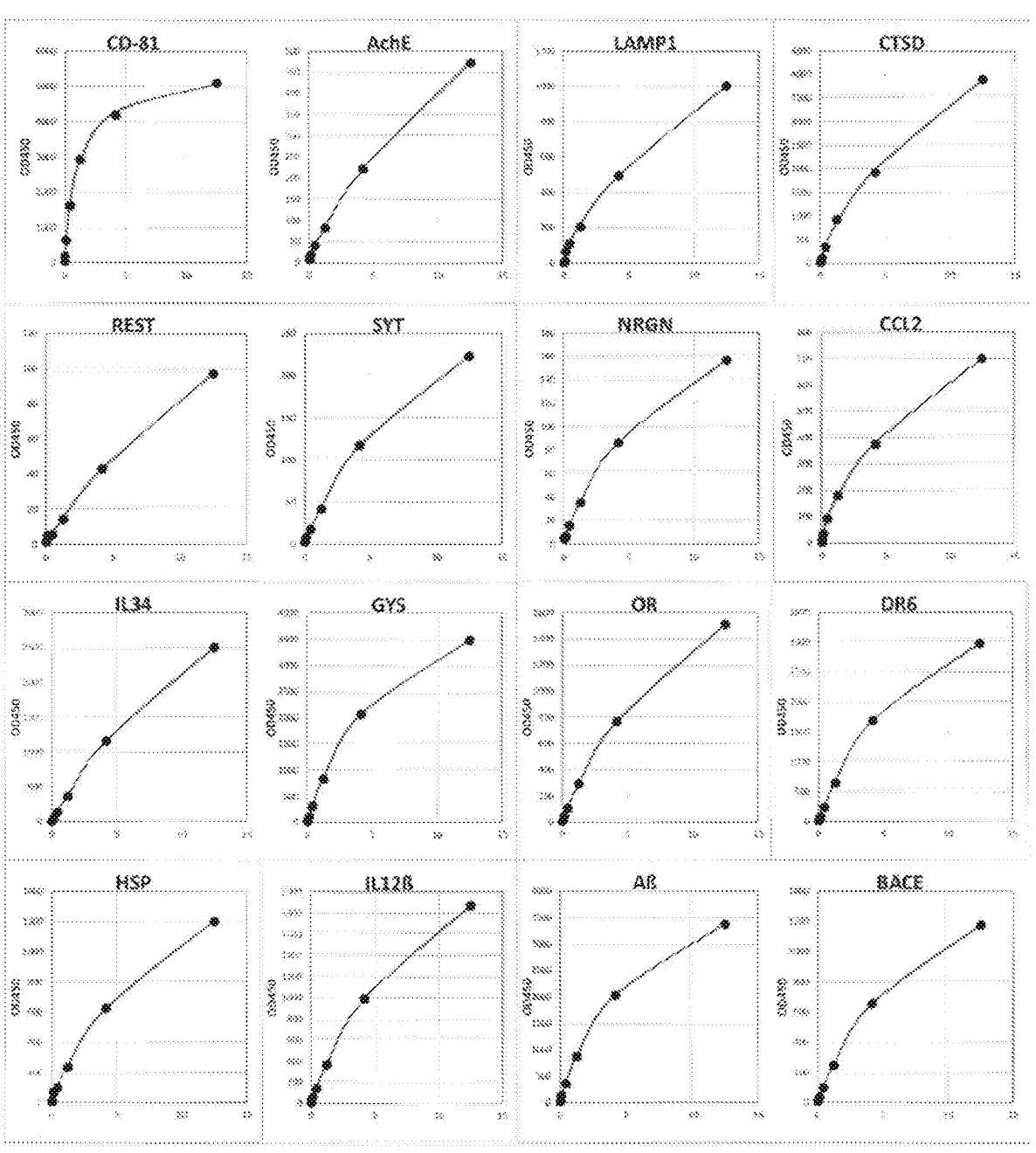
FIG. 13 sets forth data showing standard curves for plasma levels of 16 exosomal biomarkers of the present invention.
Figure 14:
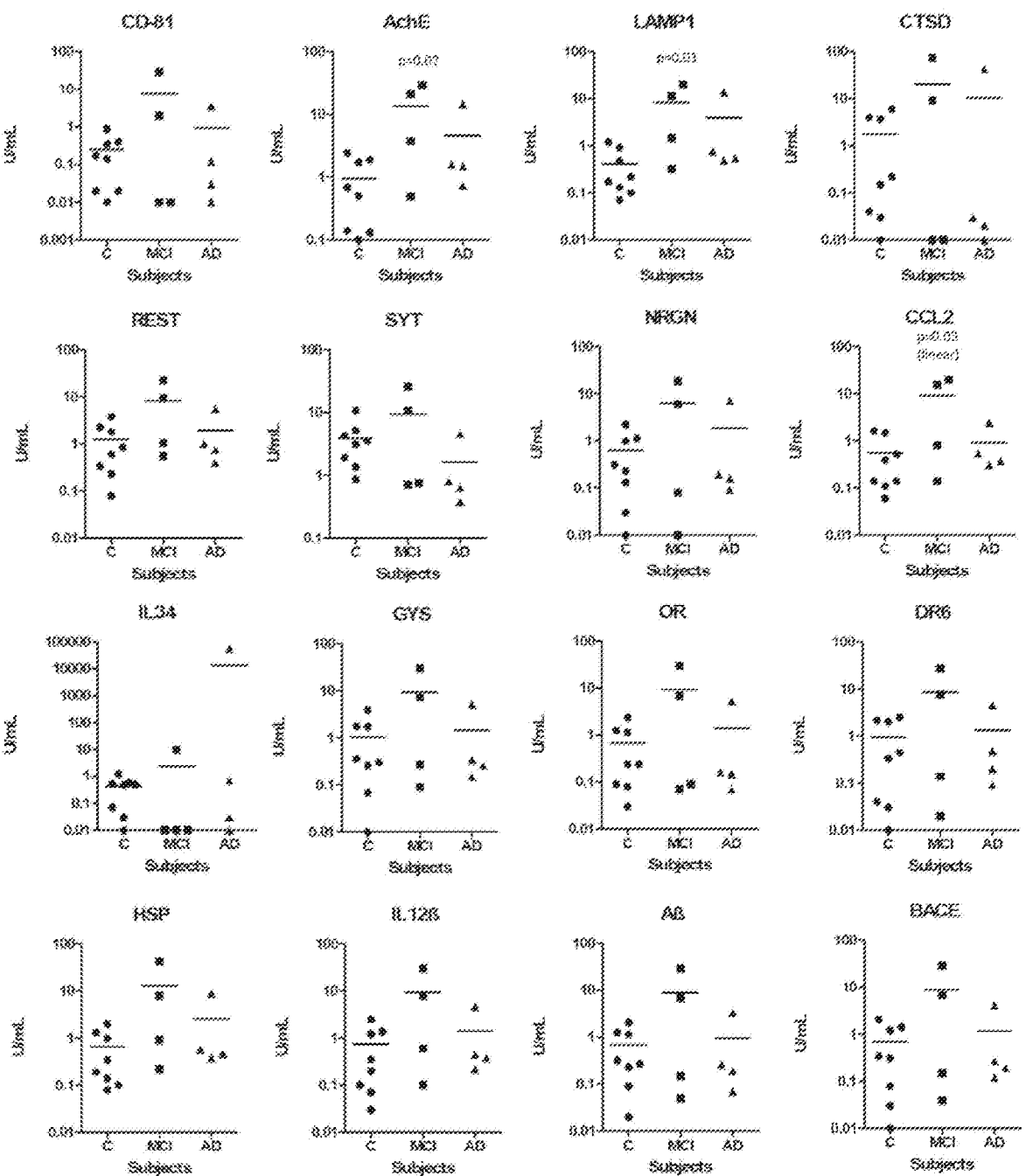
FIG. 14 sets forth data showing quantification of target exosomal surface protein biomarkers in plasma.

As shown in FIG. 12, duplicate variation for all 16 biomarkers was small. FIG. 13 shows the standard curves for all 16 biomarkers. Quantification of target surface protein biomarkers is shown in FIG. 14. As shown in FIG. 14, AchE, LAMP1, and CCL2 levels were significantly higher in MCI compared to control sample levels. These results showed that the methods and compositions of the present invention could be used to diagnose MCI and for the differential diagnosis of Alzheimer's disease and MCI.

Figure 15:
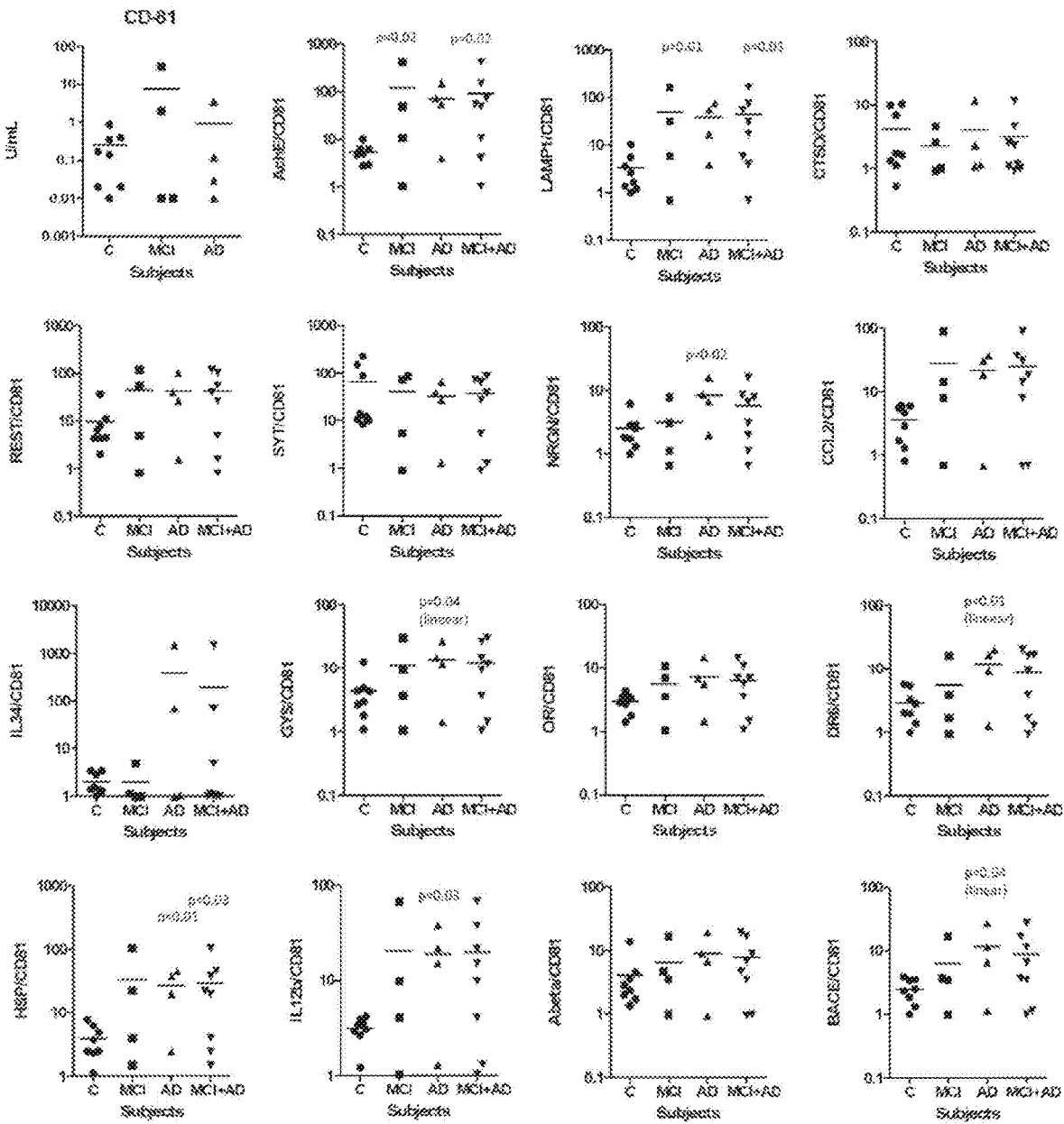
FIG. 15 sets forth data showing plasma exosomal bio-marker levels normalized to CD81.

To account for variability in CD81 levels in the plasma samples, the remaining 15 exosomal biomarker levels were normalized by CD81 levels. As shown in FIG. 15, AchE and LAMP1 levels were significantly greater in plasma samples from subjects with MCI and AD+MCI compared to control samples. Additionally, NGRN, GYS, DR6, HSP, IL12b, and BACE levels were significantly different between AD, MCI, AD+MCI and control samples. These results showed that the methods and compositions of the present invention could be used to diagnose AD, MCI, and for differential diagnosis of AD and MCI.

Figure 16:
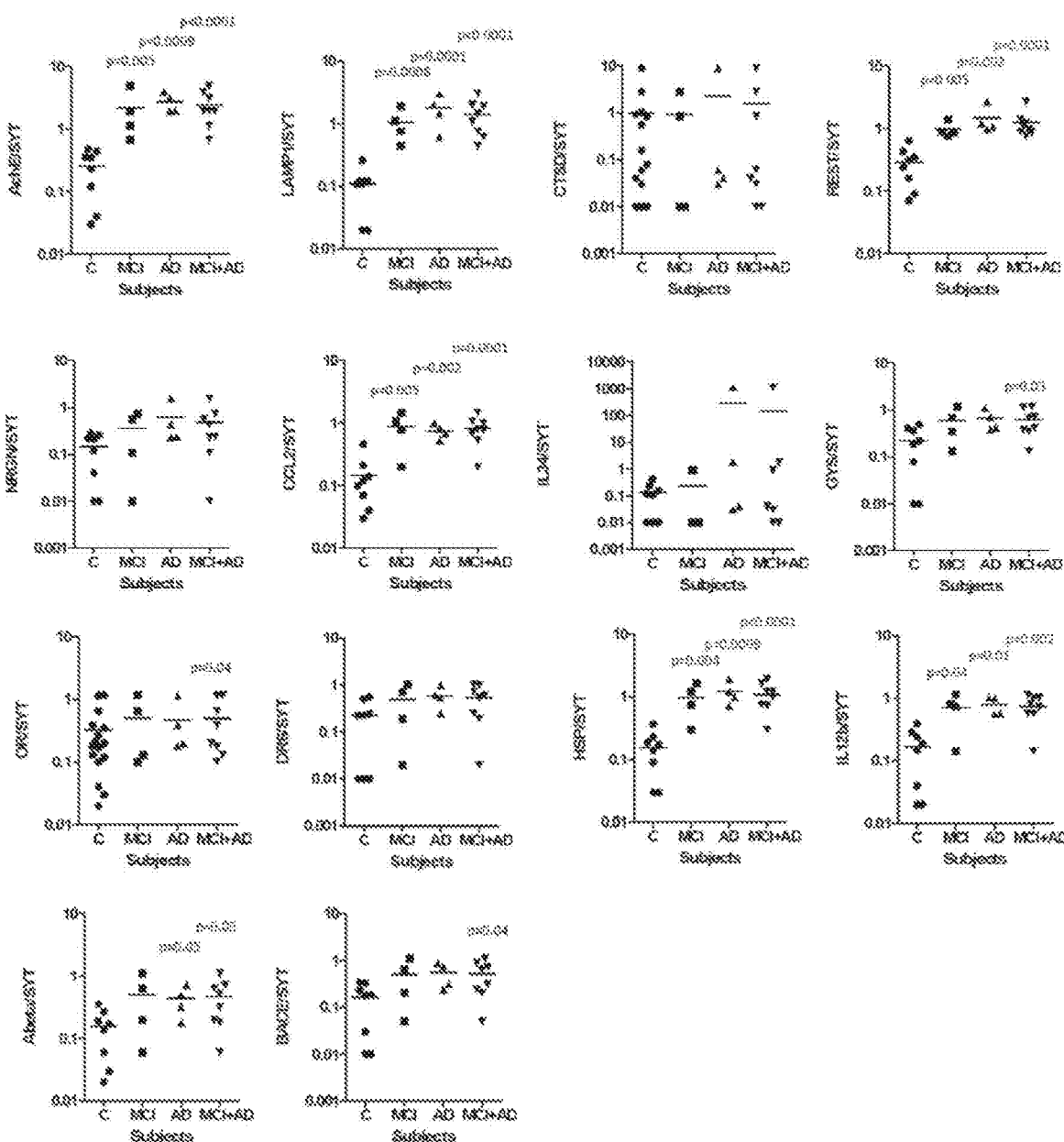
FIG. 16 sets forth data showing plasma exosomal bio-marker levels normalized to SYT.

In another series of experiments, the target biomarker levels in the plasma samples assayed above were normalized to SYT levels. Since neural-derived exosomes were captured by SNAP25-immobilized plates, the SYT normalization results in a second normalization of neuron markers. As shown in FIG. 16, AchE/SYT, LAMP1/SYT, REST/SYT, CCL2/SYT, HSP/SYT, and IL12b/SYT levels were significantly different between AD, MCI, AD+MCI, and control samples. These results showed that the methods and compositions of the present invention could be used to diagnose AD, MCI, and for differential diagnosis of AD and MCI. These results further suggested that the methods and compositions of the present invention would be useful for diagnosing a disease or disorder.

Example 14: Enumeration of Brain-Derived Exosomes in Human Subjects with Parkinsonism-Plus Syndromes The methods and compositions of the present invention were used to enumerate the plasma levels of neuron-derived, astrocyte-derived, and oligodendrocyte-derived exosomes (NDEs, ADEs and ODEs, respectively) obtained from patients with Parkinson's Disease (PD), multiple system atrophy (MSA), progressive supranuclear palsy (PSP) and control subjects as follows. A total of 52 subjects, including 15 patients with PD (ages 46-79, mean±SD of 64.7±10.8, 9 male and 6 female), 15 patients with MSA (ages 44-74, mean±SD of 63.3±8.16, 10 male and 5 female), 7 patients with PSP (ages 58-81, mean±SD of 71.6±9.8, 2 male and 5 female), and 15 disease controls (ages 47-77, mean±SD of 64.7±8.5, 10 male and 5 female) were included in this study, and these groups were age-matched.

Plasma samples were taken through venous puncture, and a total of 8 mL of blood was collected in EDTA-containing tubes. After collection, plasma was separated by centrifugation for 15 min at 2,000 g and distributed in polypropylene vials, then stored at $-80°$ C. until analysis.

Various concentrations of antibodies were suspended in 1× coating buffer (BioLegend, San Diego, CA), and 50 μL was applied to each well of a white flat bottom strip microplate (Sigma-Aldrich, St. Louise, MO). After 1-hour incubation at room temperature, each well was washed with 1× wash buffer (BioLegend), then 75 μL of blocker casein (Thermo Fisher Scientific, Waltham, MA), supplemented with 1% blocker bovine serum albumin (BSA) (Thermo Fisher) was added, and incubation was continued for an another 1 hour. After washing each well, each plate was used immediately for enzyme-linked immunosorbent assay (ELISA).

Forty uL each of standards, controls, and plasma samples were applied to each well of ELISA plates, and incubated in a refrigerator overnight. Next day, after each well was washed, 40 uL of biotinylated detection antibodies suspended in phosphate buffered saline, pH 7.4 (PBS) supplemented with 0.1% tween-20 (Sigma-Aldrich), 1% blocker BSA (Thermo Fisher), 8 ug/mL mouse IgG (Equitech-Bio, Kerrville, TX) was added, and incubated at room temperature for 1 hour. After incubation, each well was washed, then 40 μL of streptavidin-horseradish peroxidase (SA-HRP) (Thermo Fisher) suspended in PBS supplemented with 0.1% Tween-20, 1% blocker BSA (Thermo Fisher), and 5% blocker casein was applied. After 30 min incubation, each well was washed, then 50 L of substrate (SuperSignal, Thermo) was applied. After 4-min incubation, chemiluminescent signals (relative light units, RLU) was determined in a luminometer (ANSH Labs, Webster, TX).

Since our sandwich ELISA used a combination of 2 different target antibodies, such as anti-CD81 and anti-SNAP25 (synaptosomal-associated protein 25), purified or recombinant protein was not applicable as a quantification standard. Thus, we first screened various plasma samples obtained from commercial sources (Innovative Research, Novi, MI, and EquiTech Enterprise, Kerrville, TX), and found plasma samples with high concentrations of all of NDE, ADE, and ODE. By assigning 100 units/mL to this plasma, dilution study was carried out in each ELISA to obtain RLU in each dilution. Then using 4 parameter logistic analysis, RLU of each sample was converted to units/mL.

Figure 17:
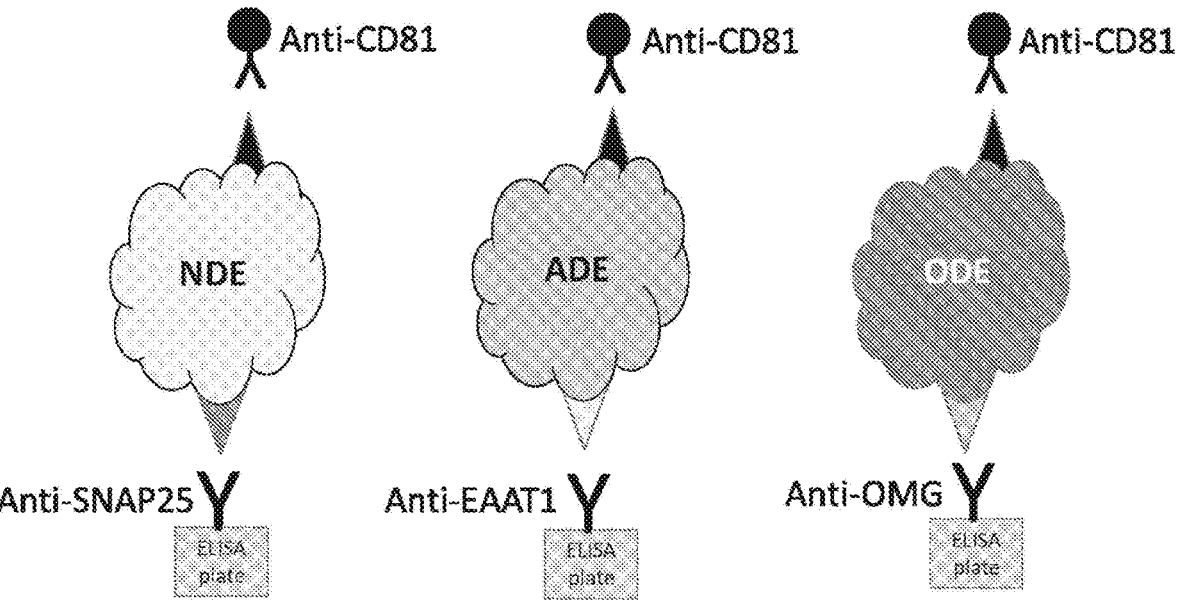
FIG. 17 sets forth data showing the principle of an exemplary assay of the present invention. NDE, ADE, and ODE are specifically captured on ELISA plates, where anti-SNAP25 (neuron marker), anti-EAAT1 (astrocyte marker), and anti-OMG (oligodedrocyte marker) are immo-bilized. Captured exosomes were further probed with bioti-nylated anti-CD81 (exosome common marker).

In order to find antibodies against NDE, ADE, and ODE in plasma, various dilutions of plasma were applied to anti-CD81 monoclonal antibody (clone JS-81, BD Biosciences, Sparks, MD)-immobilized ELISA plates to capture whole exosomes as well as control mouse IgG (Santa Cruz Biotechnology, Dallas, Texas)-immobilized ELISA plate to be used as a negative control. After extensive washing step to remove any non-bound materials from each well, biotinylated antibodies against various targets were applied, and ELISA was carried out as described above. For biotinylation, we used EZ-Link Sulfo-NHS-LC-Biotin (Thermo, Rockford, USA). From this, we found that monoclonal antibody against SNAP25 (clone B-8, Santa Cruz Biotechnology), polyclonal antibodies against excitatory amino acid transporter 1 (EAAT1) (=glutamate aspartate transporter (GLAST)) and oligodendrocyte-myelin glycoprotein (OMG) (Bioss Antibodies, Woburn, MA), showed very strong signals on CD81-immobilized plates, not on control mouse IgG-immobilized plates. After discovery of appropriate antibodies, anti-SNAP25, anti-EAAT1, and anti-OMG were immobilized onto ELISA plates, then probed with biotinylated anti-CD81 (Clone 1.3.3.22, LS Bio, Seattle, WA). We called NDE for SNAP25$^+$, CD81$^+$ ELISA results, ADE for EAAT1$^+$, CD81$^+$ ELISA results, and ODE for OMG$^+$, CD81$^+$ ELISA results, respectively (FIG. 17).

Logarithmic transformations of measured values of BDE were used as appropriate to a particular analysis to reduce excessive skewing and outlier influence in analyses for group differences and regressions between parameters. The mean differences in BDE between diagnostic groups and the regressions between the levels of BDE and clinical parameters were assessed by t-test (Excel). Because the number of samples was limited, additional non-parametric Mann-Whitney U test was performed (Prism, GraphPad, La Jolla, CA). We also derived receiver operating characteristics (ROC) curves for the diagnosis of PD using the levels of BDE as the predictor, and estimated the area under the curve (AUC; AUC=0.5 indicates no discrimination and AUC=1 would indicate a perfect diagnostic test) to evaluate a diagnostic ability of each predictor (the plasma levels of NDE, ADE and ODE). The level of significance was set at p<0.05.

Figures 18A, 18B, 18C:
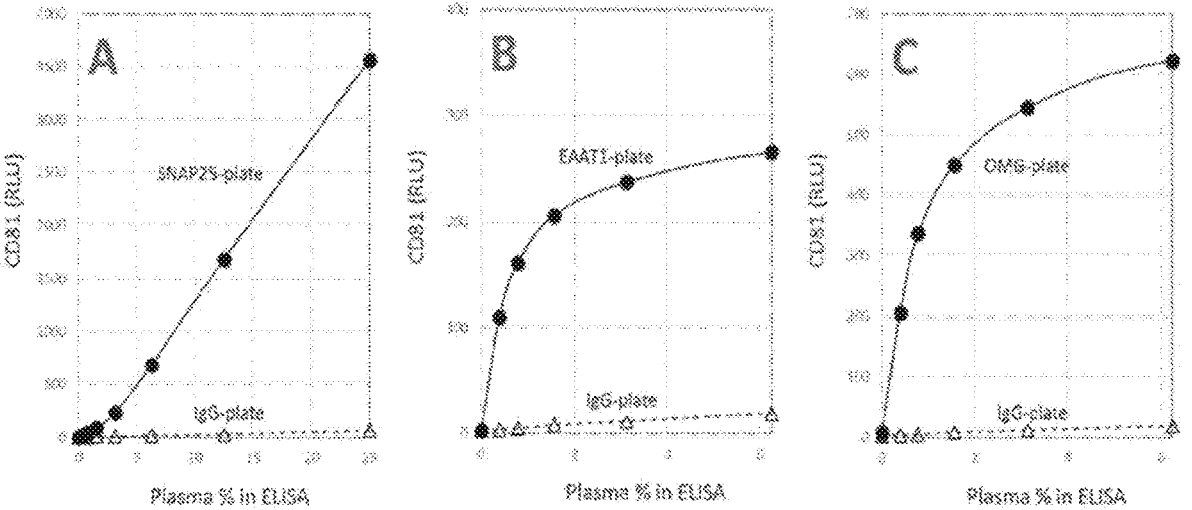
FIGS. 18A-18C set forth data showing the specificity of an exemplary assay of the present invention. Anti-SNAP25 (500 ng/ml) (A●), anti-EAAT1 (830 ng/mL) (B●), anti-OMG (830 ng/mL) (C●), and control mouse IgG (500 ng/mL) (Δ) were immobilized onto ELISA plates as described in the Methods. Serial dilution of a single donor plasma sample was prepared and applied to ELISA plates, then probed with biotinylated anti-CD81. ELISA results were expressed as relative light units (RLU).

ELISA specificity was determined as follows. ELISA plates were immobilized with either target antibodies (anti-SNAP25, anti-EAAT1, and anti-OMG) or control IgG, then serial dilutions of plasma was applied. As shown in FIGS. 18A-18C, ELISA readings (RLU) increased in proportion to the volume of plasma on target antibodies-immobilized ELISA plates (filled circles; ●), not control IgG-immobilized plates (open triangles; A). We also tested ELISA without biotin antibodies to assess non-specific binding of SA-HRP, however, no signal was detected. Since biotin antibodies were mixed with 10× volume of control mouse IgG, non-specific IgG binding was eliminated in the assay.

Figures 19A, 19B, 19C:
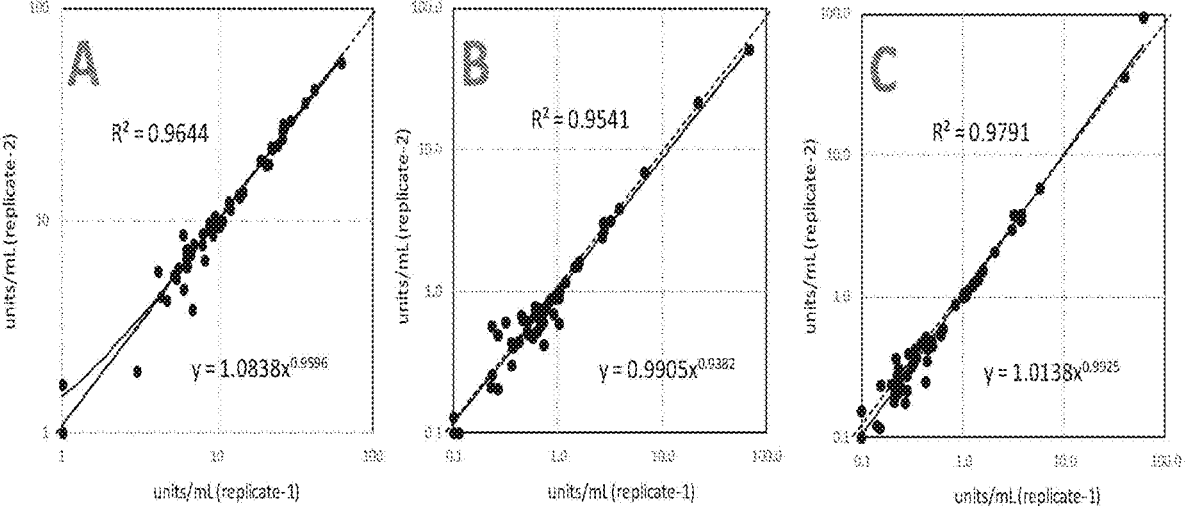
FIGS. 19A-19C set forth data showing intra-assay preci-sion of an exemplary assay of the present invention. NDE (A), ADE (B), and ODE (C) were enumerated in 52 samples (15 each of control, PD, MSA, and PSP) in duplicate, and each replicate was analyzed in x-y plot to show the intra-assay variation. Dotted lines are 45° line and solid lines are regression lines.
Figure 20A:
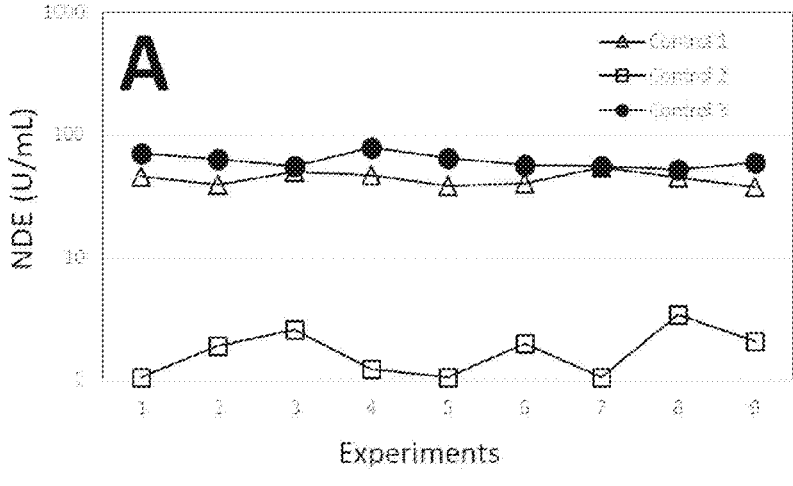
FIGS. 20A-20C set forth data showing inter-assay preci-sion for an exemplary assay of the present invention. NDE (A), ADE (B), and ODE (C) were enumerated in 3 different control plasma samples 9 separate times. In each experi-ment, 7 dilutions of standard plasma (arbitrary assigned 100 units/mL) and buffer control were analyzed simultaneously, then ELISA readings (RLU) were converted to units/mL. Average #standard deviation (CV %) of control plasma 1 (Δ), 2 (□), and 3 (●) were 64.6±9.2 units/mL (14.2%), 1.6±0.8 units/mL (52.9%), and 44.4±5.5 units/mL (12.4%) for NDE, 7.5±1.3 units/mL (16.8%), 2.6±0.5 units/mL (20.3%), and 0.2±0.1 units/mL (63.33%) for ADE, and 12.6±1.3 units/mL (10.1%), 2.6±0.3 units/mL (11.45%), and 0.2±0.1 units/mL (34.5%) for ODE, respectively.
Figure 20B:
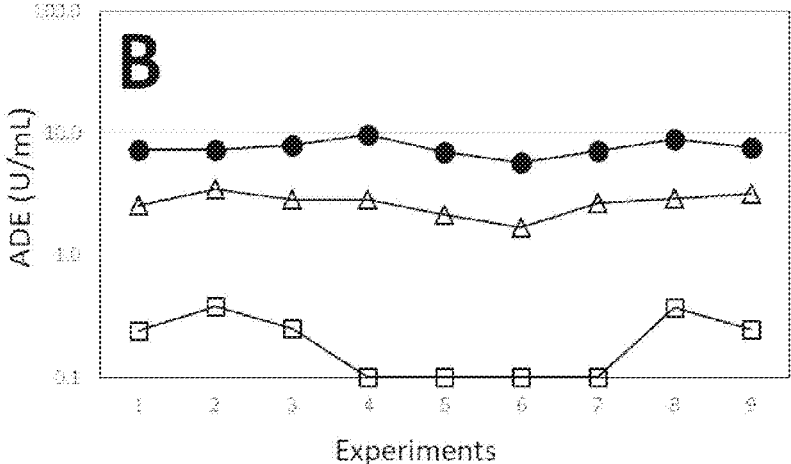
Figure 20C:
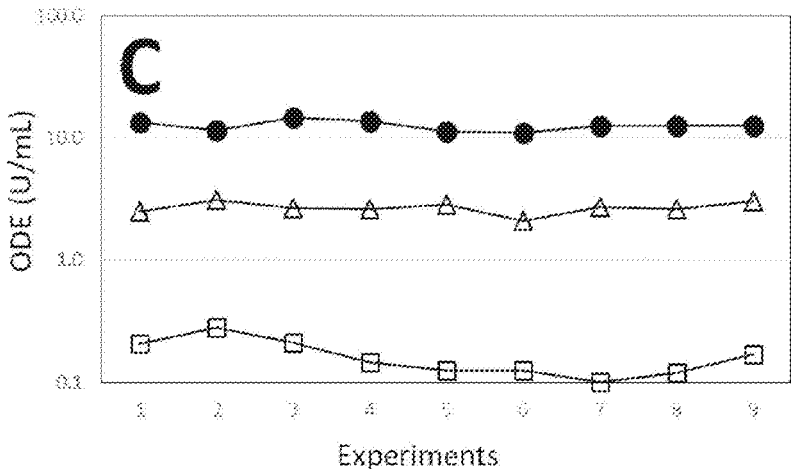

Next, the performance of the ELISA assays was determined. Intra-assay precision was determined by ELISAs carried out in duplicate using 52 different subjects. As shown in FIGS. 19A-19C, duplicate variation was very small in all of the three ELISAs ($r^2$=0.9644, 0.9541, and 0.9791 and slope=1.08, 0.99, and 1.01 for NDE, ADE, and ODE, respectively). Inter-assay precision was determined using 3 control plasma samples run 9 times. As shown in FIGS. 20A-20C, CV % of high and medium range plasma was <=20%, although very low range plasma (<10 units/mL for NDE, <1 units/mL for ADE and ODE) was 35-63%. The CV % was acceptable because we constructed ELISA plates in each experiment.

Figures 21A, 21B, 21C:
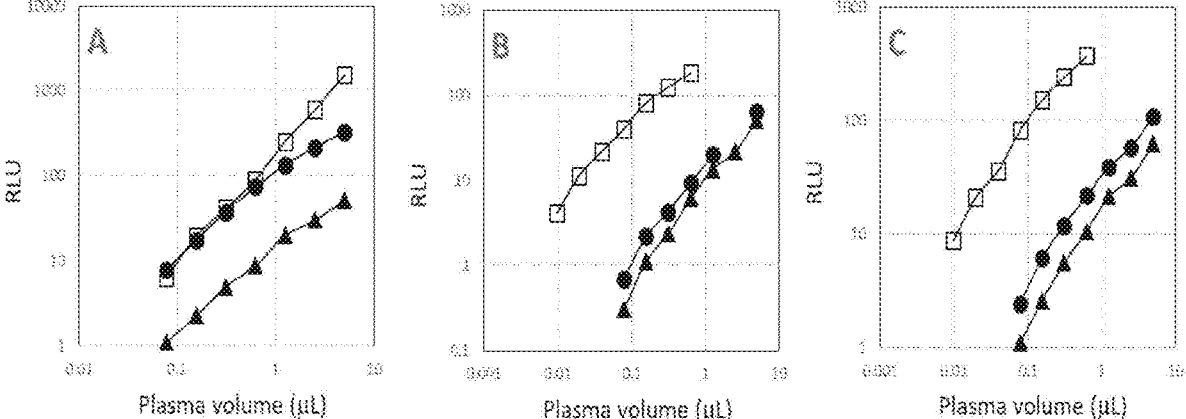
FIGS. 21A-21C set forth data showing dilutional linearity for an exemplary assay of the present invention. After screening of various control plasma samples, we found 3 plasma samples (□, ●, ▲), showing a wide range of NDE (A), ADE (B), and ODE (C). Then, plasma dilution study was carried out to analyze the linearity and the slope among 3 plasma samples.

In this ELISA, quantification of target plasma samples is based on the dilution curve of standard plasma. This calculation is applicable when the dilution curve between sample and standard are identical. To validate this hypothesis, dilutional linearity was determined by high, medium, and low range plasma samples. As shown in FIGS. 21A-21C, all 3 plasma showed linear dilution in NDE, ADE, and ODE, with almost identical slopes, even though the quantity of these 3 plasma varied widely around 1,000 folds. As shown in FIGS. 21A-21C, linear detection range was 0.1-5 uL plasma (NDE), 0.01-5 uL plasma (ADE and ODE), respectively.

Limit of detection (LOD) of NDE, ADE, and ODE was 0.519, 0, and 0.062 units/mL, respectively.

Enumeration of plasma BDE and comparison between patients and controls was determined as follows. Plasma levels of NDE, ADE and ODE were significantly higher in PD samples than in control samples, respectively (FIGS. 22A-22C; p=0.003 (t-test), p=0.003 (U test) for NDE, p=0.028 (t-test), p=0.021 (U test) for ADE, and p=0.016 (t-test), p=0.008 (U test) for ODE). When compared between PD and MSA groups, plasma levels of NDE were significantly higher in patients with PD than those with MSA (FIGS. 22A-22C; p=0.028 (t-test), p=0.023 (U test)), whereas no significant difference was found in ADE and ODE. Patients with PSP also showed significantly higher levels of plasma NDE, and ADE compared with the controls (FIGS. 22A-22B; p=0.038 (t-test), p=0.041 (U test) for NDE, and p=0.012 (t-test), p=0.025 (U test) for ADE).

FIGS. 23A-23C shows the ROC curves for the classification of patients with PD and controls based on the levels of plasma NDE, ADE, and ODE. The AUC of the ROC curve for plasma NDE, ADE and ODE were 0.89, 0.83, and 0.88, respectively, indicating that plasma levels of NDE, ADE, and ODE will be applicable to diagnostic tests for PD with substantial accuracy.

The correlation between BDE and clinical severity of the subjects with PD and MSA was determined as follows. We investigated the correlation between the levels of plasma BDE and scores of clinical severity in the patients with PD. As shown in FIGS. 24A-24F, plasma levels of all BDE (NDE, ADE and ODE) were significantly higher in the patients with advanced PD, namely in both groups with mRS grade 4 (n=4) (p=0.003 (t-test), p=0.008 (U test) for NDE, p=0.001 (t-test), p=0.006 (U test) for ADE, and p<0.001 (t-test), p=0.006 (U test) for ODE, and those with Hoehn and Yahr (HY) stage 4 (n=5) (p=0.001 (t-test), p=0.003 (U test) for NDE, p=0.001 (t-test), p=0.003 (U test) for ADE, and p<0.001 (t-test), p=0.003 (U test) for ODE, compared with the control group. Furthermore, plasma levels of NDE were significantly higher even in the mild PD patients, who were in mRS grade 1-2 (n=5) (p=0.001 (t-test), p=0.002 (U test)) or in HY stage 1-2 (n=4) (p=0.003 (t-test), p=0.004 (U test)), compared with the controls. Less remarkably, but nevertheless significantly, plasma levels of ODE were also higher even in the mild PD patients with mRS grade 1-2 (p=0.002 (t-test), p=0.005 (U test)) or in HY stage 1-2 (p=0.011 (U test)) compared with the controls. Moreover, plasma levels of ADE were also higher even in the mild PD patients with mRS grade 1-2 (p=0.023 (U test)) compared with the controls. These results indicate that the plasma levels of NDE and ODE could be useful as a diagnostic biomarker for PD patients especially in early disease stages. Although the levels of ODE were fluctuated during early disease courses of mRS and Yahr score 1-3, the levels of ODE were significantly higher in mRS and Yahr score 4 than score 1-3 (p=0.002 (t-test), p=0.011 (U test) for mRS, and p=0.004 (t-test), p=0.0024 (U test) in Yahr). This suggests that ODE may be a potential surrogate biomarker of the monitoring of disease progression of PD.

We further investigated the correlations between the levels of BDE or the ratios between them (ADE/NDE, ODE/NDE, and ODE/ADE) and various clinical parameters in the PD group (see Table 4). The ratio of ADE/NDE showed statistically significant high $r^2$ values for disease duration of the patients ($r^2$=0.51, n=15, p=0.0028), grades of mRS ($r^2$=0.47, n=15, p=0.0048), and UPDRS part III scores ($r^2$=0.52, n=14, p=0.0036), as well as ODE/NDE for UPDRS part III scores ($r^2$=0.51, n=14, p=0.0041) (FIGS. 25A-25D). These results also suggest that the plasma levels of BDE could possibly be useful for monitoring severity of patients with PD.

TABLE 4

Correlation between BDE and PD severity. * = $r^2$ values.

| | Quantity of BDE | | | Ratio | | |
|---|---|---|---|---|---|---|
| | NDE | ADE | ODE | A/N | O/N | O/A |
| Severity | 0.00 * | 0.21 | 0.19 | 0.38 | 0.31 | 0.03 |
| Dis.duration(M) | 0.02 | 0.33 | 0.22 | 0.51 | 0.30 | 0.00 |
| mRS | 0.00 | 0.20 | 0.19 | 0.47 | 0.39 | 0.04 |

TABLE 4-continued

Correlation between BDE and PD severity. * = $r^2$ values.

| | Quantity of BDE | | | Ratio | | |
|---|---|---|---|---|---|---|
| | NDE | ADE | ODE | A/N | O/N | O/A |
| mRS/duration | 0.01 | 0.12 | 0.11 | 0.33 | 0.27 | 0.03 |
| Yahr grade | 0.00 | 0.21 | 0.19 | 0.38 | 0.31 | 0.03 |
| Yahr/duration | 0.02 | 0.08 | 0.09 | 0.29 | 0.24 | 0.03 |
| UPDRS part3(motor) | 0.03 | 0.35 | 0.36 | 0.52 | 0.51 | 0.12 |
| UPDRS/duration | 0.01 | 0.07 | 0.04 | 0.23 | 0.11 | 0.01 |
| DM | 0.16 | 0.12 | 0.17 | 0.04 | 0.10 | 0.16 |
| MMSE | 0.01 | 0.03 | 0.02 | 0.03 | 0.02 | 0.01 |

* $r^2$ values

Next, we investigated the correlations between the levels of BDE and various clinical parameters in the MSA group. As shown in FIG. 26A-26D, plasma levels of ODE did not correlate with the grades of mRS or disease duration in the patients with MSA as a whole, or not with ICARS scores in MSA-C, but had a significant correlation with UPDRS part III scores ($r^2$=0.57, n=6, p=0.048).

These results showed that plasma levels of both NDE and ODE are significantly increased when compared to controls, even in the early stages of PD and that the levels of ODE increased according to the progression of disease severity in PD. These results further showed that plasma levels of BDE could be diagnostic and severity-level biomarkers for PD and related diseases. These results showed that the methods and compositions of the present invention are useful for identifying, detecting, and measuring biomarkers on exosomes, wherein the exosomes are not lysed or permeabilized. These results further suggested that the methods and compositions of the present invention would be useful for diagnosing neurological disease in a subject. These results further suggested that the methods and compositions of the present invention would be useful for diagnosing a disease or disorder.

Example 15: Detection of Pathological Form of α-Synuclein on the Surface of Neuron-, Astrocyte-, and Oligodendrocyte-Derived Exosomes The detection of pathological form of a-synuclein on the surface of neuron-, astrocyte-, and oligodendrocyte-derived exosomes was performed as followed. Forty uL of EDTA plasma samples (¼ dilution in PBS) were added into anti-SNAP25-, EAAT1-. And OMG-immobilized immobilized ELISA plate to capture neuron-(NDE), astrocyte-(ADE), and oligodendrocyte-(ODE) derived exosomes. After each well was washed, biotinylated antibodies against aggregated forms (pathological forms) of α-synuclein (Syn-F1, Syn-O2 from BioLegend) were applied, and incubation was continued for another hour, followed by ordinary ELISA procedures (HRP reaction, SuperSignal, measurement of chemiluminescence signals). As shown in FIGS. 27A-27F, pathological α-synuclein was detected in patients with PD, MSA, and PSP. Statistical significance was based on Mann-Whitney U test.

These results showed that the methods and compositions of the present invention are useful for identifying, detecting, and measuring biomarkers on exosomes, wherein the exosomes are not lysed or permeabilized. These results further suggested that the methods and compositions of the present invention would be useful for diagnosing neurological disease in a subject. These results further suggested that the methods and compositions of the present invention would be useful for diagnosing a disease or disorder.

Example 16: Detection of Dopamine Receptor D2 (DRD2) on the Surface of Neuron-Derived Exosomes The detection of dopamine receptor D2 (DRD2) on the surface of neuron-derived exosomes was performed as followed. Anti-SNAP25 (neuron marker), anti-DRD2, and control mouse IgG were immobilized on an ELISA plate. Next, human EDTA plasma or buffer control (phosphate buffered saline, PBS) was applied to the ELISA plate, followed by a reaction with biotinylated anti-SNAP25. As shown in FIG. 28A, plasma was positive on both anti-SNAP25 and anti-DRD2 antibody ELISA plate, whereas PBS was not.

In another series of experiments, anti-SNAP25 and control mouse IgG were immobilized on an ELISA plate, human EDTA plasma or PBS was applied to the ELISA plate, followed by a reaction with biotinylated antibodies against SNAP25, CD81 (exosome common marker), DRD2, as well as PBS control. As shown in FIG. 28B, plasma was positive in anti-SNAP25, CD81, and DRD2 probes on anti-SNAP25 antibody ELISA plate.

A plasma dilution study was performed as follows. Anti-SNAP25 was immobilized on an ELISA plate and serial dilutions of human EDTA plasma samples (3 different donors) were applied to the ELISA plate, followed by the reaction with biotinylated anti-DRD2 and anti-CD81. As shown in FIGS. 29A and 29B, plasma dilution slope was almost identical among 3 donors. Therefore, the ratio of DRD2/CD81 was consistent (see FIG. 29C).

In another series of experiments, DRD2 was detected in neuron-derived exosomes in plasma samples from humans with neurological disease. Standard plasma was assigned to 100 units/mL, then using the dilution curve, ELISA reading (DRD2 probes on SNAP25 plate, and CD81 probes on SNAP25 plate (NDE)) of each sample was converted to units/mL (U/mL). Plasma samples from 15 each of control, Parkinson's disease (PD), multiple system atrophy (MSA), and 7 patients with progressive supranuclear palsy (PSP) were analyzed. PD and MSA patients were further categorized by the severity of disease (mRS score). As shown in FIGS. 30A-30G, the levels of DRD2 in PD were significantly lower than control, although the levels of NDE were significantly higher in PD than control. Thus, the ratio (DRD2/NDE) showed more significant differences between PD samples and control samples. Moreover, the decrease in DRD2 was shown in the mild cases of PD (mRS score 1+2), indicating that DRD2 may be used as a marker for the early screening of PD patients as well as the monitoring of PD progression. ROC curve and area under the curve (AUC) for DRD2 levels between PD and control samples are shown in FIG. 31.

These results showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing a neurological disorder in a subject. These results further suggested that the methods and compositions of the present invention would be useful for diagnosing a disease or disorder.

Example 17: Detection of DAT-Positive Extracellular Vesicles

Figures 32A, 32B, 32C, 32D:
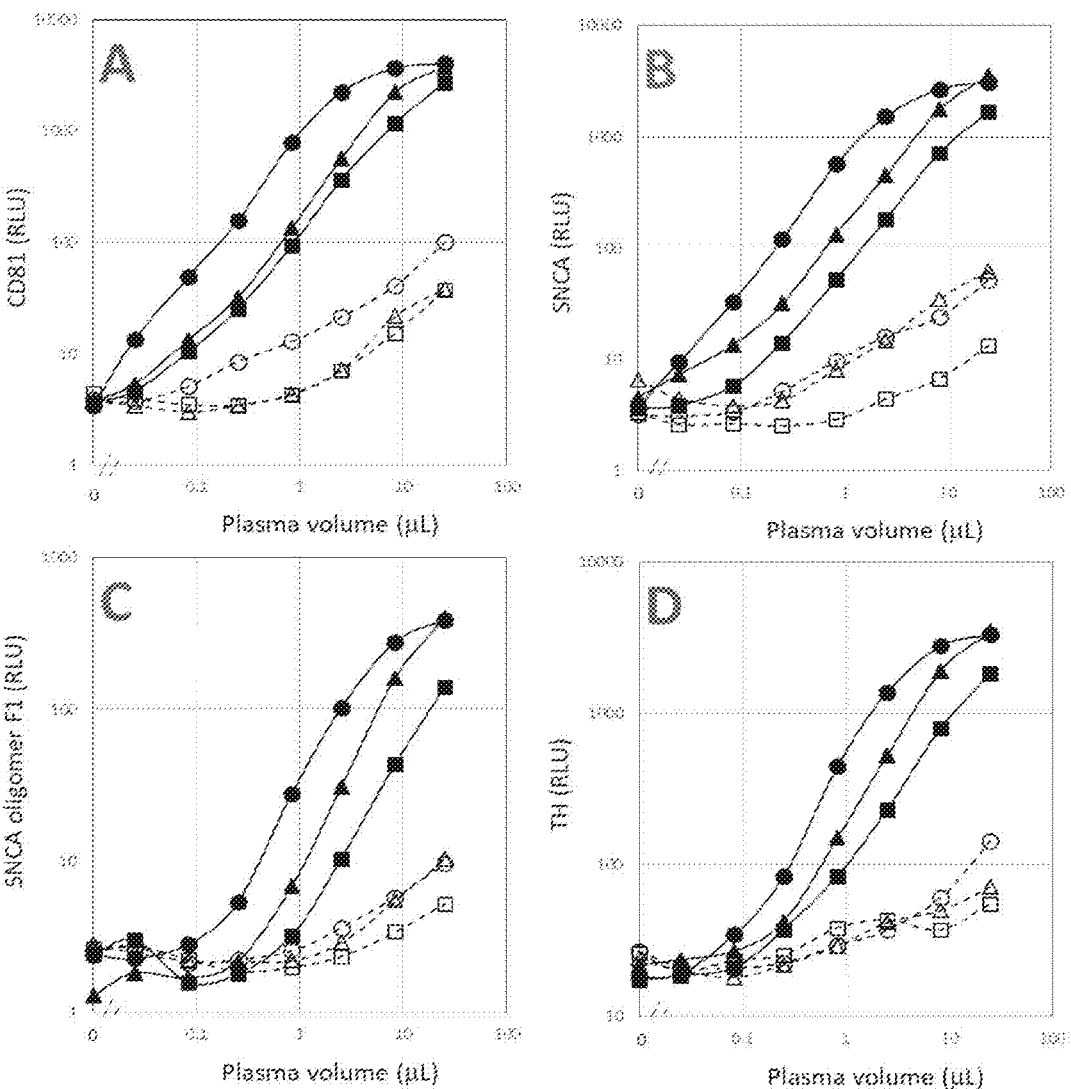

DAT-positive extracellular vesicles were captured on ELISA plates and analyzed as follows. Plasma samples obtained from three different human control donors were diluted in PBS. Sample were applied to a pair of enzyme linked immunosorbent assay (ELISA) wells, one well was immobilized with anti-DAT mouse monoclonal antibody (FIG. 32, ●▲■) and the other well was immobilized with control mouse IgG (FIG. 32, oAu). After DAT extracellular vesicles (EV) were captured on the ELISA wells, unbound materials were removed by extensive washing, then probed with labeled anti-CD81 to quantify $DAT^{30}$-$CD81^+$ double positive signals (=DAT EV) (FIG. 32A), as well as antibodies against monomer (FIG. 32B), oligomer a-synuclein (SNCA) (FIG. 32C), and tyrosine hydroxylase (TH) (FIG. 32D) to quantify SNCA and TH on the surface of $DAT^+$ EV.

As shown in FIG. 32, the plasma samples on $DAT^+$ ELISA wells all showed dose-dependent signal changes, whereas those of control IgG ELISA wells stayed very low, $\frac{1}{10}$ to $\frac{1}{100}$ lower than those of DAT ELISA wells. More importantly, the slopes of three plasma samples were very similar, indicating that the dilution curve of one particular plasma can be used as a universal quantification standard.

These results showed that the methods and compositions of the present invention are useful for capturing and detecting DAT-positive extracellular vesicles. These results further showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing a neurological disease or disorder in a subject.

Example 18: Detection of SNAP25-Positive, EAAT1-Positive, and OMG-Positive Extracellular Vesicles SNAP25-positive, EAAT1-positive, and OMG-positive extracellular vesicles were captured on ELISA plates and analyzed as follows. Plasma samples obtained from control donors were applied to ELISA plates where antibodies against SNAP25, EAAT1, and OMG were previously immobilized. After captured extracellular vesicles (EV) were washed extensively, EVs were eluted by incubation with a pH 12.5 elution buffer for 5 minutes, then immediately neutralized. These samples were applied to Nanoparticle Tracking Analysis (NanoSight).

As shown in FIG. 33, EV was detected in all samples with the size range from 100-400 nm. Moreover, EV size of SNAP25 was smaller than those of EAAT1 and OMG.

These results showed that the methods and compositions of the present invention are useful for capturing and detecting SNAP25-positive, EAAT1-positive, and OMG-positive extracellular vesicles. These results further showed that the methods and compositions of the present invention are useful for identifying, detecting, and measuring biomarkers on vesicles, wherein the vesicles are not lysed or permeabilized. These results further suggested that the methods and compositions of the present invention would be useful for diagnosing a neurological disease or disorder in a subject.

Example 19: Detection of Biomarkers on the Surface of Exosomes

Multiple membrane biomarkers were detected on the surface of exosomes as follows. Various antibodies were suspended in a coating buffer and applied to an ELISA plate. After an hour of incubation, each well was washed once, then blocking solution (0.5% BSA in Blocker casein) was added, and incubation was continued for an additional hour. After washing each well twice, plasma or buffer control (phosphate buffered saline, PBS) was added, then incubation was continued in a refrigerator overnight. After washing each well twice, biotinylated anti-EAAT1, anti-SNAP25, anti-OMG, or anti-CD11b was added and incubation was continued for an hour. After washing each well twice, streptavidin-horseradish peroxidase was added, and incubation was continued for another 30 minutes. After washing each well three times, SuperSignal substrate was added and chemiluminescent signals were measured in a luminometer.

As shown in FIG. 35, multiple biomarkers were detected on the surface of SNAP25+, EAAT1+, OMG+, and CD11b+ exosomes.

As shown in FIG. 34, all three control plasma showed partcile ranging from 50-400 nm in size. These results demonstrated that the particles captured according to the methods described in Example 17 above were extracellular vesicles.

These results showed that methods of the present invention are useful for detecting biomarkers on the surface of exosomes. These results showed that the methods and compositions of the present invention are useful for identifying, detecting, and measuring biomarkers on exosomes, wherein the exosomes are not lysed or permeabilized. These results further suggested that the methods and compositions of the present invention would be useful for diagnosing neurological disease in a subject. These results further suggested that the methods and compositions of the present invention would be useful for diagnosing a disease or disorder.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method comprising:
a) providing a biological sample comprising vesicles;
b) contacting a solid support comprising capture agents associated therewith with the biological sample under conditions wherein the capture agents selectively bind to a first biomarker, if present, on the vesicles, thereby capturing said vesicles having said first biomarker on the solid support;
c) separating the solid support from the biological sample; and
d) detecting a second biomarker on the vesicles captured on the solid support using a detection agent that selectively binds to the second biomarker, wherein the vesicles are not lysed or permeabilized, wherein the second biomarker comprises a cytosolic protein or a secretory protein, and wherein the first biomarker or the second biomarker is selected from the group consisting of a neuron-specific protein, an astrocyte-specific protein, a microglia-specific protein, and an oligodendrocyte-specific protein.

2. The method of claim 1, wherein
(i) the vesicles are selected from the group consisting of exosomes, microparticles, microvesicles, nanosomes, extracellular vesicles, ectosomes, and apoptotic bodies;
(ii) the first and second biomarkers are membrane-bound proteins or adsorbed proteins on the vesicles;
(iii) the first or second biomarker is an exosome surface marker; or (iv) the first or second biomarker is an exosome surface marker and the exosome surface marker is CD81, CD63, CD171, SNAP25, EAAT1, CD11b, DAT or OMG.

3. The method of claim 1, wherein the neuron-specific protein is selected from the group consisting of NRGN, Tau, phosphorylated Tau, synaptophysin, αβ-42, alpha-synuclein (SNCA), AchE, LAMP1, REST, SYT, SYP, SYNPO, PSD95, SV2A, CCL2, IL34, GYS, OR, DR6, HSP, IL12b, Aβ, and BACE.

4. The method of claim 1, wherein the astrocyte-specific proteins are selected from the group consisting of glial fibrillary acidic protein (GFAP) and excitatory amino acid transporter 1 (EAAT1).

5. The method of claim 1, wherein the oligodendrocyte-specific protein is selected from the group consisting of myelin basic protein (MBP) and oligodendrocyte myelin glycoprotein (OMG).

6. The method of claim 1, wherein the vesicles captured on the solid support are selected from the group consisting of neuron-derived exosomes, astrocyte-derived exosomes, oligodendrocyte-derived exosomes, and microglia-derived exosomes.

7. The method of claim 1, further comprising detecting a cytosolic protein on the vesicles captured on the solid support.

8. The method of claim 7, wherein the cytosolic protein is GAPDH, CTSD, NRGN, MBP, GFAP, Tau, phosphorylated Tau, synaptophysin, SNCA, αβ-42, AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, or PSG1.

9. The method of claim 8, wherein the cytosolic protein is a pathological form, including aggregates and/or mutated form of GAPDH, CTSD, NRGN, MBP, GFAP, Tau, phosphorylated Tau, synaptophysin, SNCA, αβ-42, AchE, LAMP1, REST, SYT, TH, SYP, SYNPO, PSD95, SV2A, GYS, HSP70, BACE, SYMPO, NEFL, caspase, ubiquitin, PSEN1, GSK, PLAP, CSH1, or PSG1.

10. The method of claim 1, further comprising detecting a secretory protein on the vesicles captured on the solid support.

11. The method of claim 10, wherein the secretory protein is selected from the group consisting of cytokines, growth factors, chemokines, interleukins, nociceptin (opioid peptide), and GnRH.

12. The method of claim 11, wherein the cytokine is selected from the group consisting of IL1b, IL34, IL6, IL8, IL16, IL23A, IL32, IL33, CX3CL1, CCL2, CXCL12, TNFalpha, TNFSF10, TNFSF13, IL12B, and FasL.

13. The method of claim 1, further comprising detecting a receptor protein, a transporter protein, or a membrane protein on the vesicles captured on the solid support.

14. The method of claim 13, wherein the receptor protein is a neurotransmitter receptor, a dopamine receptor, a serotonin receptor, a GABA receptor, a glutamate receptor, an insulin receptor, a tumor necrosis factor receptor, or a neuropeptide receptor.

15. The method of claim 13, wherein the membrane protein is EpCAM, PD-L1, ErbB2, CK19, TCR, CD16, CD28, CD32, CD79a, TREM2, or NCAM.

16. The method of claim 13, wherein the transporter protein is a neurotransmitter transporter, a dopamine transporter (DAT), a serotonin transporter, a GABA transporter, a glutamate transporter, an insulin transporter, a tumor necrosis factor transporter, or a neuropeptide transporter.

17. The method of claim 1, wherein the solid support is a plate, a non-magnetic bead, a magnetic bead, a filter, a slide, a wafer, a rod, a particle, a strand, a disc, a membrane, or a surface of a tube, channel, column, flow cell device, or microfluidic device.

18. The method of claim 1, wherein the capture agents comprise antibodies, antibody fragments, antibody mimetics, or aptamers that specifically bind to the first biomarker on the vesicles.

19. The method of claim 1, wherein the detection agent comprises an antibody, an antibody fragment, an antibody mimetic, or an aptamer that specifically binds to the second biomarker on the vesicles.

20. The method of claim 1, wherein said detecting comprises performing an immunoassay.

21. The method of claim 20, wherein the immunoassay is selected from the group consisting of an enzyme-linked immunosorbent assay (ELISA), an immunofluorescent assay (IFA), an immune-polymerase chain reaction assay, an electro-chemiluminescence immunoassay (ECLIA), and a radioimmunoassay (RIA).

\* \* \* \* \*